United States Patent
Sharma et al.

(10) Patent No.: US 12,014,722 B2
(45) Date of Patent: Jun. 18, 2024

(54) SYSTEM AND METHOD FOR DATA AUGMENTATION OF FEATURE-BASED VOICE DATA

(71) Applicant: Microsoft Technology Licensing, LLC, Redmond, WA (US)

(72) Inventors: Dushyant Sharma, Woburn, MA (US); Patrick A. Naylor, Reading (GB); James W. Fosburgh, Winchester, MA (US)

(73) Assignee: Microsoft Technology Licensing, LLC, Redmond, WA (US)

(*) Notice: Subject to any disclaimer, the term of this patent is extended or adjusted under 35 U.S.C. 154(b) by 0 days.

(21) Appl. No.: 17/197,587

(22) Filed: Mar. 10, 2021

(65) Prior Publication Data
US 2021/0287660 A1     Sep. 16, 2021

Related U.S. Application Data

(60) Provisional application No. 62/988,337, filed on Mar. 11, 2020.

(51) Int. Cl.
*G10L 13/02*     (2013.01)
*G06F 3/16*     (2006.01)
(Continued)

(52) U.S. Cl.
CPC .......... *G10L 13/02* (2013.01); *G06F 3/165* (2013.01); *G06N 5/02* (2013.01); *G06N 20/00* (2019.01); *G10K 15/08* (2013.01); *G10L 13/033* (2013.01); *G10L 15/02* (2013.01); *G10L 15/063* (2013.01); *G10L 15/065* (2013.01); *G10L 21/0224* (2013.01); *G10L 25/03* (2013.01);
(Continued)

(58) Field of Classification Search
CPC ..... G10L 15/00; G10L 2015/00; G10L 13/00; G10L 21/00; G10L 25/00
See application file for complete search history.

(56) References Cited

U.S. PATENT DOCUMENTS 3,983,482 A * 9/1976 Doherty ................. H04B 7/17
                                                           342/45
6,490,553 B2    12/2002    Van et al.
(Continued)

FOREIGN PATENT DOCUMENTS

EP     21766972.0     3/2021
EP     21767052.0     3/2021
(Continued)

OTHER PUBLICATIONS

J. F. Gemmeke et al., "Audio Set: An ontology and human-labeled dataset for audio events," 2017 IEEE International Conference on Acoustics, Speech and Signal Processing (ICASSP), 2017, pp. 776-780, doi: 10.1109/ICASSP.2017.7952261. (Year: 2017).*
(Continued)

*Primary Examiner* — Neeraj Sharma
(74) *Attorney, Agent, or Firm* — Brian J. Colandreo; Heath M. Sargeant; Holland & Knight LLP

(57) ABSTRACT

A method, computer program product, and computing system for receiving feature-based voice data associated with a first acoustic domain. One or more gain-based augmentations may be performed on at least a portion of the feature-based voice data, thus defining gain-augmented feature-based voice data.

20 Claims, 17 Drawing Sheets

(51) Int. Cl.

| | |
|---|---|
| *G06N 5/02* | (2023.01) |
| *G06N 20/00* | (2019.01) |
| *G10K 15/08* | (2006.01) |
| *G10L 13/033* | (2013.01) |
| *G10L 15/02* | (2006.01) |
| *G10L 15/06* | (2013.01) |
| *G10L 15/065* | (2013.01) |
| *G10L 21/0224* | (2013.01) |
| *G10L 25/03* | (2013.01) |
| *H04S 7/00* | (2006.01) |

(52) U.S. Cl.
CPC ............... *H04S 7/30* (2013.01); *H04S 7/302* (2013.01); *H04S 7/303* (2013.01)

(56) References Cited

U.S. PATENT DOCUMENTS

| | | | |
|---|---|---|---|
| 6,836,761 B1 | 12/2004 | Kawashima et al. | |
| 8,761,410 B1 | 6/2014 | Avendano | |
| 8,838,446 B2 | 9/2014 | Jeong et al. | |
| 9,008,329 B1* | 4/2015 | Mandel .................. | G10K 15/00 704/226 |
| 9,202,464 B1 | 12/2015 | Senior et al. | |
| 9,922,664 B2 | 3/2018 | Sharma et al. | |
| 10,296,959 B1 | 5/2019 | Chernikhova et al. | |
| 10,475,471 B2 | 11/2019 | Ebenezer | |
| 10,559,299 B1 | 2/2020 | Arel et al. | |
| 10,595,149 B1 | 3/2020 | Lovitt et al. | |
| 10,796,702 B2* | 10/2020 | Li ........................... | G10L 17/00 |
| 10,841,424 B1 | 11/2020 | Lemus et al. | |
| 11,132,993 B1* | 9/2021 | McDaniel ............. | G06F 40/284 |
| 11,361,749 B2 | 6/2022 | Sharma et al. | |
| 11,380,312 B1* | 7/2022 | Mansour ................. | G10L 15/08 |
| 11,398,216 B2 | 7/2022 | Sharma et al. | |
| 11,482,241 B2* | 10/2022 | Sharma ............... | G10L 19/0018 |
| 11,863,948 B1* | 1/2024 | Kwatra .................. | H04R 5/033 |
| 2001/0047267 A1 | 11/2001 | Abiko et al. | |
| 2002/0087306 A1 | 7/2002 | Lee et al. | |
| 2002/0087314 A1 | 7/2002 | Fischer et al. | |
| 2008/0147413 A1 | 6/2008 | Sobol-shikler | |
| 2008/0188257 A1* | 8/2008 | Mickle .................... | H04B 5/77 455/522 |
| 2010/0164990 A1 | 7/2010 | Van | |
| 2011/0051948 A1* | 3/2011 | Boldt ................... | H04R 25/505 381/73.1 |
| 2011/0066390 A1* | 3/2011 | Macleod ................. | G01N 3/06 702/56 |
| 2011/0103468 A1 | 5/2011 | Polisetty et al. | |
| 2012/0314842 A1 | 12/2012 | Kargar et al. | |
| 2013/0073960 A1 | 3/2013 | Eppolito et al. | |
| 2013/0151247 A1* | 6/2013 | Lou ....................... | H04M 9/082 704/226 |
| 2013/0211826 A1 | 8/2013 | Mannby | |
| 2013/0215281 A1 | 8/2013 | Hobby et al. | |
| 2013/0262096 A1 | 10/2013 | Wilhelms-tricarico et al. | |
| 2014/0294200 A1 | 10/2014 | Baumgarte et al. | |
| 2015/0092950 A1 | 4/2015 | Kim et al. | |
| 2015/0117652 A1* | 4/2015 | Sato .................... | G10L 21/0216 381/56 |
| 2015/0195406 A1 | 7/2015 | Dwyer et al. | |
| 2015/0294669 A1 | 10/2015 | Zhang et al. | |
| 2015/0332680 A1 | 11/2015 | Crockett et al. | |
| 2016/0080907 A1 | 3/2016 | Saleem | |
| 2016/0187654 A1 | 6/2016 | Border et al. | |
| 2016/0240210 A1 | 8/2016 | Lou | |
| 2016/0275947 A1 | 9/2016 | Li et al. | |
| 2016/0307459 A1 | 10/2016 | Chestnut et al. | |
| 2017/0200446 A1 | 7/2017 | Cui et al. | |
| 2017/0330071 A1* | 11/2017 | Roblek ..................... | G06F 3/16 |
| 2018/0018590 A1 | 1/2018 | Szeto et al. | |
| 2018/0082692 A1 | 3/2018 | Khoury et al. | |
| 2018/0146047 A1* | 5/2018 | Biswas .................. | G06N 20/10 |
| 2018/0242098 A1 | 8/2018 | Pratt | |
| 2018/0315421 A1 | 11/2018 | Eck et al. | |
| 2018/0330713 A1* | 11/2018 | Hoory .................... | G10L 13/033 |
| 2018/0342258 A1 | 11/2018 | Huffman et al. | |
| 2019/0013013 A1 | 1/2019 | Mclaren et al. | |
| 2019/0028696 A1 | 1/2019 | Dietz et al. | |
| 2019/0035415 A1* | 1/2019 | Lu ........................ | G10L 21/0364 |
| 2019/0088269 A1 | 3/2019 | Markovich Golan et al. | |
| 2019/0130903 A1 | 5/2019 | Sriram et al. | |
| 2019/0272145 A1 | 9/2019 | Sharma et al. | |
| 2019/0272818 A1 | 9/2019 | Fernandez et al. | |
| 2019/0272840 A1 | 9/2019 | Caroselli et al. | |
| 2019/0282055 A1 | 9/2019 | Lee et al. | |
| 2019/0304437 A1 | 10/2019 | Qian et al. | |
| 2019/0349703 A1 | 11/2019 | Zilberman et al. | |
| 2019/0362711 A1 | 11/2019 | Nosrati et al. | |
| 2020/0050701 A1 | 2/2020 | Ramasamy et al. | |
| 2020/0051544 A1* | 2/2020 | Laput .................... | G10L 13/033 |
| 2020/0258510 A1* | 8/2020 | Lavery .................. | G16H 10/20 |
| 2020/0275207 A1 | 8/2020 | Zilberman et al. | |
| 2020/0285702 A1* | 9/2020 | Padhi ....................... | G06N 3/08 |
| 2020/0309930 A1* | 10/2020 | Zhou ....................... | G01S 15/86 |
| 2020/0311300 A1 | 10/2020 | Callcut | |
| 2020/0335086 A1 | 10/2020 | Paraskevopoulos et al. | |
| 2021/0035563 A1* | 2/2021 | Cartwright ............ | G10L 15/142 |
| 2021/0043186 A1 | 2/2021 | Nagano et al. | |
| 2021/0055778 A1* | 2/2021 | Myer ..................... | G06N 3/049 |
| 2021/0287104 A1 | 9/2021 | Sharma et al. | |
| 2021/0287105 A1 | 9/2021 | Sharma et al. | |
| 2021/0287652 A1 | 9/2021 | Sharma et al. | |
| 2021/0287653 A1 | 9/2021 | Sharma et al. | |
| 2021/0287654 A1 | 9/2021 | Sharma et al. | |
| 2021/0287659 A1 | 9/2021 | Sharma et al. | |
| 2021/0287661 A1 | 9/2021 | Sharma et al. | |
| 2021/0304737 A1 | 9/2021 | Han et al. | |
| 2022/0270625 A1 | 8/2022 | Dai et al. | |
| 2022/0301573 A1* | 9/2022 | Wang ...................... | G10L 17/02 |

FOREIGN PATENT DOCUMENTS

| | | |
|---|---|---|
| EP | 21768010.7 | 3/2021 |
| IN | 202217050387 | 3/2021 |
| IN | 202217050390 | 3/2021 |
| WO | 2019104229 A1 | 5/2019 |
| WO | 2019160556 A1 | 8/2019 |

OTHER PUBLICATIONS

Laput, Gierad, et al. "Ubicoustics: Plug-and-play acoustic activity recognition." Proceedings of the 31st Annual ACM Symposium on User Interface Software and Technology. 2018. (Year: 2018).*

Arakawa, Riku, Shinnosuke Takamichi, and Hiroshi Saruwatari. "Implementation of DNN-based real-time voice conversion and its improvements by audio data augmentation and mask-shaped device." Proc. SSW10. 2019. (Year: 2019).*

Park et al. "Google AI Blog: SpecAugment: A New Data Augmentation Method for Automatic Speech Recognition," Jun. 25, 2020, pp. 1-5.

Saon et al., "Sequence Noise Injected Training for End-To-End Speech Recognition," Downloaded on Jun. 25, 2020 at 23:02:10 UTC from IEEE Xplore, pp. 6261-6265.

"International Search Report and Written Opinion Issued in PCT Application No. PCT/US21/021716", dated May 25, 2021, 12 Pages.

"Final Office Action Issued in U.S. Appl. No. 17/077,863", dated May 5, 2021, 17 Pages.

"Non Final Office Action Issued in U.S. Appl. No. 17/077,863", dated Jan. 15, 2021, 15 Pages.

"Notice of Allowance Issued in U.S. Appl. No. 17/077,863", dated Jun. 29, 2022, 3 Pages.

"Advisory Action Issued in U.S. Appl. No. 17/077,965", dated Jul. 13, 2021, 4 Pages.

"Final Office Action Issued in U.S. Appl. No. 17/077,965", dated Apr. 21, 2021, 10 Pages.

"Non Final Office Action Issued in U.S. Appl. No. 17/077,965", dated Jan. 4, 2021, 7 Pages.

(56) References Cited

OTHER PUBLICATIONS

"Non Final Office Action Issued in U.S. Appl. No. 17/077,965", dated Nov. 9, 2021, 8 Pages.
"Notice of Allowance Issued in U.S. Appl. No. 17/077,965", dated May 18, 2022, 6 Pages.
"Notice of Allowance Issued in U.S. Appl. No. 17/077,965", dated Feb. 24, 2022, 8 Pages.
"Non Final Office Action Issued in U.S. Appl. No. 17/197,717", dated Jul. 14, 2022, 10 Pages.
"International Search Report and Written Opinion Issued in PCT Application No. PCT/US21/021712", dated May 20, 2021, 15 Pages.
"International Search Report and Written Opinion Issued in PCT Application No. PCT/US21/021721", dated Jun. 15, 2021, 14 Pages.
"International Search Report and Written Opinion Issued in PCT Application No. PCT/US21/021725", dated Jun. 15, 2021, 14 Pages.
"International Search Report and Written Opinion Issued in PCT Application No. PCT/US21/021730", dated Jun. 3, 2021, 13 Pages.
"International Search Report and Written Opinion Issued in PCT Application No. PCT/US21/021745", dated May 25, 2021, 8 Pages.
"International Search Report and Written Opinion Issued in PCT Application No. PCT/US21/021965", dated Apr. 8, 2021, 8 Pages.
"International Search Report and Written Opinion Issued in PCT Application No. PCT/US21/021968", dated Apr. 8, 2021, 7 Pages.
"Notice of Allowance Issued in U.S. Appl. No. 17/077,863", dated Mar. 14, 2022, 10 Pages.
"Final Office Action Issued in U.S. Appl. No. 17/197,549", dated Feb. 7, 2023, 18 Pages.
"Non Final Office Action Issued in U.S. Appl. No. 17/197,549", dated Sep. 1, 2022, 16 Pages.
"Non Final Office Action Issued in U.S. Appl. No. 17/197,650", dated Oct. 12, 2022, 19 Pages.
"Non Final Office Action Issued in U.S. Appl. No. 17/197,684", dated Nov. 28, 2022, 14 Pages.
"Final Office Action Issued in U.S. Appl. No. 17/197,717", dated Jan. 20, 2023, 15 Pages.
"Non Final Office Action Issued in U.S. Appl. No. 17/197,740", dated Nov. 14, 2022, 23 Pages.
"Non Final Office Action Issued in U.S. Appl. No. 17/728,252", dated Oct. 12, 2022, 12 Pages.
"Notice of Allowance Issued in U.S. Appl. No. 17/728,252", dated Jan. 25, 2023, 9 Pages.
"Notice of Allowance Issued in U.S. Appl. No. 17/840,958", dated Nov. 23, 2022, 18 Pages.
Hsu, et al., "Unsupervised domain adaptation for robust speech recognition via variational autoencoder-based data augmentation", In Proceedings of IEEE Automatic Speech Recognition and Understanding Workshop, Dec. 16, 2017, pp. 16-23.
Mazalov, et al., "Microsoft Cognitive Toolkit (CNTK), An Open Source Deep-Learning Toolkit", Retrieved From: https://web.archive.org/web/20190112114726/https://github.com/microsoft/CNTK, Jan. 12, 2019, 10 Pages.
Nishizaki, Hiromitsu, "Data Augmentation and Feature Extraction using Variational Autoencoder for Acoustic Modeling", In Proceedings of Asia-Pacific Signal and Information Processing Association Annual Summit and Conference, Dec. 12, 2017, 6 Pages.
Park, et al., "SpecAugment: A Simple Data Augmentation Method for Automatic Speech Recognition", In Repository of arXiv:1904.08779v3, Dec. 3, 2019, 6 Pages.
Salamon, et al., "Deep Convolutional Neural Networks and Data Augmentation for Environmental Sound Classification", In Journal of IEEE Signal Processing Letters, vol. 24, Issue 3, Mar. 2017, pp. 279-283.
"Non Final Office Action Issued in U.S. Appl. No. 17/197,740", dated Aug. 7, 2023, 24 Pages.
Kim, et al., "Environmental Noise Embeddings for Robust Speech Recognition", In Repository of arXiv:1601.02553v2, Sep. 29, 2016, 5 Pages.
Madhu, et al., "Data Augmentation using Generative Adversarial Network for Environmental Sound Classification", In Proceedings of the 27th European Signal Processing Conference, Sep. 2, 2019, 5 Pages.
Mathur, et al., "Mic2mic: Using Cycle-Consistent Generative Adversarial Networks to Overcome Microphone Variability in Speech Systems", In Proceedings of the 18th International Conference on Information Processing in Sensor Networks, Apr. 16, 2019, pp. 169-180.
Nagano, et al., "Data Augmentation Based on Vowel Stretch for Improving Children's Speech Recognition", In Proceedings of the IEEE Automatic Speech Recognition and Understanding Workshop, Dec. 14, 2019, pp. 502-508.
"Final Office Action Issued in U.S. Appl. No. 17/197,684", dated May 15, 2023, 16 Pages.
"Final Office Action Issued in U.S. Appl. No. 17/197,650", dated Feb. 24, 2023, 15 Pages.
"Final Office Action Issued in U.S. Appl. No. 17/197,740", dated Mar. 9, 2023, 22 Pages.
Mathur, et al., "Using Deep Data Augmentation Training to Address Software and Hardware Heterogeneities in Wearable and Smartphone Sensing Devices", In Proceedings of the 17th ACM/IEEE International Conference on Information Processing in Sensor Networks, Apr. 11, 2018, pp. 200-211.
Sun, et al., "An Unsupervised Deep Domain Adaptation Approach For Robust Speech Recognition", In Journal of Neurocomputing, vol. 257, Feb. 7, 2017, pp. 79-87.
"Non Final Office Action Issued in U.S. Appl. No. 17/197,549", dated Sep. 6, 2023, 20 Pages.
"Non Final Office Action Issued In U.S. Appl. No. 17/197,684", dated Oct. 3, 2023, 19 Pages.
"Notice of Allowance Issued in U.S. Appl. No. 17/197,650", dated Oct. 23, 2023, 10 Pages.
"Non Final Office Action Issued in U.S. Appl. No. 17/197,650", dated Jun. 30, 2023, 17 Pages.
"Advisory Action Issued in U.S. Appl. No. 17/197,740", dated Jul. 3, 2023, 6 Pages.
Coleman, et al., "On Object-Based Audio with Reverberation", In Proceedings of the 60th International Conference on Dereverberation and Reverberation of Audio, Music, and Speech, Audio Engineering Society, Feb. 3, 2016, 10 Pages.
"Notice of Allowance Issued in U.S. Appl. No. 17/840,958", dated Nov. 1, 2023, 9 Pages.
"Final Office Action Issued in U.S. Appl. No. 17/197,740", dated Nov. 22, 2023, 25 Pages.
Non-Final Office Action mailed on Dec. 14, 2023, in U.S. Appl. No. 17/197,717, 21 pages.
Notice of Allowance mailed on Dec. 18, 2023, in U.S. Appl. No. 17/197,650, 4 pages.
Final Office Action mailed on Feb. 16, 2024, in U.S. Appl. No. 17/197,684, 21 pages.
Szoke, et al., "Building and evaluation of a real room impulse response dataset", IEEE Journal of Selected Topics in Signal Processing, vol. 13 no. 4, Aug. 2019, pp. 863-876.
U.S. Appl. No. 17/077,863, filed Oct. 22, 2020.
U.S. Appl. No. 17/840,958, filed Jun. 15, 2022.
U.S. Appl. No. 17/728,252, filed Apr. 25, 2022.
U.S. Appl. No. 17/077,965, filed Oct. 22, 2020.
U.S. Appl. No. 17/197,650, filed Mar. 10, 2021.
U.S. Appl. No. 17/197,717, filed Mar. 10, 2021.
U.S. Appl. No. 17/197,740, filed Mar. 10, 2021.
U.S. Appl. No. 17/197,549, filed Mar. 10, 2021.
U.S. Appl. No. 17/197,684, filed Mar. 10, 2021.
Supplementary European Search Report Received for European Application No. 21766972.0, mailed on Mar. 4, 2024, 8 pages.
Airaksinen, et al., "Data Augmentation Strategies for Neural Network F0 Estimation," ICASSP 2019 - 2019 IEEE International Conference on Acoustics, Speech and Signal Processing (ICASSP), Brighton, UK, 2019, pp. 6485-6489.
Final Office Action mailed on Feb. 6, 2024 in U.S. Appl. No. 17/197,549, (MS# 800587-US07) 22 Pages.

(56) References Cited

OTHER PUBLICATIONS

Extended European Search Report received for European Application No. 21768010.7, mailed on Apr. 9, 2024, 9 pages.

* cited by examiner

SYSTEM AND METHOD FOR DATA AUGMENTATION OF FEATURE-BASED VOICE DATA

RELATED APPLICATION(S)

This application claims the benefit of U.S. Provisional Application No. 62/988,337, filed on 11 Mar. 2020, the entire contents of which are incorporated herein by reference.

TECHNICAL FIELD

This disclosure relates to data augmentation and, more particularly, to systems and methods for data augmentation of feature-based voice data.

BACKGROUND

Data augmentation allows for the generation of new training data for any machine learning system by augmenting existing data to represent new conditions. For example, data augmentation has been used to improve robustness to noise and reverberation in various speech processing systems and applications, and other unpredictable characteristics of speech. Conventional approaches to augmenting voice-based include processing audio signals in the time domain with various data augmentations. However, processing these time domain signals may reveal sensitive or private details within the audio signals. As such, these audio signals may be processed in other domains to avoid exposing their content. Unfortunately, conventional data augmentation processes are unable to augment audio signals in other domains.

SUMMARY OF DISCLOSURE

In one implementation, a computer-implemented method is executed on a computing device and includes receiving feature-based voice data associated with a first acoustic domain. One or more gain-based augmentations may be performed on at least a portion of the feature-based voice data, thus defining gain-augmented feature-based voice data.

One or more of the following features may be included. A selection of a target acoustic domain may be received. Performing the one or more gain-based augmentations to the at least a portion of the feature-based voice data may include performing the one or more gain-based augmentations to the at least a portion of the feature-based voice data based upon, at least in part, the target acoustic domain. A distribution of gain levels associated with the target acoustic domain may be determined. Performing the one or more gain-based augmentations to the at least a portion of the feature-based voice data may include performing the one or more gain-based augmentations to the at least a portion of the feature-based voice data based upon, at least in part, the distribution of gain levels associated with the target acoustic domain. Performing the one or more gain-based augmentations to the at least a portion of the feature-based voice data may include amplifying at least a portion of the feature-based voice data. Performing the one or more gain-based augmentations to the at least a portion of the feature-based voice data may include attenuating at least a portion of the feature-based voice data.

In another implementation, a computer program product resides on a computer readable medium and has a plurality of instructions stored on it. When executed by a processor, the instructions cause the processor to perform operations including receiving feature-based voice data associated with a first acoustic domain. One or more gain-based augmentations may be performed on at least a portion of the feature-based voice data, thus defining gain-augmented feature-based voice data.

One or more of the following features may be included. A selection of a target acoustic domain may be received. Performing the one or more gain-based augmentations to the at least a portion of the feature-based voice data may include performing the one or more gain-based augmentations to the at least a portion of the feature-based voice data based upon, at least in part, the target acoustic domain. A distribution of gain levels associated with the target acoustic domain may be determined. Performing the one or more gain-based augmentations to the at least a portion of the feature-based voice data may include performing the one or more gain-based augmentations to the at least a portion of the feature-based voice data based upon, at least in part, the distribution of gain levels associated with the target acoustic domain. Performing the one or more gain-based augmentations to the at least a portion of the feature-based voice data may include amplifying at least a portion of the feature-based voice data. Performing the one or more gain-based augmentations to the at least a portion of the feature-based voice data may include attenuating at least a portion of the feature-based voice data.

In another implementation, a computing system includes at least one processor and at least one memory architecture coupled with the at least one processor. The at least one processor is configured to receive feature-based voice data associated with a first acoustic domain. The at least one processor is further configured to perform one or more gain-based augmentations on at least a portion of the feature-based voice data, thus defining gain-augmented feature-based voice data.

One or more of the following features may be included. A selection of a target acoustic domain may be received. Performing the one or more gain-based augmentations to the at least a portion of the feature-based voice data may include performing the one or more gain-based augmentations to the at least a portion of the feature-based voice data based upon, at least in part, the target acoustic domain. A distribution of gain levels associated with the target acoustic domain may be determined. Performing the one or more gain-based augmentations to the at least a portion of the feature-based voice data may include performing the one or more gain-based augmentations to the at least a portion of the feature-based voice data based upon, at least in part, the distribution of gain levels associated with the target acoustic domain. Performing the one or more gain-based augmentations to the at least a portion of the feature-based voice data may include amplifying at least a portion of the feature-based voice data. Performing the one or more gain-based augmentations to the at least a portion of the feature-based voice data may include attenuating at least a portion of the feature-based voice data.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
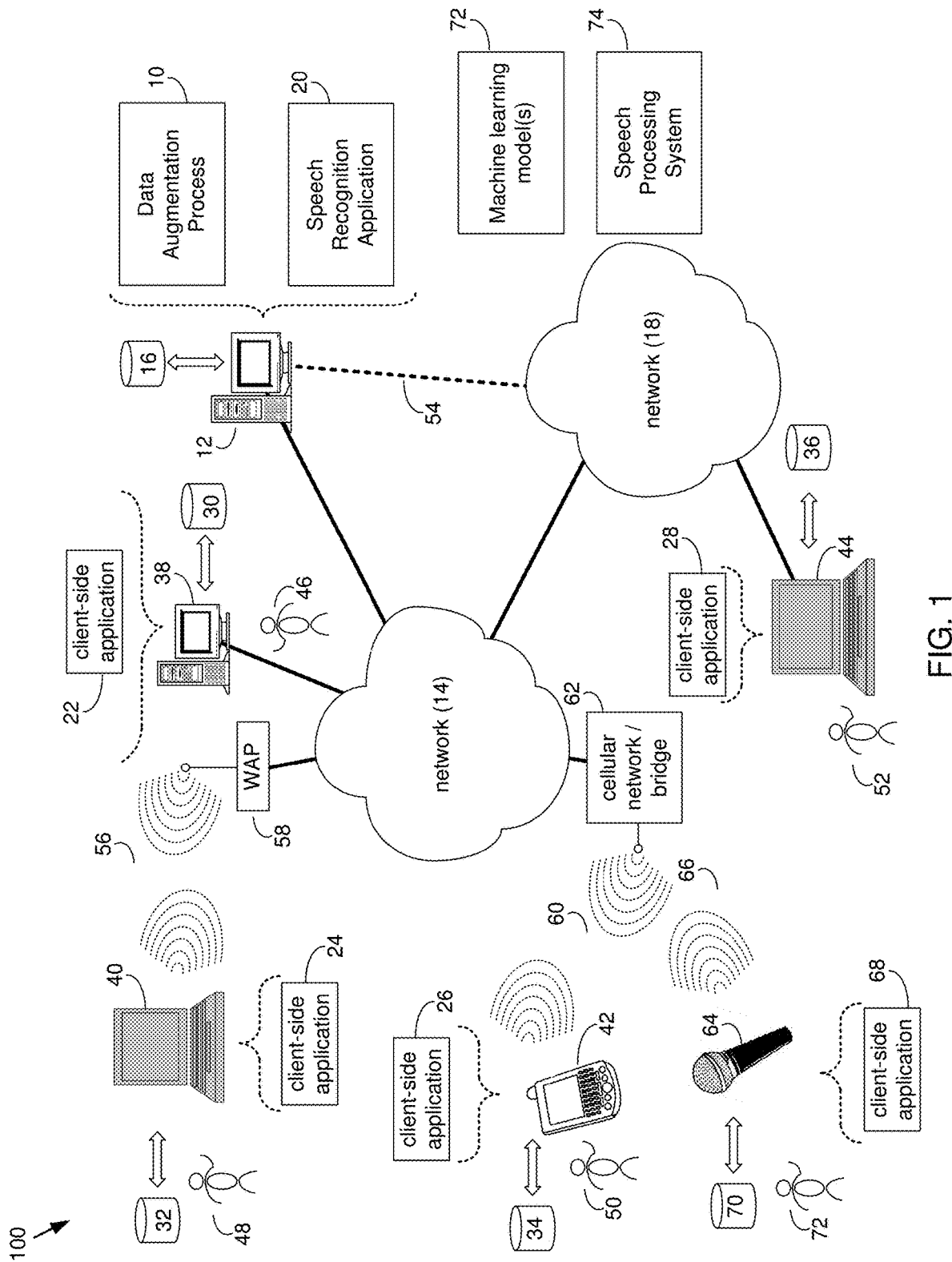
FIG. 1 is a diagrammatic view of a data augmentation process and an speech processing process coupled to a distributed computing network.
Figure 2:
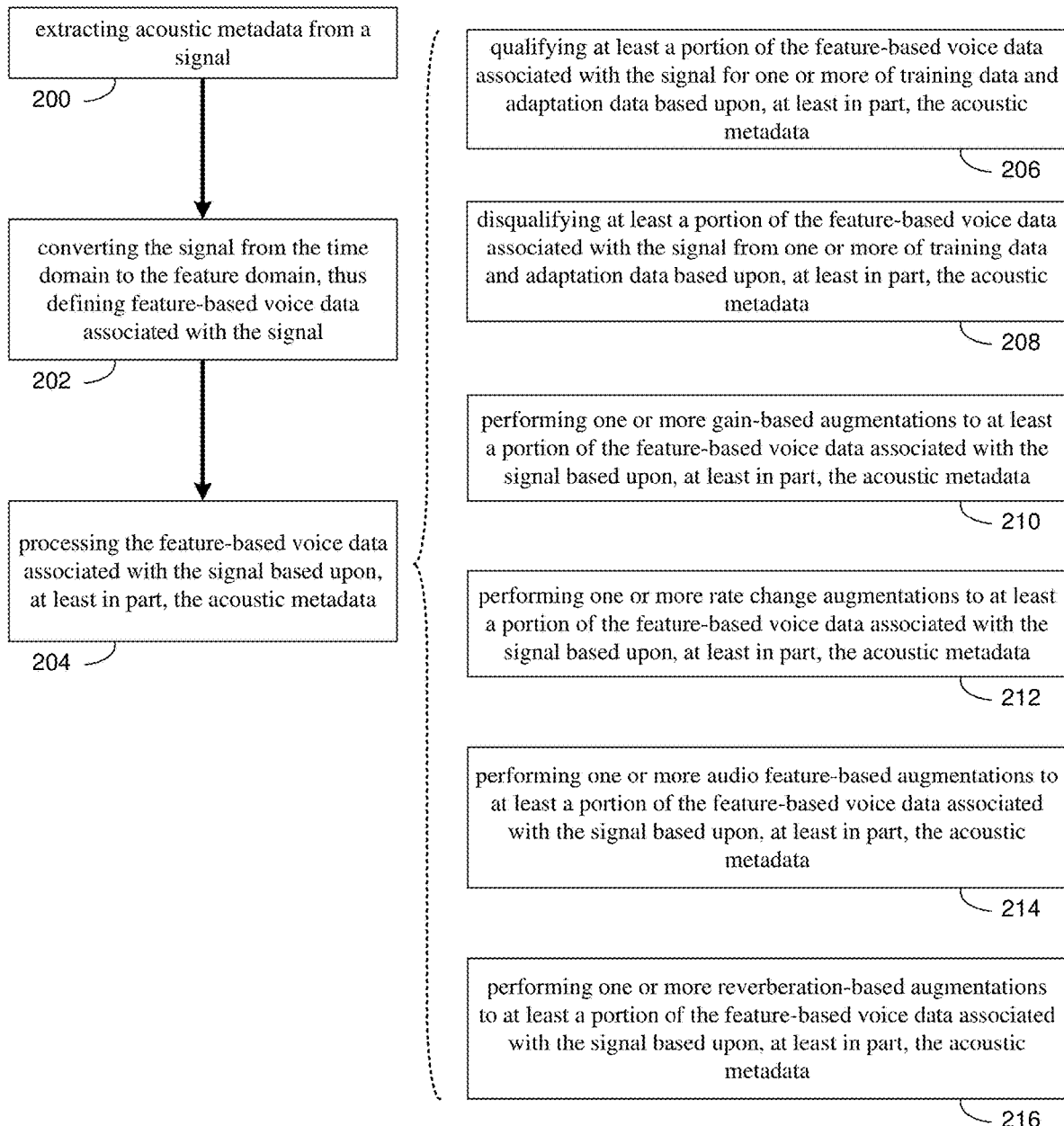
FIG. 2 is a flow chart of one implementation of the data augmentation process of FIG. 1.

Referring now to FIG. 1, there is shown data augmentation process 10 that may reside on and may be executed by a computing device 12, which may be connected to a network (e.g., network 14) (e.g., the internet or a local area network). Examples of computing device 12 (and/or one or more of the client electronic devices noted below) may include, but are not limited to, a personal computer(s), a laptop computer(s), mobile computing device(s), a server computer, a series of server computers, a mainframe computer(s), or a computing cloud(s). Computing device 12 may execute an operating system, for example, but not limited to, Microsoft® Windows®; Mac® OS X®; Red Hat® Linux®, or a custom operating system. (Microsoft and Windows are registered trademarks of Microsoft Corporation in the United States, other countries or both; Mac and OS X are registered trademarks of Apple Inc. in the United States, other countries or both; Red Hat is a registered trademark of Red Hat Corporation in the United States, other countries or both; and Linux is a registered trademark of Linus Torvalds in the United States, other countries or both).

As will be discussed below in greater detail, a data augmentation process, such as data augmentation process 10 of FIG. 1, may extract acoustic metadata from a signal. The signal may be converted from the time domain to the feature domain, thus defining feature-based voice data associated with the signal. The feature-based voice data associated with the signal may be processed based upon, at least in part, the acoustic metadata.

The instruction sets and subroutines of data augmentation process 10, which may be stored on storage device 16 coupled to computing device 12, may be executed by one or more processors (not shown) and one or more memory architectures (not shown) included within computing device 12. Storage device 16 may include but is not limited to: a hard disk drive; a flash drive, a tape drive; an optical drive; a RAID array; a random access memory (RAM); and a read-only memory (ROM).

Network 14 may be connected to one or more secondary networks (e.g., network 18), examples of which may include but are not limited to: a local area network; a wide area network; or an intranet, for example.

Data augmentation process 10 may be a stand-alone application that interfaces with an applet/application that is accessed via client applications 22, 24, 26, 28, 66. In some embodiments, data augmentation process 10 may be, in whole or in part, distributed in a cloud computing topology. In this way, computing device 12 and storage device 16 may refer to multiple devices, which may also be distributed throughout network 14 and/or network 18.

Computing device 12 may execute a speech recognition application (e.g., speech recognition application 20), examples of which may include, but are not limited to, automated speech recognition (ASR) programs and applications, speech-to-text (SST) programs and applications, computer speech recognition programs and applications, voice recognition programs and applications, in-vehicle voice command programs and applications, etc. including those available from Nuance Communications, Inc. of Burlington, Mass. Data augmentation process 10 and/or speech recognition application 20 may be accessed via client applications 22, 24, 26, 28, 68. Data augmentation process 10 may be a stand-alone application, or may be an applet/application/script/extension that may interact with and/or be executed within speech recognition application 20, a component of speech recognition application 20, and/or one or more of client applications 22, 24, 26, 28, 68. Speech recognition application 20 may be a stand-alone application, or may be an applet/application/script/extension that may interact with and/or be executed within data augmentation process 10, a component of data augmentation process 10, and/or one or more of client applications 22, 24, 26, 28, 68. One or more of client applications 22, 24, 26, 28, 68 may be a stand-alone application, or may be an applet/application/script/extension that may interact with and/or be executed within and/or be a component of data augmentation process 10 and/or speech recognition application 20. Examples of client applications 22, 24, 26, 28, 68 may include, but are not limited to, applications that receive queries to search for content from one or more databases, servers, cloud storage servers, etc., a textual and/or a graphical user interface, a customized web browser, a plugin, an Application Programming Interface (API), or a custom application. The instruction sets and subroutines of client applications 22, 24, 26, 28, 68 which may be stored on storage devices 30, 32, 34, 36, coupled to client electronic devices 38, 40, 42, 44 may be executed by one or more processors (not shown) and one or more memory architectures (not shown) incorporated into client electronic devices 38, 40, 42, 44.

Storage devices 30, 32, 34, 36, may include but are not limited to: hard disk drives; flash drives, tape drives; optical drives; RAID arrays; random access memories (RAM); and read-only memories (ROM). Examples of client electronic devices 38, 40, 42, 44 (and/or computing device 12) may include, but are not limited to, a personal computer (e.g., client electronic device 38), a laptop computer (e.g., client electronic device 40), a smart/data-enabled, cellular phone (e.g., client electronic device 42), a notebook computer (e.g., client electronic device 44), a tablet (not shown), a server (not shown), a television (not shown), a smart television (not shown), a media (e.g., video, photo, etc.) capturing device (not shown), and a dedicated network device (not shown). Client electronic devices 38, 40, 42, 44 may each execute an operating system, examples of which may include but are not limited to, Microsoft® Windows®; Mac® OS X®; Red Hat® Linux®, Windows® Mobile, Chrome OS, Blackberry OS, Fire OS, or a custom operating system.

One or more of client applications 22, 24, 26, 28, 68 may be configured to effectuate some or all of the functionality of data augmentation process 10 (and vice versa). Accordingly, data augmentation process 10 may be a purely server-side application, a purely client-side application, or a hybrid server-side/client-side application that is cooperatively executed by one or more of client applications 22, 24, 26, 28, 68 and/or data augmentation process 10.

One or more of client applications 22, 24, 26, 28, 68 may be configured to effectuate some or all of the functionality of speech recognition application 20 (and vice versa). Accordingly, speech recognition application 20 may be a purely server-side application, a purely client-side application, or a hybrid server-side/client-side application that is cooperatively executed by one or more of client applications 22, 24, 26, 28, 68 and/or speech recognition application 20. As one or more of client applications 22, 24, 26, 28, 68 data augmentation process 10, and speech recognition application 20, taken singly or in any combination, may effectuate some or all of the same functionality, any description of effectuating such functionality via one or more of client applications 22, 24, 26, 28, 68, data augmentation process 10, speech recognition application 20, or combination thereof, and any described interaction(s) between one or more of client applications 22, 24, 26, 28, 68 data augmentation process 10, speech recognition application 20, or combination thereof to effectuate such functionality, should be taken as an example only and not to limit the scope of the disclosure.

Users 46, 48, 50, 52 may access computing device 12 and data augmentation process 10 (e.g., using one or more of client electronic devices 38, 40, 42, 44) directly or indirectly through network 14 or through secondary network 18. Further, computing device 12 may be connected to network 14 through secondary network 18, as illustrated with phantom link line 54. Data augmentation process 10 may include one or more user interfaces, such as browsers and textual or graphical user interfaces, through which users 46, 48, 50, 52 may access data augmentation process 10.

The various client electronic devices may be directly or indirectly coupled to network 14 (or network 18). For example, client electronic device 38 is shown directly coupled to network 14 via a hardwired network connection. Further, client electronic device 44 is shown directly coupled to network 18 via a hardwired network connection.

Client electronic device 40 is shown wirelessly coupled to network 14 via wireless communication channel 56 established between client electronic device 40 and wireless access point (i.e., WAP) 58, which is shown directly coupled to network 14. WAP 58 may be, for example, an IEEE 800.11a, 800.11b, 800.11g, Wi-Fi®, and/or Bluetooth™ (including Bluetooth™ Low Energy) device that is capable of establishing wireless communication channel 56 between client electronic device 40 and WAP 58. Client electronic device 42 is shown wirelessly coupled to network 14 via wireless communication channel 60 established between client electronic device 42 and cellular network/bridge 62, which is shown directly coupled to network 14. In some implementations, audio recording device 64 may be wirelessly coupled to network 14 via wireless communication channel 66 established between client electronic device 42 and cellular network/bridge 62, which is shown directly coupled to network 14. Storage device 70 may be coupled to audio recording system 64 and may include but is not limited to: hard disk drives; flash drives, tape drives; optical drives; RAID arrays; random access memories (RAM); and read-only memories (ROM). User 72 may access computing device 12 and data augmentation process 10 (e.g., using one or more of audio recording system 64) directly or indirectly through network 14 or through secondary network 18.

Some or all of the IEEE 800.11x specifications may use Ethernet protocol and carrier sense multiple access with collision avoidance (i.e., CSMA/CA) for path sharing. The various 800.11x specifications may use phase-shift keying (i.e., PSK) modulation or complementary code keying (i.e., CCK) modulation, for example. Bluetooth™ (including Bluetooth™ Low Energy) is a telecommunications industry specification that allows, e.g., mobile phones, computers, smart phones, and other electronic devices to be interconnected using a short-range wireless connection. Other forms of interconnection (e.g., Near Field Communication (NFC)) may also be used.

The Data Augmentation Process:

In some implementations consistent with the present disclosure, systems and methods may be provided for data augmentation of feature-based voice data. As discussed above and in some implementations, data augmentation allows for the generation of new training data for a machine learning system by augmenting existing data to represent new conditions. For example, data augmentation has been used to improve robustness to noise and reverberation, and other unpredictable characteristics of speech in a real world deployment (e.g., issues and unpredictable characteristics when capturing speech signals in a real world environment versus a controlled environment). Conventional approaches to augmenting voice-based data include processing audio signals in the time domain with various data augmentations. However, processing these audio signals with data augmentations in the time domain may reveal sensitive or private details within the audio signals. As such, these audio signals may be processed in other domains to avoid exposing their content. Unfortunately, conventional data augmentation processes are unable to augment audio signals in other domains. For example and as will be discussed in greater detail below, data retention and privacy agreements and laws generally require the dashing (i.e., chunking of audio into small segments) and de-identifying (i.e., removal of personal information) of audio signals. Accordingly, with an audio signal that is converted to the feature domain, dashed, and de-identified, conventional data augmentation techniques are unable to augment the feature representation of the audio signal.

Feature-Based Voice Data Processing with Acoustic Metadata

As discussed above and referring also at least to FIGS. 2-17, data augmentation process 10 may extract 200 acoustic metadata from a signal. The signal may be converted 202 from the time domain to the feature domain, thus defining feature-based voice data associated with the signal. The feature-based voice data associated with the signal may be processed 204 based upon, at least in part, the acoustic metadata.

In some implementations, data augmentation process 10 may extract 200 acoustic metadata from a signal. Referring to the example of FIG. 3 and in some implementations, data augmentation process 10 may receive a signal (e.g., audio signal 300). In some implementations, the signal (e.g., audio signal 300) may be an audio recording (e.g., received from or captured by an audio recording system (e.g., audio recording system 64)). In some implementations, audio signal 300 may include speech components and/or noise components. For example, audio signal 300 may be a recording of a speaker's interaction with a virtual assistant. In this example, suppose the speaker asks the virtual assistant to check the weather tomorrow and that audio signal 300 is recorded using the speaker's smartphone; specifically the smartphone's speakerphone while the speaker is driving in a vehicle on the highway. Accordingly, audio signal 300 may include speech components from the speaker; noise components from the vehicle; reverberation (or lack thereof) resulting from the vehicle interior; and other acoustic characteristics associated with audio signal 300. In some implementations, it may be desirable to use audio signal 300 for training a speech processing system (e.g., an automated speech recognition (ASR) system, a voice biometric system, emotion detection system, medical symptom detection symptom, hearing enhancement system, etc.) by augmenting portions of audio signal 300.

However and as discussed above, performing these augmentations using conventional data augmentation techniques require processing and retaining the audio signal 300 in the time domain. When an audio signal is augmented in the time domain, the speech content of the audio signal is exposed. Returning to the above example, processing audio signal 300 in the time domain would expose the content of the speaker's conversation (e.g., the interaction with the speaker's virtual assistant regarding the weather). As will be discussed in greater detail below, data augmentation process 10 may convert 202 audio signal 300 from the time domain to the feature domain and process 204 the feature-based voice data associated with the signal in the feature domain without exposing the speech content of signal 300.

In some implementations, data augmentation process 10 may extract 200 acoustic metadata from the audio signal before converting 202 the audio signal from the time domain to the feature domain. Acoustic metadata may generally refer to information regarding the characteristics or properties of the signal. In some implementations, the acoustic metadata may only refer to properties of the signal without exposing or describing any speech content of the signal. Referring again to FIG. 3 and in some implementations, data augmentation process 10 may extract global acoustic metadata for the signal and/or for portions of the signal specifically. Global acoustic metadata may include properties or characteristics of a signal generally. For example and continuing with the above example of audio signal 300, data augmentation process 10 may extract global acoustic metadata for audio signal 300 generally (e.g., global acoustic metadata 302 associated with audio signal 300). In this example, data augmentation process 10 may extract 200 global acoustic metadata 302 indicative of a noise component throughout the entirety of audio signal 300 (e.g., noise associated with the vehicle travelling down the highway while a speaker is interacting with the virtual assistant). While an example of a constant noise component has been provided for global acoustic metadata 302, it will be appreciated that any property or characteristic concerning the audio signal generally may be extracted as global acoustic metadata 302 within the scope of the present disclosure. For example, global acoustic metadata may include information associated with the acoustic domain(s) the audio signal is recorded in, the number of speakers identifiable in the audio signal, whether the audio signal includes speech and/or noise, the type of audio recording equipment used to capture the audio signal, etc.

In some implementations, data augmentation process 10 may extract 200 acoustic metadata associated with specific portions of an audio signal. Referring again to the example of FIG. 3 and continuing with the above example, data augmentation process 10 may divide audio signal into a plurality of portions or frames. In some implementations, the size of each portion or frame may represent a threshold percentage of audio signal 300, a threshold duration of audio signal 300, a threshold amount of data from audio signal 300, etc. In this manner, audio signal 300 may be divided into any number of portions within the scope of the present disclosure. In some implementations, data augmentation process 10 may divide the signal into any number of portions of varying sizes and/or of the same size within the scope of the present disclosure.

Figure 3:
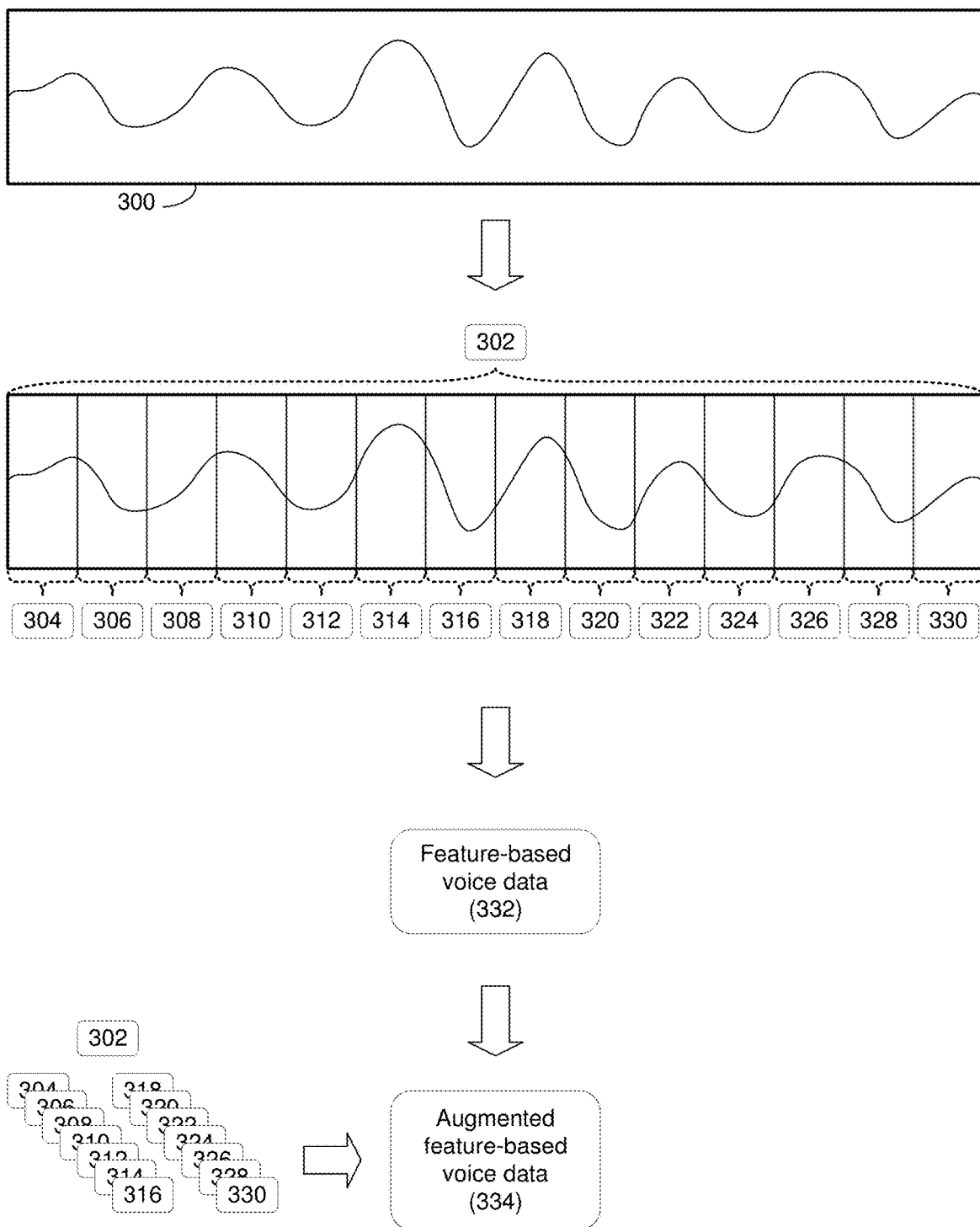
FIG. 3 is a diagrammatic view of the extraction of acoustic metadata from an audio signal according to one implementation of the data augmentation process of FIG. 1.

As shown in the example of FIG. 3, data augmentation process 10 may divide audio signal into e.g., 14 sections or portions and may extract 200 acoustic metadata from each portion (e.g., acoustic metadata 304, 306, 308, 310, 312, 314, 316, 318, 320, 322, 324, 326, 328, 330). In some implementations, data augmentation process 10 may extract 200 acoustic metadata from at least one of the defined portions of audio signal 300. In one example, acoustic metadata 304, 306, 308, 310, 326, 328, 330 may indicate the presence of a speech component while acoustic metadata 312, 314, 316, 318, 320, 322, 324 may indicate a lack of a speech component. While an example of acoustic metadata indicative of the presence or absence of a speech component has been described, it will be appreciated that any acoustic metadata specific to a particular portion of audio signal 300 may be extracted 200 within the scope of the present disclosure. In some implementations, data augmentation process 10 may store the extracted acoustic metadata (e.g., acoustic metadata 302, 304, 306, 308, 310, 312, 314, 316, 318, 320, 322, 324, 326, 328, 330) in a memory buffer or other storage device (e.g., storage device 16). As will be discussed in greater detail below, acoustic metadata extracted from a signal may be used for processing the signal when the signal has been converted into the feature domain.

In some implementations, data augmentation process 10 may convert 202 the signal from the time domain to the feature domain, thus defining feature-based voice data associated with the signal. Referring again to the example of FIG. 3 and in some implementations, data augmentation process 10 may convert 202 audio signal 300 from the time domain to the feature domain, thus defining feature-based voice data associated with audio signal 300 (e.g., feature-based voice data 332). As is known in the art, the feature domain may generally include a feature representation of data (e.g., the frequency domain, the Mel-frequency domain, the Mel Filter Bank domain, etc.). In some implementations, audio signals may be recorded or captured in the time domain (e.g., as a function of amplitude of the signal over time) with various acoustic properties (e.g., speech components, noise components, reverberation, etc.) stored within the signal. As is known in the art, by converting the audio signal to another domain (e.g., the frequency domain, the modulation domain, the Mel-frequency domain, etc.), speech processing systems may be able to process the speech to perform various functions that are not possible in the time domain and/or are more efficient when processed in another domain.

In some implementations, data augmentation process 10 may convert 202 the signal from the time domain to the feature domain by obtaining frequency components from the signal. In some implementations, data augmentation process 10 may obtain the frequency components from the signal by applying a Short-Time Fourier Transform (STFT) to the signal. While a STFT is discussed as a way of obtaining frequency components from the signal, it will be appreciated that other transformations may be used to derive the frequency components from the signal within the scope of the present disclosure. Applying a STFT to a signal may include applying overlapped framing with an analysis window. For example, audio signal 300 may be recorded as a time waveform in the time domain. Data augmentation process 10 may convert the time waveform of audio signal 300 into a sequence of short excerpts or frames (e.g., 20 milliseconds) of the time waveform. Data augmentation process 10 may convert each of the short excerpts to the frequency domain by applying a Fourier transform in combination with a window function, where such window functions are known in the art. Additionally, one or more band-pass filters may be applied and the received speech signal may be converted by data augmentation process 10 to a plurality of speech signals for a plurality of frequency bands. The frequency bands or frequency bins from the Fourier transform may be combined with the time windows to form a plurality of time frequency spectrum cells. The power or amplitude of the speech signals may be defined relative to time and frequency in each the time frequency spectrum cells, thus defining a power spectrum.

In one example, data augmentation process 10 may convert 202 the signal from the time domain to the Mel Filter Bank (MFB) domain. As is known in the art, converting 202 a signal to the Mel Filter Bank domain includes computing filter banks by applying triangular filters on a Mel-scale to the power spectrum discussed above. In this manner, a signal converted to the Mel Filter Bank domain may include a spectrogram as a function of frequency and time that emphasizes the non-linear human ear perception of sound. As is known in the art, a signal may be defined in the Mel Filter Bank domain as a plurality of filter banks and filter bank coefficients. In some implementations, to balance the spectrum and improve the signal-to-noise ratio (SNR), data augmentation process 10 may subtract the mean of each coefficient from all frames of the filter banks to yield mean-normalized filter banks. In some implementations, these mean values may be stored for reference. In this example, feature-based voice data 332 may include the filter banks and/or filter bank coefficients of the signal in the Mel Filter Bank domain.

In another example, data augmentation process 10 may convert 202 the signal from the time domain to the Mel-Frequency Cepstral (MFC) domain by computing the Mel-Frequency cepstral coefficients (MFCC) for the signal. As is known in the art, converting a signal to the Mel-Frequency Cepstral domain includes applying a Discrete Cosine Transform (DCT) to de-correlate the filter bank coefficients as discussed above to yield a compressed representation of the filter banks. The Mel-Frequency cepstral coefficients may include the amplitudes of the resulting spectrum. In this example, feature-based voice data 332 may include the Mel-Frequency cepstral coefficients of the signal in the Mel-Frequency Cepstral domain.

While examples of particular feature domains (e.g., feature-based representations of data) have been described, it will be appreciated that data augmentation process 10 may convert 202 the signal from the time domain to any feature domain within the scope of the present disclosure.

In some implementations, data augmentation process 10 may partition or dash a signal to avoid the speech content of the signal from being accessed after converting 202 to the feature domain. For example, data augmentation process 10 may chunk audio signal 300 into a plurality of portions and de-identify the portions. These portions may then be stored in a distributed manner without any information linking the various portions together. In this manner, the speech content of audio signal 300 may be kept private while still allowing access to a feature-based representation (e.g., feature-based voice data 332) of audio signal 300. As will be discussed in greater detail below, without accessing the complete or a large portion of an audio signal, conventional data augmentation techniques are unable to augment feature-based voice data. For example and as discussed above, when audio signals are dashed and de-identified, conventional data augmentation techniques are unable to augment the feature domain representation of these dashed and de-identified portions of the audio signal.

In some implementations, data augmentation process 10 may process 204 the feature-based voice data associated with the signal based upon, at least in part, the acoustic metadata. As discussed above and in some implementations, conventional data augmentation techniques are unable to augment an audio signal without processing the audio signal in the time domain and, as such, exposing the speech content of the audio signal. Accordingly, data augmentation process 10 may process 204 the feature-based voice data associated with the signal (e.g., the feature domain representation of the signal) by augmenting the feature-based voice data. As discussed above, data augmentation may generally include the process of modifying various characteristics of a particular portion of data. In some implementations, augmented data may help train or adapt machine learning models and artificial intelligence systems to be more robust to certain acoustic changes. For example, an automated speech recognition (ASR) system may be trained with speech signals captured in a noise-free acoustic domain or environment. However, when the ASR system attempts to process speech signals captured in an acoustic domain with noise, the ASR system may be less effective because of the added noise. In some implementations, data augmentation process 10 may augment existing data (e.g., audio signals) to train speech processing systems to be more robust to these changes and/or to adapt to different acoustic domains. In another example, a part of a speech processing system or model may be adapted with new adaptation data. Accordingly, data augmentation process 10 may process 204 the feature-based voice data associated with the signal to augment data that may adapt speech processing systems with new adaptation data.

In some implementations and as will be discussed below, when a signal is converted 202 from the time domain to the feature domain, it may not be possible to determine the acoustic properties or characteristics of the signal without converting the signal back into the time domain. Accordingly, data augmentation process 10 may utilize the extracted acoustic metadata to process 204 the feature-based voice data associated with a signal without converting the signal back into the time domain. In this manner, data augmentation process 10 may process 204 feature-based voice data associated with the signal without exposing speech content within the signal.

In some implementations, processing 204 the feature-based voice data associated with the signal based upon, at least in part, the acoustic metadata may include qualifying 206 at least a portion of the feature-based voice data associated with the signal for one or more of training data and adaptation data based upon, at least in part, the acoustic metadata. For example, data augmentation process 10 may utilize the acoustic metadata to qualify feature-based voice data for various purposes (e.g., for training a speech processing system, for augmenting the feature-based voice data, etc.). In some implementations, data augmentation process 10 may receive various constraints to qualify the feature-based voice data for processing. In one example, data augmentation process 10 may receive one or more constraints associated with processing 204 feature-based voice data. Data augmentation process 10 may compare the one or more constraints to the extracted acoustic metadata associated with the signal to determine whether feature-based voice data associated with the signal is qualified for a particular task (e.g., training a speech processing system, adapting a part of speech processing system with new adaptation data, augmenting the feature-based voice data, etc.).

Returning to the above example, suppose feature-based voice data 332 is the feature domain representation of audio signal 300 recording a user's interaction with a virtual assistant. In this example, suppose a speech processing system is only initially trained to process speech signals with a user speaking directly into the microphone of a telephone. In some implementations, the speech processing system may be trained to process speech signals in other acoustic domains. In this example, data augmentation process 10 may receive one or more constraints associated with processing feature-based voice data to determine whether the speech processing system can or should be trained with feature-based voice data 332. Data augmentation process 10 may utilize acoustic metadata 302, 304, 306, 308, 310, 312, 314, 316, 318, 320, 322, 324, 326, 328, 330 to qualify 206 feature-based voice data 332 for training the speech processing system based upon, at least in part, the one or more constraints received.

In some implementations, processing 204 the feature-based voice data associated with the signal based upon, at least in part, the acoustic metadata may include disqualifying 208 at least a portion of the feature-based voice data associated with the signal from one or more of training data and adaptation data based upon, at least in part, the acoustic metadata. Continuing with the above example, suppose that the audio signal 300 includes a recording of a portion of a telephone call. In this example, suppose that the first half of the meeting has no speech (e.g., silence). In this example, data augmentation process 10 may extract acoustic metadata 304, 306, 308, 310, 312, 314, 316 for portions of audio signal 300 that do not include any speech component and acoustic metadata 318, 320, 322, 324, 326, 328, 330 for portions of audio signal 300 that do include a speech component. Data augmentation process 10 may process 204 feature-based voice data 332 with acoustic metadata 302, 304, 306, 308, 310, 312, 314, 316, 318, 320, 322, 324, 326, 328, 330. Suppose that data augmentation process 10 receives one or more constraints for e.g., augmenting feature-based voice data to train a speech processing system to process speech signals in a noisy environment. In this example, data augmentation process 10 may utilize acoustic metadata 304, 306, 308, 310, 312, 314, 316 to disqualify 208 portions of feature-based voice data 332 that do not include a speech component and may utilize acoustic metadata 318, 320, 322, 324, 326, 328, 330 to qualify 206 other portions of feature-based voice data 332 for training and/or adapting the speech processing system.

While examples have been provided for qualifying and disqualifying portions of feature-based voice data 332 for training purposes, it will be appreciated that data augmentation process 10 may utilize acoustic metadata to qualify and/or disqualify portions of feature-based voice data for other purposes within the scope of the present disclosure.

Gain-Based Augmentations of Feature-Based Voice Data

Figure 4:
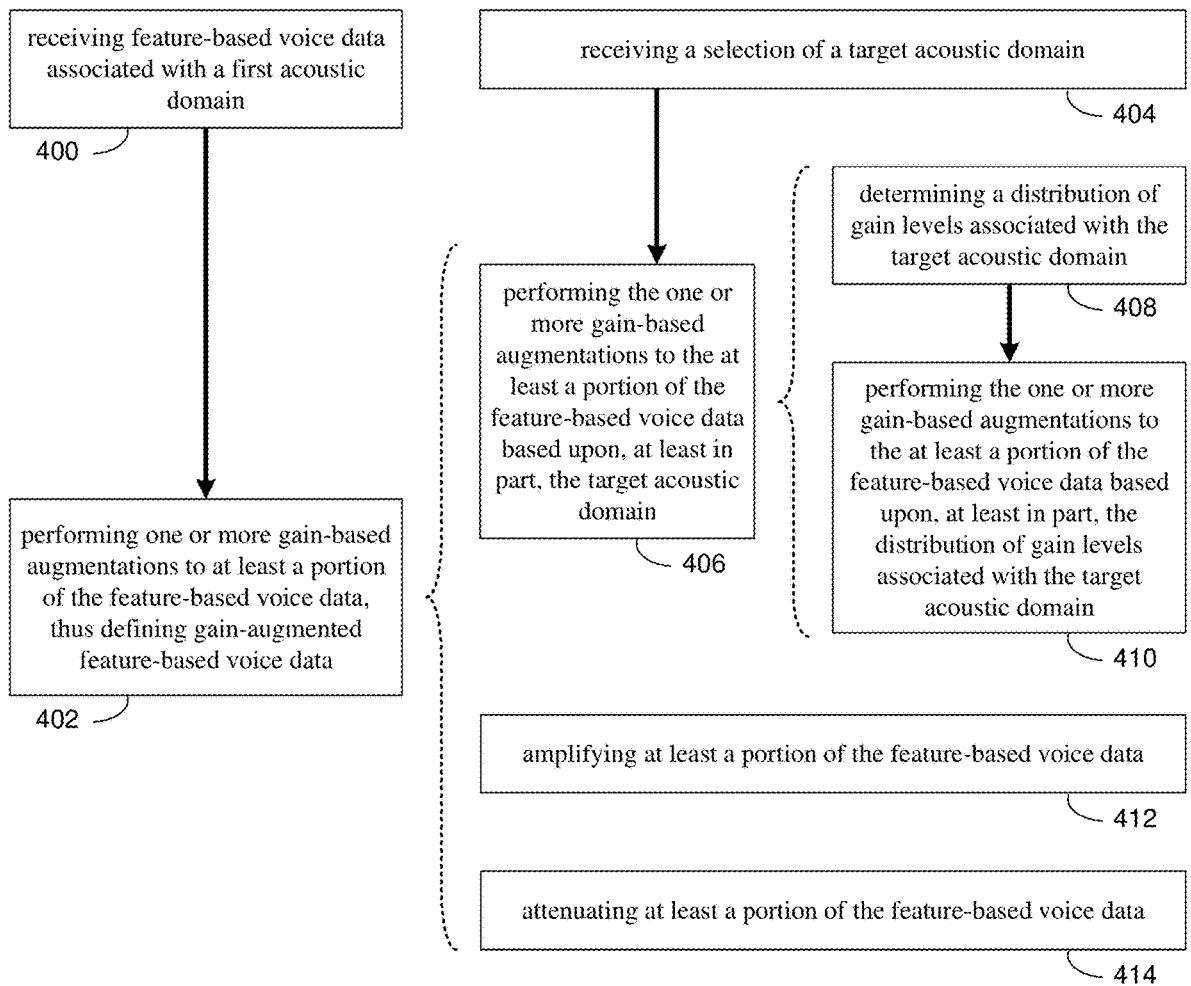
FIG. 4 is a flow chart of one implementation of the data augmentation process of FIG. 1.

Referring also to FIG. 4 and in some implementations, data augmentation process 10 may receive 400 feature-based voice data associated with a first acoustic domain. One or more gain-based augmentations may be performed 402 on at least a portion of the feature-based voice data, thus defining gain-augmented feature-based voice data. As will be discussed in greater detail below, a gain-based augmentation may generally include any change to a gain-based or gain-related property of the feature-based voice data. As is known in the art, gain may generally include a measurement of the amplification or attenuation of a signal.

In some implementations, data augmentation process 10 may receive 400 feature-based voice data associated with a first acoustic domain. As discussed above and in some implementations, feature-based voice data may be generated by converting a signal or at least a portion of a signal to the feature domain. Referring again to the example of FIG. 3 and in some implementations, data augmentation process 10 may receive 200 an audio signal (e.g., audio signal 300) and convert 202 the audio signal from the time domain to the feature domain to generate feature-based voice data (e.g., feature-based voice data 332) associated with the audio signal (e.g., audio signal 300). While an example has been provided of converting a signal from the time domain to the feature domain, it will be appreciated that a signal may be converted to the feature domain from any domain, within the scope of the present disclosure.

In some implementations, the feature-based voice data may be associated with a first acoustic domain. An acoustic domain may generally include the factors and characteristics that define the quality of a signal. For example, suppose a speaker is speaking into a receiver on a telephone in an enclosed office. In this example, the acoustic domain is defined by the receiving microphone in the telephone (i.e., signal processing characteristics of the microphone), the rate at which the speaker speaks, any noise within the enclosed office, the reverberation experienced within the enclosed office, etc. Now suppose the speaker switches to a speakerphone receiver on the telephone. In this example, while the environmental features remain the same (i.e., the enclosed office), the acoustic domain has changed because the speakerphone receiver represents different factors and characteristics that may impact the signal processing differently than the receiver on the telephone. In some implementations, the change in acoustic domain may have various impacts on the performance of a speech processing system. Accordingly, data augmentation process 10 may allow feature-based voice data from one acoustic domain to be used in the training of speech processing systems in other acoustic domains and/or for adapting a speech processing system or model with new adaptation data.

Figure 5:
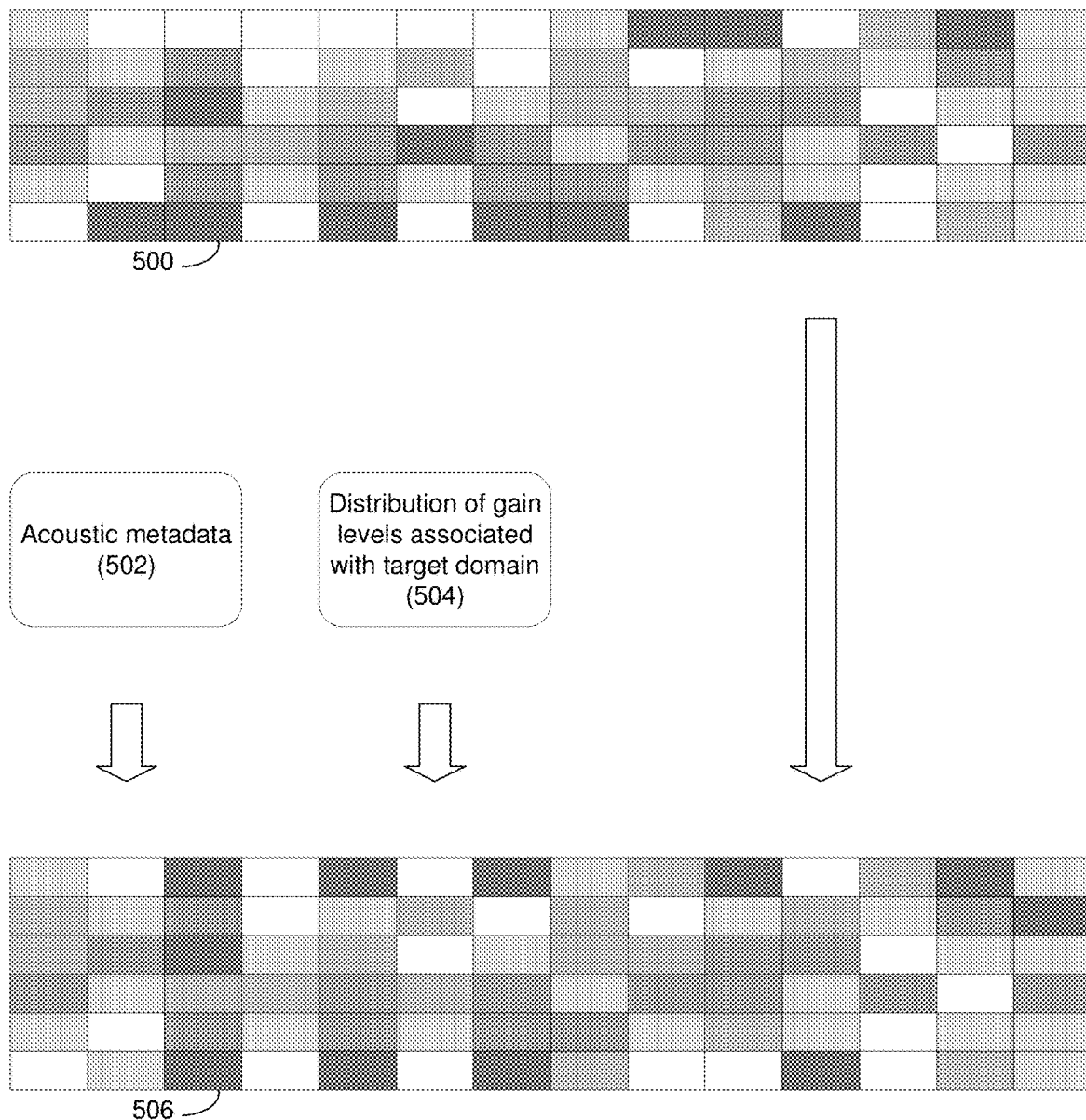
FIG. 5 is a diagrammatic view of one or more gain-based augmentations performed on feature-based voice data according to one implementation of the data augmentation process of FIG. 1.

In some implementations, data augmentation process 10 may perform 402 one or more gain-based augmentations on at least a portion of the feature-based voice data, thus defining gain-augmented feature-based voice data. Referring also to the example of FIG. 5 and in some implementations, data augmentation process 10 may receive 400 feature-based voice data (e.g., feature-based voice data 500) associated with a first acoustic domain. In the example of FIG. 5, feature-based voice data 500 may include a plurality of feature coefficients (e.g., Mel Filter Bank coefficients, Mel-frequency cepstral coefficients, etc.) represented as a spectrogram of a signal as a function of frequency (on the vertical axis) and time (on the horizontal axis) where the shade of each quadrant represents the amplitude of each feature coefficient. While one example of feature-based voice data has been described, it will be appreciated that the feature-based voice data may be represented in various ways within the scope of the present disclosure.

In this example, data augmentation process 10 may perform 402 one or more gain-based augmentations on at least a portion of the feature-based voice data associated with the first acoustic domain. As will be discussed in greater detail below, it may be desirable to augment at least a portion of feature-based voice data associated with a particular acoustic domain for various reasons. For example and in some implementations, data augmentation process 10 may perform 402 one or more gain-based augmentations on at least a portion of the feature-based voice data to utilize the feature-based voice data for training a speech processing system in a target acoustic domain. In this example, data augmentation process 10 may train a speech processing system with feature-based voice data from a different acoustic domain which may allow for speech processing systems to be effectively utilized in various acoustic domains using an augmented set of training feature-based voice data.

In another example, data augmentation process 10 may perform 402 one or more gain-based augmentations on at least a portion of the feature-based voice data to generate additional training data for speech processing systems with varying levels of gain. In this manner, data augmentation process 10 may train speech processing systems to be more robust against variations in gain by augmenting a set of training feature-based voice data with various gain levels. While two examples have been provided for utilizing gain-augmented feature-based voice data, it will be appreciated that data augmentation process 10 may perform 402 gain-based augmentations on feature-based voice data for various other purposes within the scope of the present disclosure. For example and in some implementations, gain-based augmentations may be used to adapt a speech processing system with new adaptation data (e.g., gain-based augmentations).

As discussed above, after a signal is converted to the feature domain, it may be impossible to determine certain acoustic properties of the signal without converting the signal back to the time domain. In some implementations, when receiving 400 the feature-based voice data, data augmentation process 10 may also receive information associated with the feature-based voice data from an external source (e.g., a user interface, a database, etc.). In some implementations, the information associated with the feature-based voice data may include information about the feature-based voice data generally. For example, the information may identify the feature-based voice data as being recorded in a general acoustic domain (e.g., vehicle noises).

In some implementations, the information associated with the feature-based voice data may or may not be specific to the feature-based voice data. For example, the information may provide general characteristics associated with the feature-based voice data (e.g., signals with vehicle noise typically have a particular gain level distribution).

In some implementations, processing 204 the feature-based voice data associated with the signal based upon, at least in part, the acoustic metadata may include performing 210 one or more gain-based augmentations on at least a portion of the feature-based voice data associated with the signal based upon, at least in part, the acoustic metadata. As discussed above, data augmentation process 10 may extract 200 acoustic metadata from a signal before the signal is converted 204 to the feature domain. As discussed above, the extracted acoustic metadata may include global acoustic metadata associated with the signal generally and/or acoustic metadata associated with or specific to particular portions of the signal. In this manner, the extracted acoustic metadata may provide more specific information about the acoustic domain of the feature-based voice data than available from other more generalized information about the feature-based voice data. As will be discussed in greater detail below and in some implementations, acoustic metadata associated with a signal may allow data augmentation process 10 to determine various characteristics of the feature-based voice data and perform 402 one or more gain-based augmentations on at least a portion of the feature-based voice data associated with the signal based upon, at least in part, the acoustic metadata.

In some implementations, data augmentation process 10 may receive 404 a selection of a target acoustic domain. A target acoustic domain may include a target set of factors and characteristics that define the quality of a signal. In some implementations, data augmentation process 10 may receive 404 a selection of a target acoustic domain by providing particular gain-based characteristics associated with the target acoustic domain. In some implementations, data augmentation process 10 may utilize a graphical user interface for receiving 404 a selection of a target acoustic domain from a library of predefined acoustic domains. In one example, data augmentations process 10 may receive selections (e.g., via a graphical user interface) of various characteristics of the acoustic domain (e.g., a selection of the reverberation, signal-to-noise ratio (SNR), a type of microphone array, a particular noise track, etc.) to define a target acoustic domain. As will be discussed in greater detail below and in some implementations, data augmentation process 10 may receive a range or distribution of characteristics for the target acoustic domain. While an example of a graphical user interface has been described, it will be appreciated that a target acoustic domain may be selected in various ways within the scope of the present disclosure (e.g., manually by a user, automatically by data augmentation process 10, a pre-defined target acoustic domain, etc.).

Figure 6:
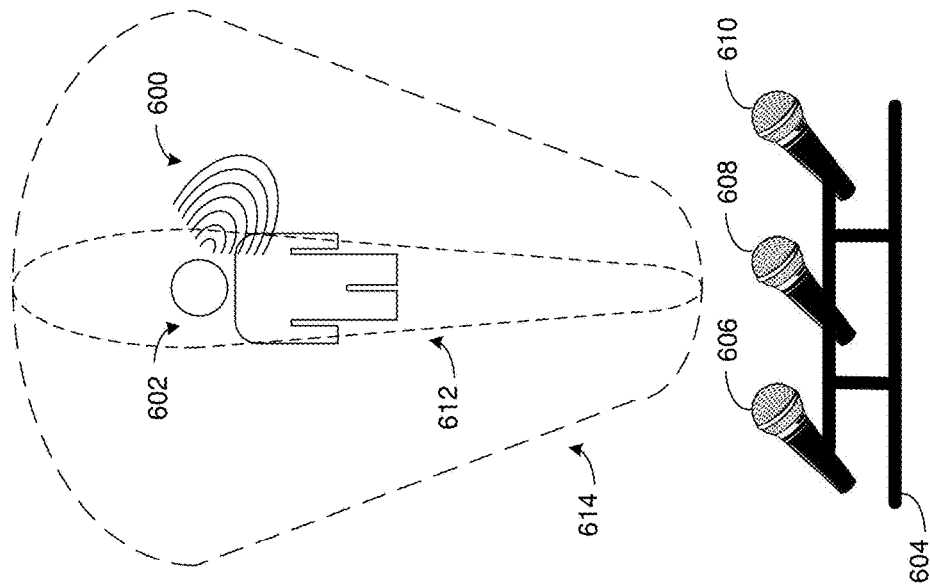
FIG. 6 is a diagrammatic view of a microphone array deployed in an acoustic domain while a speaker is speaking according to one implementation of the data augmentation process of FIG. 1.

Referring also to the example of FIG. 6 and in some implementations, suppose a speech processing system is trained for processing data in a particular acoustic domain (e.g., processing speech (e.g., speech signal 600) in a laboratory where the speaker (e.g., speaker 602) is speaking directly into a microphone (e.g., microphone array 604 of microphone elements 606, 608, 610)). In this example, because speaker 602 is speaking directly into microphone 604, the feature-based voice data or training feature-based voice data associated with speech signal 600 may have little attenuation (i.e., a high signal amplitude). However, suppose that speaker 602's head turns one way or another while speaking. In this example, the higher frequency signal components (e.g., represented by beampattern 612) of speech signal 600 may be more attenuated relative to the lower frequency signal components (e.g., represented by beampattern 614). In this example, movement of the speaker's head may introduce spectral variations to the signal that may impact the operation of a speech processing system trained with feature-based voice data associated with speaker 602 speaking directly into microphone array 604. In this example, data augmentation process 10 may receive 404 a selection of the acoustic domain associated with the speaker's head moving as the target acoustic domain. While an example of a particular target acoustic domain has been provided, it will be appreciated that various target acoustic domains may be selected within the scope of the present disclosure.

In some implementations, performing 402 the one or more gain-based augmentations to the at least a portion of the feature-based voice data may include performing 406 the one or more gain-based augmentations to the at least a portion of the feature-based voice data based upon, at least in part, the target acoustic domain. Returning to the above example, suppose data augmentation process 10 receives 404 a selection of the acoustic domain associated with a speaker's head moving while speaking in a laboratory. In this example, data augmentation process 10 may perform 406 one or more gain-based augmentations on at least a portion of the feature-based voice data of the first acoustic domain (e.g., the acoustic domain associated with a speaker speaking directly into a microphone within a laboratory (e.g., as shown in FIG. 6)).

In some implementations, data augmentation process 10 may perform 406 one or more gain-based augmentations on at least a portion of feature-based voice data 500 to account for a speaker's head movements while speaking. Accordingly, data augmentation process 10 may perform 406 these gain-based augmentations to map feature-based voice data 500 from the first acoustic domain (e.g., the acoustic domain associated with a speaker speaking directly into a microphone within a laboratory) to a target acoustic domain (e.g., the acoustic domain associated with a speaker's head turning while speaking within the laboratory). In this manner, a speech processing system may be trained using feature-based voice data augmented from one acoustic domain for processing speech in another acoustic domain.

As discussed above and in some implementations, performing 210 one or more gain-based augmentations on at least a portion of the feature-based voice data associated with the signal based upon, at least in part, the acoustic metadata. For example, data augmentation process 10 may extract 200 acoustic metadata (e.g., acoustic metadata 502) associated with feature-based voice data 500. As discussed above, acoustic metadata 502 may allow data augmentation process 10 to determine various characteristics of the feature-based voice data and perform 402 one or more gain-based augmentations on at least a portion of the feature-based voice data associated with the signal.

In some implementations, data augmentation process 10 may determine 408 a distribution of gain levels associated with the target acoustic domain. For example and in some implementations, when performing 406 the one or more gain-based augmentations on feature-based voice data associated with a first acoustic domain for use in a target acoustic domain, the target acoustic domain may not have a consistent gain level or range of gain levels. In this example, data augmentation process 10 may determine 408 a distribution of gain levels associated with the target acoustic domain. For example, data augmentation process 10 may process training data (e.g., time domain data and/or feature-based voice data) from the target acoustic domain to determine a distribution of gain levels. In some implementations, determining 408 the distribution of gain levels from training data associated with the target acoustic domain may include determining how the gain of the training data varies over time for particular frequencies or frequency bands. In this manner, data augmentation process 10 may determine 408 a distribution of gain levels to apply when performing gain-based augmentations on the feature-based voice data associated with the first acoustic domain.

In some implementations, performing 402 the one or more gain-based augmentations to the at least a portion of the feature-based voice data may include performing 410 the one or more gain-based augmentations to the at least a portion of the feature-based voice data based upon, at least in part, the distribution of gain levels associated with the target acoustic domain. As discussed above, with a distribution of gain levels associated with the target acoustic domain, data augmentation process 10 may perform 410 one or more gain-based augmentations on at least a portion of the feature-based voice data to include a similar distribution of gain levels as the target acoustic domain.

Returning to the examples of FIGS. 5-6 and in some implementations, suppose data augmentation process 10 determines 408 a distribution of gain levels (e.g., distribution of gain levels 504) associated with the target acoustic domain (e.g., the acoustic domain associated with a speaker's head turning while speaking within a laboratory). In this example, data augmentation process 10 may perform 410 one or more gain-based augmentations on the feature-based voice data (e.g., feature-based voice data 500) associated with the first acoustic domain (e.g., the acoustic domain associated with a speaker speaking directly into a microphone within a laboratory) to include a similar or the same distribution of gain levels as in the target acoustic domain (e.g., the acoustic domain associated with a speaker's head turning while speaking within a laboratory).

As will be discussed in greater detail below, data augmentation process 10 may perform 410 gain-based augmentations on feature-based voice data 500 by amplifying and/or attenuating certain portions (e.g., particular frequencies, frequency bands, etc.) of feature-based voice data 500 based upon, at least in part, the distribution of gain levels associated with the target domain. In this manner, data augmentation process 10 may allow feature-based voice data 500 associated with one acoustic domain (e.g., the acoustic domain associated with a speaker speaking directly into a microphone within a laboratory) to be used to train speech processing systems in a target acoustic domain (e.g., the acoustic domain associated with a speaker's head turning while speaking within a laboratory), thus defining gain-augmented feature-based voice data (e.g., gain-augmented feature-based voice data 506).

While an example of performing 410 one or more gain-based augmentations on at least a portion of feature-based voice data has been described for augmenting feature-based voice data to include a similar distribution of gain levels as that of a target acoustic domain, it will be appreciated that data augmentation process 10 may perform 402 one or more gain-based augmentations on at least a portion of feature-based voice data for other purposes within the scope of the present disclosure. As discussed above, data augmentation may allow an existing set of training data to be used in other acoustic domains or to provide more diverse training data within the same acoustic domain. For example, suppose that a speech processing system is trained with training data having a particular gain level and/or limited range of gain levels. If a speech processing system is exposed to speech signals with gain levels that vary from the training data, the speech processing system may be less effective in processing the speech signal. In this manner, data augmentation process 10 may perform 402 one or more gain-based augmentations on at least a portion of the feature-based voice data to generate more diverse (e.g., with varying gain levels) training data for a speech processing system.

In some implementations, performing 402 the one or more gain-based augmentations to the at least a portion of the feature-based voice data may include amplifying 412 at least a portion of the feature-based voice data. For example and in some implementations, data augmentation process 10 may determine that at least a portion of the feature-based voice data needs to be amplified. In one example and as discussed above, data augmentation process 10 may receive 404 a selection of a target acoustic domain (e.g., an acoustic domain associated with a speaker speaking directly into a microphone within a laboratory) and may determine that one or more portions of the feature-based voice data (e.g., feature-based voice data 500) need additional gain to be used as training data in the target acoustic domain. For example and as discussed above, data augmentation process 10 may determine 408 a distribution of gain levels associated with the target domain to identify specific portions of feature-based voice data 500 to amplify. In this example, data augmentation process 10 may amplify 412 at least a portion of feature-based voice data 500 based upon, at least in part, the target acoustic domain (e.g., the acoustic domain associated with a speaker speaking directly into a microphone within a laboratory).

In another example, suppose that training data for a particular acoustic domain has a limited range of gain levels. In this example, data augmentation process 10 may identify particular portions of feature-based voice data 500 to amplify 412. For example, data augmentation process 10 may amplify 412 various portions of feature-based voice data 500 with lower gain levels than the existing training data to generate more diverse training data.

In some implementations, amplifying 412 at least a portion of the feature-based voice data may include amplifying portions of the feature-based voice data based upon, at least in part, the frequency or frequency bands of the feature-based voice data. For example, data augmentation process 10 may amplify 412 at least a portion of the feature-based voice data with a particular frequency or frequency band. In one example and as discussed above, suppose a selected target acoustic domain is determined to have a particular gain or distribution of gain levels. In this example, data augmentation process 10 may identify a particular frequency or frequency bands within feature-based voice data 500 that e.g., fall below the particular gain or distribution of gain levels. Data augmentation process 10 may amplify 412 the portion or portions of feature-based voice data 500 that correspond to the identified frequency or frequency bands. In this manner, data augmentation process 10 may perform 402 gain-based augmentations on at least a portion of the feature-based voice data based upon, at least in part, the frequency or frequency band of the at least a portion of the feature-based voice data.

In another example, suppose that training data for a particular acoustic domain has a limited range of gain levels at a particular frequency or frequency band. In this example, data augmentation process 10 may identify the portions of feature-based voice data 500 corresponding to these frequencies or frequency bands to amplify 412. For example, data augmentation process 10 may amplify 412 various portions of feature-based voice data 500 corresponding to particular frequencies or frequency bands with lower gain levels than the existing training data to generate more diverse training data.

In some implementations, performing 402 the one or more gain-based augmentations to the at least a portion of the feature-based voice data may include attenuating 414 at least a portion of the feature-based voice data. For example and in some implementations, data augmentation process 10 may determine that at least a portion of the feature-based voice data needs to be attenuated. In one example and as discussed above, data augmentation process 10 may receive 404 a selection of a target acoustic domain (e.g., acoustic domain associated with a speaker's head turning while speaking within a laboratory) and may determine that one or more portions of the feature-based voice data (e.g., feature-based voice data 500) need to be attenuated to be used as training data in the target acoustic domain. For example and as discussed above, data augmentation process 10 may determine 408 a distribution of gain levels associated with the target domain to identify specific portions of feature-based voice data 500 to attenuate 414. In this example, data augmentation process 10 may attenuate 414 at least a portion of feature-based voice data 500 based upon, at least in part, the target acoustic domain (e.g., the acoustic domain associated with a speaker's head turning while speaking within a laboratory).

In another example, suppose that training data for a particular acoustic domain has a limited range of gain levels. In this example, data augmentation process 10 may identify particular portions of feature-based voice data 500 to attenuate 414. For example, data augmentation process 10 may attenuate 414 various portions of feature-based voice data 500 with higher gain levels than the existing training data to generate more diverse training data.

In some implementations, attenuating 414 at least a portion of the feature-based voice data may include attenuating portions of the feature-based voice data based upon, at least in part, the frequency or frequency bands of the feature-based voice data. For example, data augmentation process 10 may attenuate 414 at least a portion of the feature-based voice data with a particular frequency or frequency band. In one example and as discussed above, suppose a selected target acoustic domain is determined to have a particular gain or distribution of gain levels. In this example, data augmentation process 10 may identify a particular frequency or frequency bands within feature-based voice data 500 that e.g., are above the particular gain or distribution of gain levels. Data augmentation process 10 may attenuate the portion or portions of feature-based voice data 500 that correspond to the identified frequency or frequency bands. In this manner, data augmentation process 10 may perform gain-based augmentations on at least a portion of the feature-based voice data based upon, at least in part, the frequency or frequency band of the at least a portion of the feature-based voice data.

In another example, suppose that training data for a particular acoustic domain has a limited range of gain levels at a particular frequency or frequency band. In this example, data augmentation process 10 may identify the portions of feature-based voice data 500 corresponding to these frequencies or frequency bands to attenuate 414. For example, data augmentation process 10 may attenuate 414 various portions of feature-based voice data 500 corresponding to particular frequencies or frequency bands with higher gain levels than the existing training data. In this manner, data augmentation process 10 may generate diverse training data by attenuating particular frequencies or frequency bands of feature-based voice data (e.g., gain-augmented feature-based voice data 506).

In some implementations, when performing 402 the one or more gain-based augmentations to the at least a portion of the feature-based voice data to generate more diverse training data, data augmentation process 10 may apply a random gain factor to each portion (e.g., each Mel Filter Bank or other feature domain portion). In some implementations, the random gain factor may be predefined and/or determined based upon, at least in part, a target signal-to-noise ratio (SNR) for feature-based voice data. For example, data augmentation process 10 may amplify 412 and/or attenuate 414 various portions of feature-based voice data 500 with randomly determined and/or predefined gain factors. In some implementations, data augmentation process 10 may determine the range of gain factors to be applied based upon, at least in part, a target SNR of a target acoustic domain.

Rate-Based Augmentations of Feature-Based Voice Data

Figure 7:
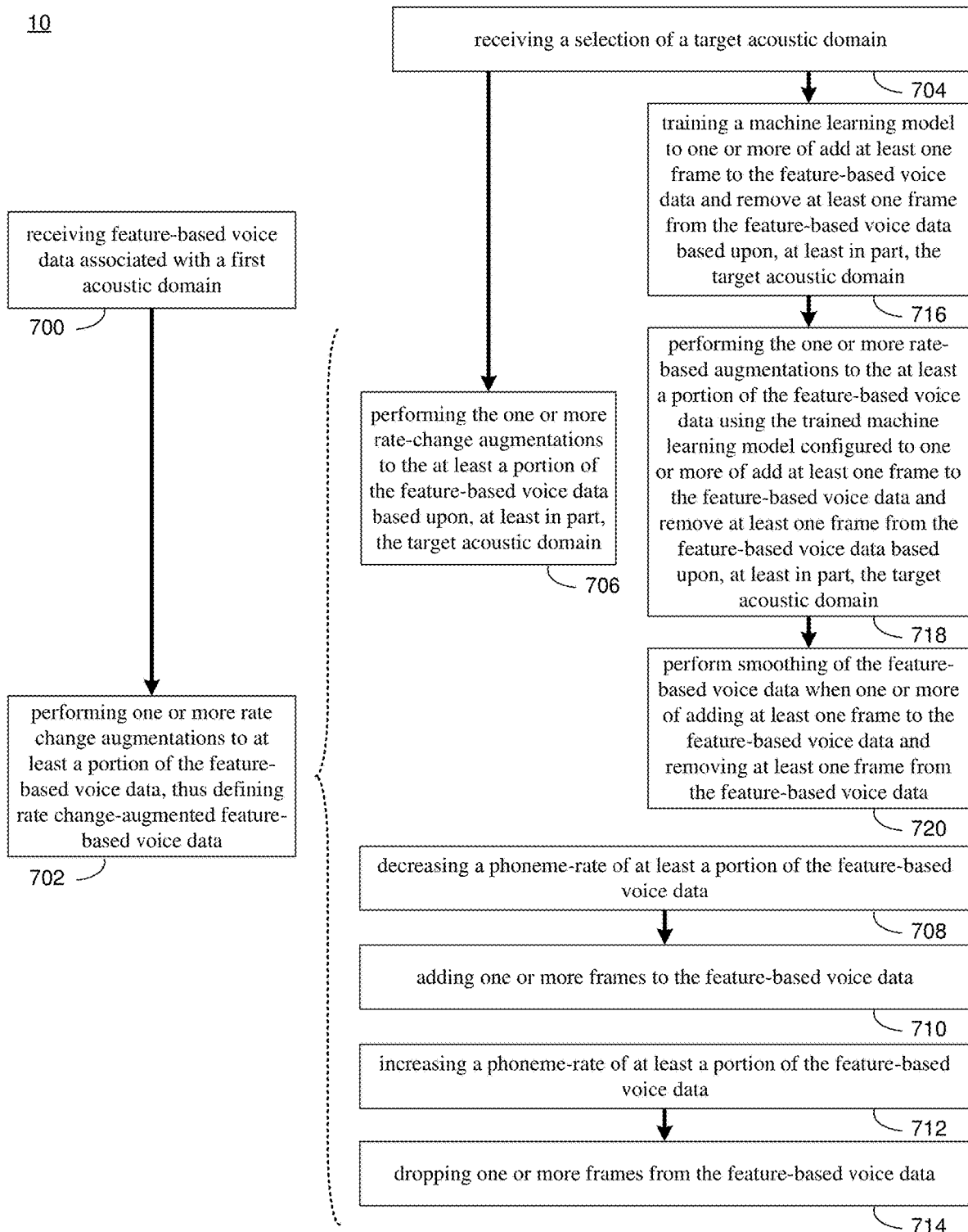
FIG. 7 is a flow chart of one implementation of the data augmentation process of FIG. 1.

Referring also to FIG. 7 and in some implementations, data augmentation process 10 may receive 700 feature-based voice data associated with a first acoustic domain. One or more rate-based augmentations may be performed 702 on at least a portion of the feature-based voice data, thus defining rate-based augmented feature-based voice data. As will be discussed in greater detail below, a rate-based augmentation may generally include any change to a speaking rate within the feature-based voice data. As is known in the art, a speech rate may generally include the rate at which a person speaks as recorded within a signal.

In some implementations, data augmentation process 10 may receive 700 feature-based voice data associated with a first acoustic domain. As discussed above and in some implementations, feature-based voice data may be generated by converting a signal or at least a portion of a signal to the feature domain. Referring again to the example of FIG. 3 and in some implementations, data augmentation process 10 may receive 200 an audio signal (e.g., audio signal 300) and convert 204 the audio signal from the time domain to the feature domain to generate feature-based voice data (e.g., feature-based voice data 332) associated with the audio signal (e.g., audio signal 300). While an example has been provided of converting a signal from the time domain to the feature domain, it will be appreciated that a signal may be converted to the feature domain from any domain, within the scope of the present disclosure.

Figure 8:
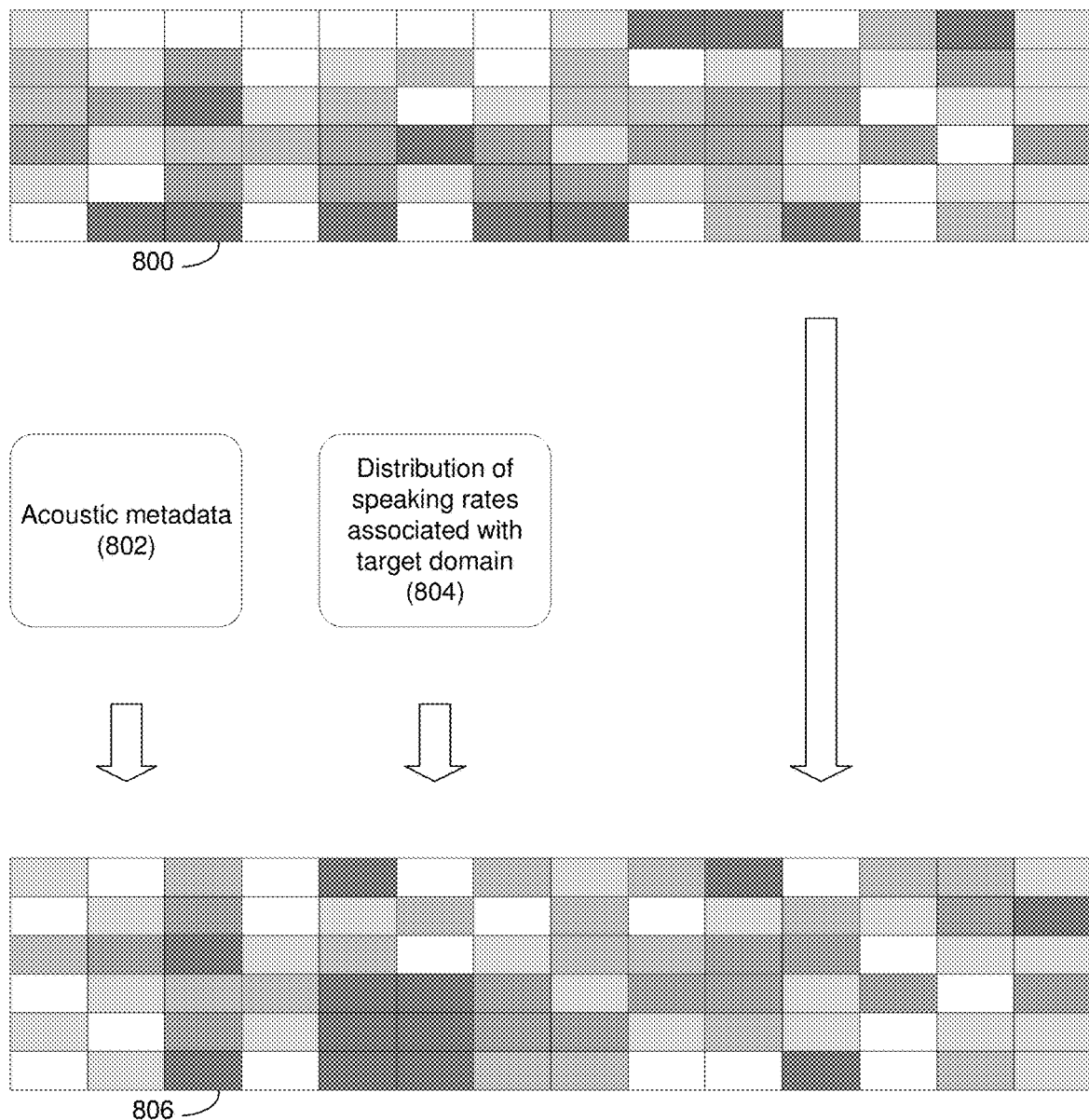
FIG. 8 is a diagrammatic view of one or more rate-based augmentations performed on feature-based voice data according to one implementation of the data augmentation process of FIG. 1.

In some implementations, data augmentation process 10 may perform 702 one or more rate-based augmentations on at least a portion of the feature-based voice data, thus defining rate-based augmented feature-based voice data. Referring also to the example of FIG. 8 and in some implementations, data augmentation process 10 may receive 700 feature-based voice data (e.g., feature-based voice data 800) associated with a first acoustic domain. In the example of FIG. 8, feature-based voice data 800 may include a plurality of feature coefficients (e.g., Mel Filter Bank coefficients, Mel-frequency cepstral coefficients, etc.) represented as a spectrogram of a signal as a function of frequency (on the vertical axis) and time (on the horizontal axis) where the shade of each quadrant represents the amplitude of each feature coefficient. While one example of feature-based voice data has been described, it will be appreciated that the feature-based voice data may be represented in various ways within the scope of the present disclosure.

In this example, data augmentation process 10 may perform 702 one or more rate-based augmentations on at least a portion of the feature-based voice data associated with the first acoustic domain. As will be discussed in greater detail below, it may be desirable to augment at least a portion of feature-based voice data associated with a particular acoustic domain for various reasons. For example and in some implementations, data augmentation process 10 may perform 702 one or more rate-based augmentations on at least a portion of the feature-based voice data to utilize the feature-based voice data for training a speech processing system in a target acoustic domain. In this example, data augmentation process 10 may train a speech processing system with feature-based voice data from a different acoustic domain which may allow for speech processing systems to be effectively utilized in various acoustic domains using an augmented set of training feature-based voice data.

In another example, data augmentation process 10 may perform 702 one or more rate-based augmentations on at least a portion of the feature-based voice data to generate additional training data for speech processing systems with varying speaking rates. In this manner, data augmentation process 10 may train speech processing systems to be more robust against variations in speaking rates by augmenting a set of training feature-based voice data with various speaking rates. While two examples have been provided for utilizing rate-based augmented feature-based voice data, it will be appreciated that data augmentation process 10 may perform rate-based augmentations on feature-based voice data for various other purposes within the scope of the present disclosure. For example and in some implementations, rate-based augmentations may be used to adapt a speech processing system with new adaptation data (e.g., rate-based augmentations).

As discussed above, after a signal is converted to the feature domain, it may be impossible to determine certain acoustic properties of the signal without converting the signal back to the time domain. In some implementations, when receiving 700 the feature-based voice data, data augmentation process 10 may also receive information associated with the feature-based voice data. In some implementations, the information associated with the feature-based voice data may include information about the feature-based voice data generally. For example, the information may identify the feature-based voice data as being recorded in a general acoustic domain (e.g., feature-based voice data converted from signals with typical conversation-based speaking rates). In some implementations, the information associated with the feature-based voice data may or may not be specific to the feature-based voice data. For example, the information may provide general characteristics associated with the feature-based voice data.

In some implementations, processing 204 the feature-based voice data associated with the signal based upon, at least in part, the acoustic metadata may include performing 212 one or more rate-based augmentations on at least a portion of the feature-based voice data associated with the signal based upon, at least in part, the acoustic metadata. As discussed above, data augmentation process 10 may extract 200 acoustic metadata (e.g., acoustic metadata 802) from the signal before the signal is converted 202 to the feature domain. As discussed above, the extracted acoustic metadata may include global acoustic metadata associated with a signal generally and/or acoustic metadata associated with, or specific to, particular portions of the signal. In this manner, the extracted acoustic metadata may provide more specific information about the acoustic domain of the feature-based voice data than available from other more generalized information about the feature-based voice data. As will be discussed in greater detail below and in some implementations, the acoustic metadata (e.g., acoustic metadata 802) associated with a signal may allow data augmentation process 10 to determine various characteristics of the feature-based voice data and perform 212 one or more rate-based augmentations on at least a portion of the feature-based voice data associated with the signal based upon, at least in part, the acoustic domain of the feature-based voice data.

In some implementations, data augmentation process 10 may receive 704 a selection of a target acoustic domain. As discussed above, a target acoustic domain may generally include a target set of factors and characteristics that define the quality of a signal. In some implementations, data augmentation process 10 may receive 704 a selection of a target acoustic domain by providing particular speaking rate characteristics associated with the target acoustic domain. In some implementations and as discussed above, data augmentation process 10 may utilize a graphical user interface for receiving 704 a selection of a target acoustic domain from a library of predefined acoustic domains. In one example, data augmentations process 10 may receive selections (e.g., via a graphical user interface) of various characteristics of the acoustic domain (e.g., a selection of the reverberation, signal-to-noise ratio (SNR), a type of microphone array, a particular noise track, etc.) to define a target acoustic domain. As will be discussed in greater detail below and in some implementations, data augmentation process 10 may receive a range or distribution of characteristics for the target acoustic domain.

In one example, suppose a speech processing system is trained for processing speech in a particular acoustic domain (e.g., a speaker speaking into a microphone dictation system configured to recognize and transcribe speech). In this example, because the speaker is speaking directly into a microphone to dictate speech, the speaker's speaking rate and annunciation may be very clear and the feature-based voice data may have a particular speaking rate or limited range of speaking rates.

However, other acoustic domains may receive and process speech with different speaking rates or changes in speaking rates. For example, suppose a microphone is deployed in a medical environment and is configured to record and process conversations between a medical professional and a patient. In this example, the speaking rate of a medical professional may be distinct from that of a speaker using a dictation system and the speaking rate of the medical professional and the patient may be distinct. Data augmentation process 10 may receive 704 a selection of the acoustic domain associated with a medical professional's office including a microphone array configured to process conversations between medical professionals and patients. While an example of a particular target acoustic domain has been provided, it will be appreciated that various target acoustic domains may be selected within the scope of the present disclosure.

In some implementations, performing 702 the one or more rate-based augmentations to the at least a portion of the feature-based voice data may include performing 706 the one or more rate-based augmentations to the at least a portion of the feature-based voice data based upon, at least in part, the target acoustic domain. Returning to the above example, suppose data augmentation process 10 receives 704 a selection of the acoustic domain associated with a medical professional's office including a microphone array configured to process conversations between medical professionals and patients. In this example, data augmentation process 10 may perform 706 one or more rate-based augmentations on at least a portion of the feature-based voice data of the first acoustic domain (e.g., the acoustic domain associated with a speaker speaking into a microphone dictation system configured to recognize and transcribe speech).

In some implementations, data augmentation process 10 may perform 706 one or more rate-based augmentations on at least a portion of feature-based voice data 800 to account for the variations in speaking rates. Accordingly, data augmentation process 10 may perform 706 rate-based augmentations to map feature-based voice data 800 from the first acoustic domain (e.g., the acoustic domain associated with a speaker speaking into a microphone dictation system) to a target acoustic domain (e.g., the acoustic domain associated with a medical professional's office including a microphone array configured to process conversations between medical professionals and patients). In this manner, a speech processing system may be trained using feature-based voice data from one acoustic domain for processing speech in another acoustic domain.

In some implementations, data augmentation process 10 may determine a distribution of speaking rates and changes in speaking rates associated with the target acoustic domain. For example and in some implementations, when performing 706 the one or more rate-based augmentations on feature-based voice data associated with a first acoustic domain for use in a target acoustic domain, the target acoustic domain may not have a consistent speaking rate or known range of speaking rates. In this example, data augmentation process 10 may determine a distribution of speaking rates associated with the target acoustic domain. For example, data augmentation process 10 may process training data (e.g., time domain data and/or feature-based voice data) from the target acoustic domain to determine a distribution of speaking rates. In some implementations, determining the distribution of speaking rates from training data associated with the target acoustic domain may include determining how the rate of speaking within the training data varies over time. In this manner, data augmentation process 10 may determine a distribution of speaking rates to apply when performing rate-based augmentations on the feature-based voice data associated with the first acoustic domain.

In some implementations, performing 702 the one or more rate-based augmentations to the at least a portion of the feature-based voice data may include performing the one or more rate-based augmentations to the at least a portion of the feature-based voice data based upon, at least in part, the distribution of speaking rates associated with the target acoustic domain. As discussed above, with a distribution of speaking rates associated with the target domain, data augmentation process 10 may perform 702 one or more rate-based augmentations on at least a portion of the feature-based voice data to include a similar distribution of speaking rates as the target acoustic domain.

In some implementations, suppose data augmentation process 10 determines a distribution of speaking rates (e.g., distribution of speaking rates 804) associated with the target acoustic domain (e.g., the acoustic domain associated with a medical professional's office including a microphone array configured to process conversations between medical professionals and patients). In this example, data augmentation process 10 may perform one or more rate-based augmentations on the feature-based voice data (e.g., feature-based voice data 800) associated with the first acoustic domain (e.g., the acoustic domain associated with a speaker speaking into a microphone dictation system configured to recognize and transcribe speech) to include a similar or the same distribution of speaking rates as in the target acoustic domain.

As will be discussed in greater detail below, data augmentation process 10 may perform rate-based augmentations on feature-based voice data 800 by adding and/or dropping certain portions (e.g., frames within the feature domain and/or frequency domain) of feature-based voice data 800 based upon, at least in part, the distribution of speaking rates associated with the target domain. In this manner, data augmentation process 10 may allow feature-based voice data 800 associated with one acoustic domain (e.g., the acoustic domain associated with a speaker speaking into a microphone dictation system) to be used to train speech processing systems in a target acoustic domain (e.g., the acoustic domain associated with a medical professional's office including a microphone array configured to process conversations between medical professionals and patients), thus defining rate-based augmented feature-based voice data (e.g., rate-based augmented feature-based voice data 806).

While an example of performing 706 one or more rate-based augmentations on at least a portion of feature-based voice data has been described for augmenting feature-based voice data to include a similar distribution of speaking rates as that of a target acoustic domain, it will be appreciated that data augmentation process 10 may perform 702 one or more rate-based augmentations on at least a portion of feature-based voice data for other purposes within the scope of the present disclosure. As discussed above, data augmentation may allow an existing set of training data to be used in other acoustic domains or to provide more diverse training data within the same acoustic domain. For example, suppose that a speech processing system is trained with training data having a particular speaking rate and/or limited range of speaking rates. If a speech processing system is exposed to speech signals with speaking rates that vary from the training data, the speech processing system may be less effective in processing the speech signals. In this manner, data augmentation process 10 may perform 702 one or more rate-based augmentations on at least a portion of the feature-based voice data to generate more diverse (e.g., with varying speaking rates) training data for a speech processing system.

In some implementations, performing 702 the one or more rate-based augmentations to the at least a portion of the feature-based voice data may include decreasing 708 a phoneme-rate of at least a portion of the feature-based voice data. As is known in the art, a phoneme may generally include small and perceptually distinct units of sound in a language used to distinguish one word from another word and a phoneme-rate may generally include the number of phonemes per some unit of time. For example and in some implementations, data augmentation process 10 may determine a phoneme-rate of at least a portion of the feature-based voice data (e.g., from acoustic metadata 802 and/or from general information associated with feature-based voice data 800). In some implementations, data augmentation process 10 may decrease 708 a phoneme-rate of at least a portion of the feature-based voice data to utilize the feature-based voice data for a target acoustic domain and/or to generate additional training data with varying phoneme-rates.

In some implementations, decreasing 708 a phoneme-rate of at least a portion of the feature-based voice data may include adding 710 one or more frames to the feature-based voice data. For example, suppose that feature-based voice data 800 is associated with a first acoustic domain (e.g., an acoustic domain associated with a medical professional's office including a microphone array configured to process conversations between medical professionals and patients). Suppose that data augmentation process 10 receives 704 a selection of a target acoustic domain (e.g., the acoustic domain associated with a speaker speaking into a microphone of a dictation system configured to recognize and transcribe speech). In this example, because a speaker (e.g., a patient and/or a medical professional) is speaking more quickly than when speaking into the microphone of a dictation system, the phoneme-rate may of feature-based voice data 800 may be too fast for processing by a dictation system. Accordingly, data augmentation process 10 may determine a phoneme-rate and/or a distribution of phoneme rates associated with the target acoustic domain (e.g., the acoustic domain associated with a speaker speaking into a microphone of a dictation system) and a phoneme rate and/or a distribution of phoneme rates of feature-based voice data 800 (e.g., the acoustic domain associated with a medical professional's office including a microphone array configured to process conversations between medical professionals and patients).

In this example, suppose data augmentation process 10 determines that the phoneme-rate and/or distribution of phoneme rates of feature-based voice data 800 is higher than that of target acoustic domain. Data augmentation process 10 may decrease 708 the phoneme-rate of feature-based voice data 800 by adding 710 one or more frames to feature-based voice data 800. In some implementations, the one or more frames may include frame of frequencies and/or bands of frequencies. For example, data augmentation process 10 may add 710 one or more frames or portions without a phoneme and/or with the same phoneme as a previous frame or portion of feature-based voice data 800. In this manner, data augmentation process 10 may decrease 708 the phoneme-rate of feature-based voice data based upon, at least in part, the phoneme-rate of the target acoustic domain.

While the above example of decreasing 708 a phoneme-rate of a least a portion of feature-based voice data includes decreasing 708 the phoneme-rate of the at least a portion of the feature-based voice data based upon, at least in part, the phoneme rate and/or distribution of phoneme-rates of a target acoustic domain, it will be appreciated that data augmentation process 10 may decrease 708 the phoneme-rate of the at least a portion of the feature-based voice data for other purposes (e.g., to generate more diverse training data with varying phoneme-rates, etc.).

In some implementations, performing 702 the one or more rate-based augmentations to the at least a portion of the feature-based voice data may include increasing 712 a phoneme-rate of at least a portion of the feature-based voice data. As discussed above and in some implementations, data augmentation process 10 may determine a phoneme-rate of at least a portion of the feature-based voice data (e.g., from acoustic metadata 802 and/or from general information associated with feature-based voice data 800). In some implementations, data augmentation process 10 may increase 712 a phoneme-rate of at least a portion of the feature-based voice data to utilize the feature-based voice data for a target acoustic domain and/or to generate additional training data with varying phoneme-rates.

In some implementations, increasing 712 a phoneme-rate of at least a portion of the feature-based voice data may include dropping 714 one or more frames from the feature-based voice data. For example, suppose that feature-based voice data 800 is associated with a first acoustic domain (e.g., an acoustic domain associated with a speaker speaking into a microphone of a dictation system). Suppose that data augmentation process 10 receives a selection of a target acoustic domain (e.g., an acoustic domain associated with a medical professional's office including a microphone array configured to process conversations between medical professionals and patients). In this example, because a speaker speaking into the microphone of a dictation system speaks more slowly than the speakers (e.g., patients and/or medical professionals) do in a conversation, the phoneme-rate may of feature-based voice data 800 may be too slow for processing by speech processing system trained with conversational data. Accordingly, data augmentation process 10 may determine a phoneme-rate and/or a distribution of phoneme rates associated with the target acoustic domain (e.g., the acoustic domain associated with a medical professional's office including a microphone array configured to process conversations between medical professionals and patients) and a phoneme rate and/or a distribution of phoneme rates of feature-based voice data 800 (e.g., the acoustic domain associated with a speaker speaking into a microphone of a dictation system).

In this example, suppose that data augmentation process 10 determines that the phoneme-rate and/or distribution of phoneme rates of feature-based voice data 800 is lower than that of the target acoustic domain. Data augmentation process 10 may increase 712 the phoneme-rate of feature-based voice data 800 by dropping 714 one or more frames from feature-based voice data 800. In some implementations, the one or more frames may include a frequency and/or bands of frequencies. For example, data augmentation process 10 may drop 714 one or more frames or portions without a phoneme and/or with the same phoneme as a previous frame or portion of feature-based voice data 800. In this manner, data augmentation process 10 may increase 712 the phoneme-rate of feature-based voice data based upon, at least in part, the phoneme-rate of the target acoustic domain.

While the above example of increasing 712 a phoneme-rate of a least a portion of feature-based voice data includes increasing 712 the phoneme-rate of the at least a portion of the feature-based voice data based upon, at least in part, the phoneme rate and/or distribution of phoneme-rates of a target acoustic domain, it will be appreciated that data augmentation process 10 may increase 712 the phoneme-rate of the at least a portion of the feature-based voice data for other purposes (e.g., generate more diverse training data with varying phoneme-rates).

In some implementations, performing 702 the one or more rate-based augmentations to the at least a portion of the feature-based voice data may include training a machine learning system or model (e.g., machine learning model 72) to perform the one or more rate-based augmentations. As is known in the art, a machine learning model may generally include an algorithm or combination of algorithms that has been trained to recognize certain types of patterns. For example, machine learning approaches may be generally divided into three categories, depending on the nature of the signal available: supervised learning, unsupervised learning, and reinforcement learning. As is known in the art, supervised learning may include presenting a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). As is known in the art, reinforcement learning may generally include a computing device interacting in a dynamic environment in which it must perform a certain goal (such as driving a vehicle or playing a game against an opponent). As it navigates its problem space, the program is provided feedback that's analogous to rewards, which it tries to maximize. While three examples of machine learning approaches have been provided, it will be appreciated that other machine learning approaches are possible within the scope of the present disclosure.

In some implementations, data augmentation process 10 may train 716 a machine learning model to one or more of add at least one frame to the feature-based voice data and drop at least one frame from the feature-based voice data based upon, at least in part, the target acoustic domain. For example and as discussed above, data augmentation process 10 may train a neural network (e.g., machine learning model 72) to decrease 708 and/or increase 712 the phoneme-rate of feature-based voice data 800 by providing training data with various phoneme-rates associated with various feature-based voice data. As discussed above and in some implementations, data augmentation process 10 may provide training data associated with a target acoustic domain to machine learning model 72 and machine learning model 72 may determine a speaking rate associated with the target acoustic domain and/or a distribution of speaking rates for the target acoustic domain.

In some implementations, performing 702 the one or more rate-based augmentations to the at least a portion of the feature-based voice data based upon, at least in part, the target acoustic domain may include performing 718 the one or more rate-based augmentations to the at least a portion of the feature-based voice data using the trained machine learning model configured to one or more of add at least one frame to the feature-based voice data and drop at least one frame from the feature-based voice data based upon, at least in part, the target acoustic domain. In this manner, the neural network may be trained to add one or more frames to and/or drop one or more frames from the feature-based voice data with the input of a target acoustic domain and/or a selection to generate more diverse training data. While an example of a neural network has been described, it will be appreciated that any artificial intelligence or machine learning system may be trained to perform the one or more rate-based augmentations within the scope of the present disclosure. Accordingly, data augmentation process 10 may train a neural network (e.g., machine learning model 72) to achieve particular rate changes directly in the feature domain.

In some implementations, data augmentation process 10 may perform smoothing 720 and/or interpolation when adding frames to and/or dropping frames from feature-based voice data 800 using machine learning model 72. For example, data augmentation process 10 may smoothen the frame transitions (e.g., in the frequency domain) when adding frames and/or dropping frames. In some implementations, data augmentation process 10 may determine, in response to adding and/or dropping frames from feature-based voice data 800, whether rate-based augmented feature-based voice data 806 is sufficiently smooth (e.g., based upon, a threshold smoothness, a threshold rate-change gradient, etc.). Accordingly, trained machine learning model 72 may be configured to ensure that frames are "intelligently" added to and/or dropped from rate-based augmented feature-based voice data 806. For example, data augmentation process 10 may, via machine learning model 72, may apply an interpolation of feature-based coefficients of rate-based augment feature-based voice data 806 to smooth 720 transitions.

Audio Feature-Based Augmentations of Feature-Based Voice Data

Figure 9:
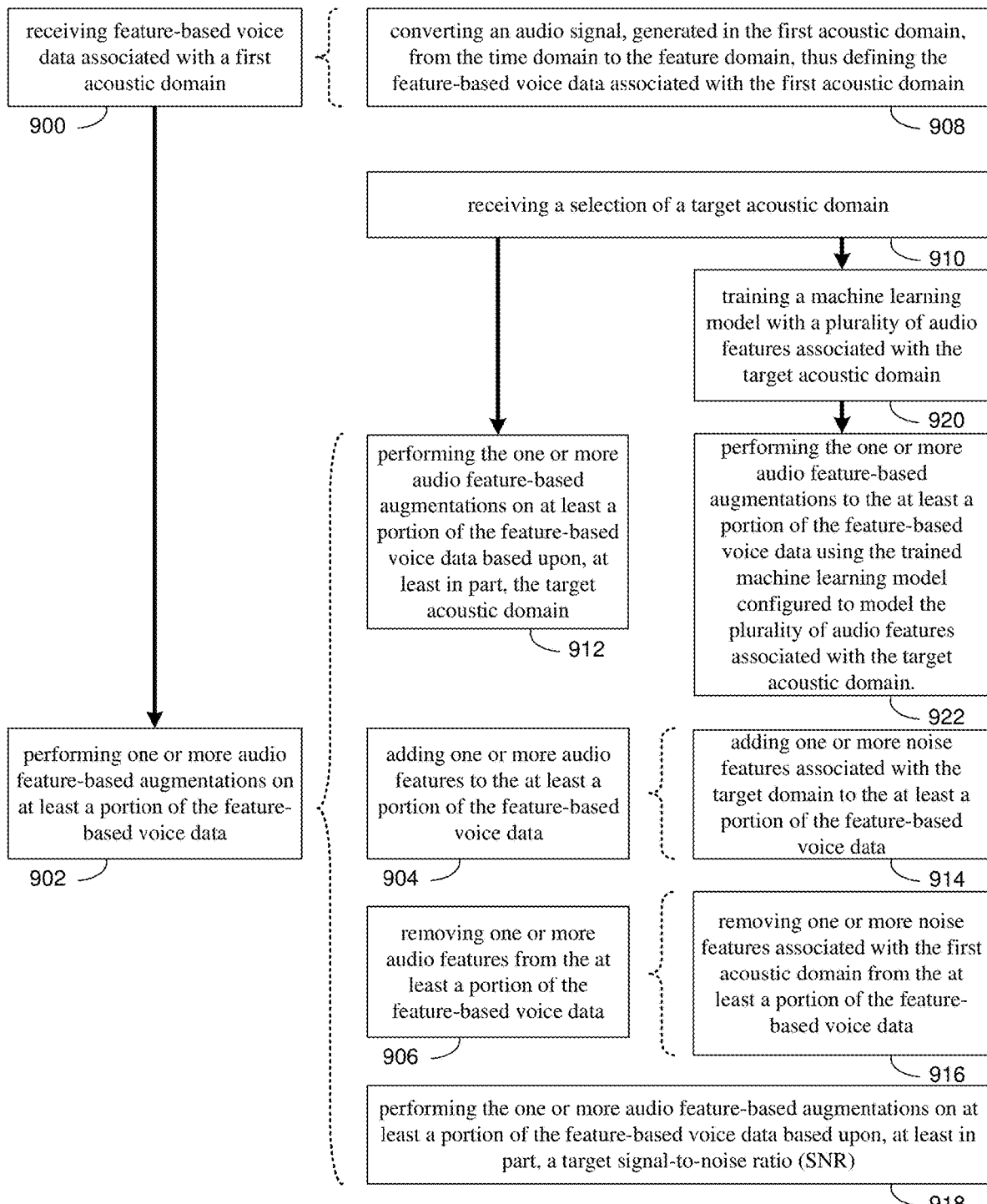
FIG. 9 is a flow chart of one implementation of the data augmentation process of FIG. 1.

Referring also to FIG. 9 and in some implementations, data augmentation process 10 may receive 900 feature-based voice data associated with a first acoustic domain. One or more audio feature-based augmentations may be performed 902 on at least a portion of the feature-based voice data. Performing the one or more audio feature-based augmentations may include adding 904 one or more audio features to the at least a portion of the feature-based voice data and/or removing 906 one or more audio features from the at least a portion of the feature-based voice data. As will be discussed in greater detail below, an audio feature-based augmentation may generally include the supplementation of any audio feature or component to feature-based voice data. For example, data augmentation process 10 may add one or more audio features to feature-based voice data and/or may remove one or more audio features to the feature-based voice data.

As will be discussed in greater detail below, audio features may generally include noise components, speech components, or other components that may be recorded or captured in feature-based voice data. Referring again to the example of FIG. 3 and in some implementations, an audio signal (e.g., audio signal 300) may include various components (e.g., noise components, speech components, etc.). As discussed above, when converting to the feature domain, these components may be represented in the feature-based voice data. However, conventional techniques for data augmentation require the audio signal to be augmented while in the time domain. In some implementations and as will be discussed in greater detail below, data augmentation process 10 may perform one or more audio feature-based augmentations on at least a portion of feature-based voice data by adding and/or removing one or more audio features in the feature domain to or from the feature-based voice data.

In some implementations, data augmentation process 10 may receive 900 feature-based voice data associated with a first acoustic domain. As discussed above and in some implementations, feature-based voice data may be generated by converting 904 a signal or at least a portion of a signal to the feature domain. Referring again to the example of FIG. 3 and in some implementations, data augmentation process 10 may receive 900 an audio signal (e.g., audio signal 300) and convert 904 the audio signal from the time domain to the feature domain to generate feature-based voice data (e.g., feature-based voice data 332) associated with the audio signal (e.g., audio signal 300). While an example has been provided of converting a signal from the time domain to the feature domain, it will be appreciated that a signal may be converted to the feature domain from any domain, within the scope of the present disclosure.

Figure 10:
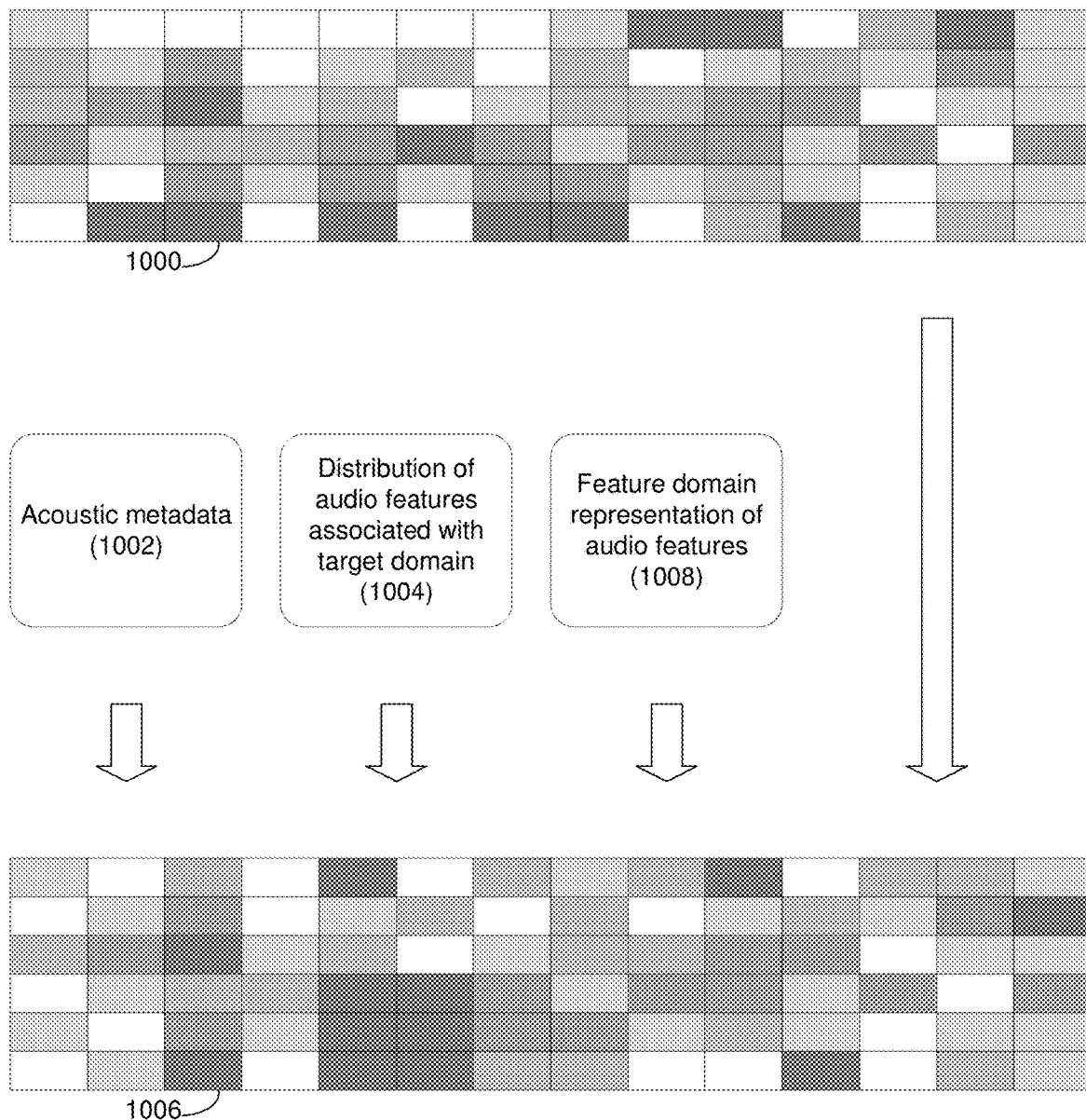
FIG. 10 is a diagrammatic view of one or more audio feature-based augmentations performed on feature-based voice data according to one implementation of the data augmentation process of FIG. 1.

In some implementations, data augmentation process 10 may perform 902 one or more audio feature-based augmentations on at least a portion of the feature-based voice data. Referring also to the example of FIG. 10 and in some implementations, data augmentation process 10 may receive 900 feature-based voice data (e.g., feature-based voice data 1000) associated with a first acoustic domain. In the example of FIG. 10, feature-based voice data 1000 may include a plurality of feature coefficients (e.g., Mel Filter Bank coefficients, Mel-frequency cepstral coefficients, etc.) represented as a spectrogram of a signal as a function of frequency (on the vertical axis) and time (on the horizontal axis) where the shade of each quadrant represents the amplitude of each feature coefficient. While one example of feature-based voice data has been described, it will be appreciated that the feature-based voice data may be represented in various ways within the scope of the present disclosure.

In some implementations, data augmentation process 10 may perform 902 one or more audio feature-based augmentations on at least a portion of the feature-based voice data associated with the first acoustic domain. As will be discussed in greater detail below, it may be desirable to augment at least a portion of feature-based voice data associated with a particular acoustic domain for various reasons. For example and in some implementations, data augmentation process 10 may perform 902 one or more audio feature-based augmentations on at least a portion of the feature-based voice data to utilize the feature-based voice data for training a speech processing system in a target acoustic domain. In this example, data augmentation process 10 may train a speech processing system with feature-based voice data from a different acoustic domain which may allow for speech processing systems to be effectively utilized in various acoustic domains using a limited set of training feature-based voice data.

In another example, data augmentation process 10 may perform 902 one or more audio feature-based augmentations on at least a portion of the feature-based voice data to generate additional training data for speech processing systems with various audio features. In this manner, data augmentation process 10 may train speech processing systems to be more robust against variations in audio features (e.g., noise components, speech components, etc.) by augmenting a set of training feature-based voice data with various audio features (e.g., noise components, speech components, etc.). While two examples have been provided for utilizing audio feature-based augmented feature-based voice data, it will be appreciated that data augmentation process 10 may perform 902 audio feature-based augmentations on feature-based voice data for various other purposes within the scope of the present disclosure. For example and in some implementations, audio feature-based augmentations may be used to adapt a speech processing system with new adaptation data (e.g., audio feature-based augmentations).

As discussed above, after a signal is converted to the feature domain, it may be impossible to determine certain acoustic properties of the signal without converting the signal back to the time domain. In some implementations, when receiving 900 the feature-based voice data, data augmentation process 10 may also receive information associated with the feature-based voice data. In some implementations, the information associated with the feature-based voice data may include information about the feature-based voice data generally. For example, the information may identify the feature-based voice data as being recorded in a general acoustic domain (e.g., vehicle noises). In some implementations, the information associated with the feature-based voice data may or may not be specific to the feature-based voice data. For example, the information may provide general characteristics associated with the feature-based voice data.

In some implementations, processing 204 the feature-based voice data associated with the signal based upon, at least in part, the acoustic metadata may include performing 214 one or more audio feature-based augmentations on at least a portion of the feature-based voice data associated with the signal based upon, at least in part, the acoustic metadata. As discussed above, data augmentation process 10 may extract 200 acoustic metadata from the signal before the signal is converted 202 to the feature domain. As discussed above, the extracted acoustic metadata may include global acoustic metadata associated with a signal generally and/or acoustic metadata associated with, or specific to, particular portions of the signal. In this manner, the extracted acoustic metadata may provide more specific information about the acoustic domain of the feature-based voice data than available from other more generalized information about the feature-based voice data. As will be discussed in greater detail below and in some implementations, the acoustic metadata (e.g. acoustic metadata 1002) associated with a signal may allow data augmentation process 10 to determine various characteristics of the feature-based voice data and perform 214 one or more audio feature-based augmentations on at least a portion of the feature-based voice data associated with the signal based upon, at least in part, the acoustic domain of the feature-based voice data.

In some implementations, data augmentation process 10 may receive 910 a selection of a target acoustic domain. As discussed above, a target acoustic domain may generally include a target set of factors and characteristics that define the quality of a signal. In some implementations, data augmentation process 10 may receive 910 a selection of a target acoustic domain by providing particular audio feature-based characteristics associated with the target acoustic domain (e.g., presence or absence of particular noise components and/or speech components). In some implementations, data augmentation process 10 may utilize a graphical user interface for receiving 910 a selection of a target acoustic domain from a library of predefined acoustic domains. In one example, data augmentation process 10 may receive selections (e.g., via a graphical user interface) of various characteristics of the acoustic domain (e.g., a selection of the reverberation, signal-to-noise ratio (SNR), a type of microphone array, a particular noise track, etc.) to define a target acoustic domain. As will be discussed in greater detail below and in some implementations, data augmentation process 10 may receive a range or distribution of characteristics for the target acoustic domain.

In one example, suppose a speech processing system is trained for processing speech in a particular acoustic domain (e.g., a speaker speaking into a microphone of a vehicle's entertainment system). In this example, because the speaker is speaking into a microphone of a vehicle, there are various noise components or features that are likely to be recorded while the speaker speaks (e.g., road noise, noise from an open window, noise from the air conditioning system, etc.).

However, other acoustic domains may receive and process speech with different audio features (or the lack thereof). For example, suppose a microphone is deployed in a medical environment and is configured to record and process conversations between a medical professional and a patient. In this example, the audio features of feature-based voice data of a recorded conversation between a medical professional and a patient may be distinct from that of a speaker speaking into the microphone of a vehicle's entertainment system. In this example, data augmentation process 10 may receive 910 a selection of a target acoustic domain (e.g., a target acoustic domain associated with a medical professional's office including a microphone array configured to process conversations between medical professionals and patients). While one example of a particular target acoustic domain has been discussed above, it will be appreciated that various target acoustic domains may be selected within the scope of the present disclosure.

In some implementations, performing 902 the one or more audio feature-based augmentations to the at least a portion of the feature-based voice data may include performing 912 the one or more audio feature-based augmentations to the at least a portion of the feature-based voice data based upon, at least in part, the target acoustic domain. Returning to the above example, suppose data augmentation process 10 receives 910 a selection of the acoustic domain associated with a medical professional's office including a microphone array configured to process conversations between medical professionals and patients, as the target acoustic domain. In this example, data augmentation process 10 may perform 912 one or more audio feature-based augmentations on at least a portion of the feature-based voice data of the first acoustic domain (e.g., the acoustic domain associated with a speaker speaking into a microphone of a vehicle's entertainment system).

In some implementations, data augmentation process 10 may perform 902 one or more audio feature-based augmentations on at least a portion of feature-based voice data 1000 to account for the variations in audio features (e.g., noise components or features, speech components or features, etc.). Accordingly, data augmentation process 10 may perform 912 audio feature-based augmentations to map feature-based voice data 1000 from the first acoustic domain (e.g., the acoustic domain associated with a speaker speaking into a microphone of a vehicle's entertainment system) to a target acoustic domain (e.g., the acoustic domain associated with a medical professional's office including a microphone array configured to process conversations between medical professionals and patients). In this manner, a speech processing system may be trained using feature-based voice data from one acoustic domain for processing speech in another acoustic domain.

In some implementations, data augmentation process 10 may determine a distribution of audio features associated with the target acoustic domain. For example and in some implementations, when performing 912 the one or more audio feature-based augmentations on feature-based voice data associated with a first acoustic domain for use in a target acoustic domain, the target acoustic domain may not have a constant noise feature or speech feature present in recordings captured within the target acoustic domain. In this example, data augmentation process 10 may determine a distribution of audio features (e.g., noise features, speech features, etc.) associated with the target acoustic domain. For example, data augmentation process 10 may process training data (e.g., time domain data and/or feature-based voice data) from the target acoustic domain to determine a distribution of audio features. In some implementations, determining the distribution of speaking rates from training data associated with the target acoustic domain may include determining how the audio features of the training data vary over time for particular frequencies or frequency bands (or other portions of feature-based voice data 1000). In this manner, data augmentation process 10 may determine a distribution of audio features to add or remove when performing audio feature-based augmentations on the feature-based voice data associated with the first acoustic domain.

In some implementations, performing 902 the one or more audio feature-based augmentations to the at least a portion of the feature-based voice data may include performing the one or more audio feature-based augmentations to the at least a portion of the feature-based voice data based upon, at least in part, the distribution of audio features associated with the target acoustic domain. As discussed above, with a distribution of audio features associated with the target domain, data augmentation process 10 may perform 902 one or more audio feature-based augmentations on at least a portion of the feature-based voice data to include a similar distribution of audio features as the target acoustic domain.

In one example, suppose data augmentation process 10 determines a distribution of audio features (e.g., distribution of audio features 1004) associated with the target acoustic domain (e.g., the acoustic domain associated with a medical professional's office including a microphone array configured to process conversations between medical professionals and patients). In this example, data augmentation process 10 may perform 912 one or more audio feature-based augmentations on the feature-based voice data (e.g., feature-based voice data 1000) associated with the first acoustic domain (e.g., the acoustic domain associated with a speaker speaking into a microphone of a vehicle's entertainment system) to include a similar or the same distribution of audio features (e.g., noise features, speech features, etc.) as in the target acoustic domain.

As will be discussed in greater detail below, data augmentation process 10 may perform 912 audio feature-based augmentations on feature-based voice data 1000 by adding 904 certain features (e.g., noise features, speech features, etc.) to and/or removing 906 certain features from feature-based voice data 1000 based upon, at least in part, the distribution of audio features associated with the target domain (e.g., distribution of audio features associated with the target domain 1004). In this manner, data augmentation process 10 may allow feature-based voice data 1000 associated with one acoustic domain (e.g., the acoustic domain associated with a speaker speaking into a microphone of a vehicle's entertainment system) to be used to train speech processing systems in a target acoustic domain (e.g., the acoustic domain associated with a medical professional's office including a microphone array configured to process conversations between medical professionals and patients), thus defining audio feature-augmented feature-based voice data (e.g., audio feature-augmented feature-based voice data 1006).

While an example of performing 912 one or more audio feature-based augmentations on at least a portion of feature-based voice data has been described for augmenting feature-based voice data to include a similar distribution of audio features as that of a target acoustic domain, it will be appreciated that data augmentation process 10 may perform one or more audio feature-based augmentations on at least a portion of feature-based voice data for other purposes within the scope of the present disclosure. As discussed above, data augmentation may allow an existing set of training data to be used in other acoustic domains and/or to provide more diverse training data within the same acoustic domain.

For example, suppose that a speech processing system is trained with training data having particular audio features (e.g., speech features, audio features, etc.). If a speech processing system is exposed to speech signals with audio features that vary from the training data, the speech processing system may be less effective in processing the speech signals. In this manner, data augmentation process 10 may perform 912 one or more audio feature-based augmentations on at least a portion of the feature-based voice data to generate more diverse (e.g., varying audio features) training data for a speech processing system.

In some implementations, performing 902 the one or more audio feature-based augmentations may include adding 904 one or more audio features to the at least a portion of the feature-based voice data. For example, suppose data augmentation process 10 receives 900 feature-based voice data associated with a first acoustic domain (e.g., an acoustic domain (as shown in FIG. 6) associated with a speaker speaking directly into a microphone within a laboratory) and a selection of a target acoustic domain (e.g., an acoustic domain associated with a speaker speaking into a microphone of a vehicle's entertainment system). In this example, data augmentation process 10 may perform 902 one or more audio feature-based augmentations on at least a portion of the feature-based voice data associated with the first acoustic domain (e.g., feature-based voice data 1000). For example, data augmentation process 10 may determine a distribution of audio features associated with the target acoustic domain and a distribution of audio features associated with the first acoustic domain. Data augmentation process 10 may determine that the target acoustic domain includes a distribution of audio features that are absent from the first acoustic domain (e.g., noise features associated with road noise).

In some implementations, adding 904 the one or more audio features to the at least a portion of the feature-based voice data may include adding 914 one or more noise features associated with the target domain to the at least a portion of the feature-based voice data. Continuing with the above example, suppose data augmentation process 10 determines that the target acoustic domain includes a distribution of audio features that are absent from the first acoustic domain (e.g., noise features associated with road noise). In this example, data augmentation process 10 may generate or access a feature domain representation of the one or more noise features. In some implementations, data augmentation process 10 may add 914 the one or more noise features (e.g., audio features 1008) to feature-based voice data 1000, thus generating audio feature-augmented feature-based voice data 1006. While an example of adding a noise feature has been described, it will be appreciated that other features (e.g., speech features, distortion features, etc.) may be added to feature-based voice data within the scope of the present disclosure.

In some implementations, performing the one or more audio feature-based augmentations may include removing 906 one or more audio features from the at least a portion of the feature-based voice data. Returning to the above example, suppose data augmentation process 10 receives 900 feature-based voice data 1000 associated with a first acoustic domain (e.g., an acoustic domain associated with a speaker speaking into a microphone of a vehicle's entertainment system) and receives 910 a target acoustic domain (e.g., an acoustic domain associated with a medical professional's office including a microphone array configured to process conversations between medical professionals and patients). In this example, data augmentation process 10 may perform 912 one or more audio feature-based augmentations on at least a portion of the feature-based voice data associated with the first acoustic domain (e.g., feature-based voice data 1000). For example, data augmentation process 10 may determine a distribution of audio features associated with the target acoustic domain and a distribution of audio features associated with the first acoustic domain. In this example, data augmentation process 10 may determine that the first acoustic domain includes a distribution of audio features that are absent from the target acoustic domain (e.g., noise features associated with road noise).

In some implementations, removing 906 the one or more audio features to the at least a portion of the feature-based voice data may include removing 916 one or more noise features associated with the first acoustic domain from the at least a portion of the feature-based voice data. Continuing with the above example, suppose data augmentation process 10 determines that the first acoustic domain includes a distribution of audio features that are absent from the target acoustic domain (e.g., noise features associated with road noise). In some implementations, data augmentation process 10 may remove 916 the one or more noise features (e.g., audio features 1008) from feature-based voice data 1000, thus generating audio feature augmented feature-based voice data 1006. While an example of removing a noise feature has been described, it will be appreciated that other features (e.g., speech features, distortion features, etc.) may be removed from feature-based voice data within the scope of the present disclosure.

In some implementations, performing 902 the one or more audio feature-based augmentations on at least a portion of the feature-based voice data may include performing 918 the one or more audio feature-based augmentations on at least a portion of the feature-based voice data based upon, at least in part, a target signal-to-noise ratio (SNR). For example, when performing 902 the one or more audio feature-based augmentations on the at least a portion of the feature-based voice data, data augmentation process 10 may account for gain factors required to achieve a target SNR. In some implementations, data augmentation process 10 may approximate the signal level of the feature-based voice data in the feature domain by computing the sum of the feature-based voice data signal (e.g., the Mel Filter Bank signal) across all time and frequency bins and dividing the sum by the approximate time domain signal length (e.g., which may be determined by multiplying the number of time bins in the feature-based voice data signal by the hop size (e.g., in samples) and adding the window length (e.g., in samples)). Data augmentation process 10 may determine the square root of the result, giving a linear relationship to the signal level of the time domain signal. In some implementations, data augmentation process 10 may adjust the signal level of feature-based voice data by multiplying the feature-based voice data signal by a squared factor (e.g., based upon, at least in part, comparing the current SNR to the target SNR). In some implementations, if a pre-emphasis filter is used when converting 904 to the feature domain (e.g., the STFT and Mel Filter Bank domain), data augmentation process 10 may divide the feature-based voice data (e.g., the Mel Filter Bank signal) by the feature domain representation of the impulse response of that filter before summing. In this manner, data augmentation process 10 may perform 918 one or more audio feature-based augmentations on at least a portion of the feature-based voice data with a target SNR.

While several examples have been provided for performing 902 one or more audio feature-based augmentations on at least a portion of feature-based voice data, it will be appreciated that audio feature-based augmentations may be performed for various purposes. For example and as discussed above, data augmentation process 10 may perform 902 one or more audio feature-based augmentations on at least a portion of feature-based voice data to supplement existing training data with various audio features (e.g., varying noise features, signal features, etc.). In some implementations, data augmentation process 10 may perform 918 the one or more audio feature-based augmentations on at least a portion of the feature-based voice data based upon, at least in part, a target signal-to-noise ratio (SNR) by applying a different gain factor (e.g., amplification and/or attenuation) to each portion of the feature-based voice data (e.g., each Mel channel), thus altering the spectral balance of the audio features (e.g., added noise) and adding diversity to the training data. In some implementations, the application of different gain factors for different portions of feature-based voice data may be guided by the target SNR such that the overall target SNR is achieved. For example, data augmentation process 10 may determine a range of gain factors to apply to each portion of feature-based voice data based upon, at least in part, the target SNR.

In some implementations, data augmentation process 10 may train 920 a machine learning model with a plurality of audio features associated with the target acoustic domain. For example and as discussed above, data augmentation process 10 may train a neural network (e.g., machine learning model 72) to add and/or remove audio features (e.g., speech features, noise features, etc.) to feature-based voice data 1000 by providing training data with various audio features associated with a target acoustic domain. As discussed above and in some implementations, data augmentation process 10 may provide training data associated with a target acoustic domain to machine learning model 72 and machine learning model 72 may determine audio features associated with the target acoustic domain and/or a distribution of audio features for the target acoustic domain.

In some implementations, performing 902 the one or more audio feature-based augmentations on at least a portion of the feature-based voice data may include performing 922 the one or more audio feature-based augmentations to the at least a portion of the feature-based voice data using the trained machine learning model configured to model the plurality of audio features associated with the target acoustic domain. For example, a neural network (e.g., machine learning model 72) may be trained to add one or more audio features to and/or remove one or more audio features from the feature-based voice data with the input of a target acoustic domain and/or a selection to generate more diverse training data. While an example of a neural network has been described, it will be appreciated that any artificial intelligence or machine learning system may be trained to perform the one or more audio feature-based augmentations within the scope of the present disclosure. Accordingly, data augmentation process 10 may train a neural network (e.g., machine learning model 72) to include particular audio features and/or to include a particular distribution of audio features associated with a target acoustic domain directly in the feature domain.

Reverberation-Based Augmentations of Feature-Based Voice Data

Figure 11:
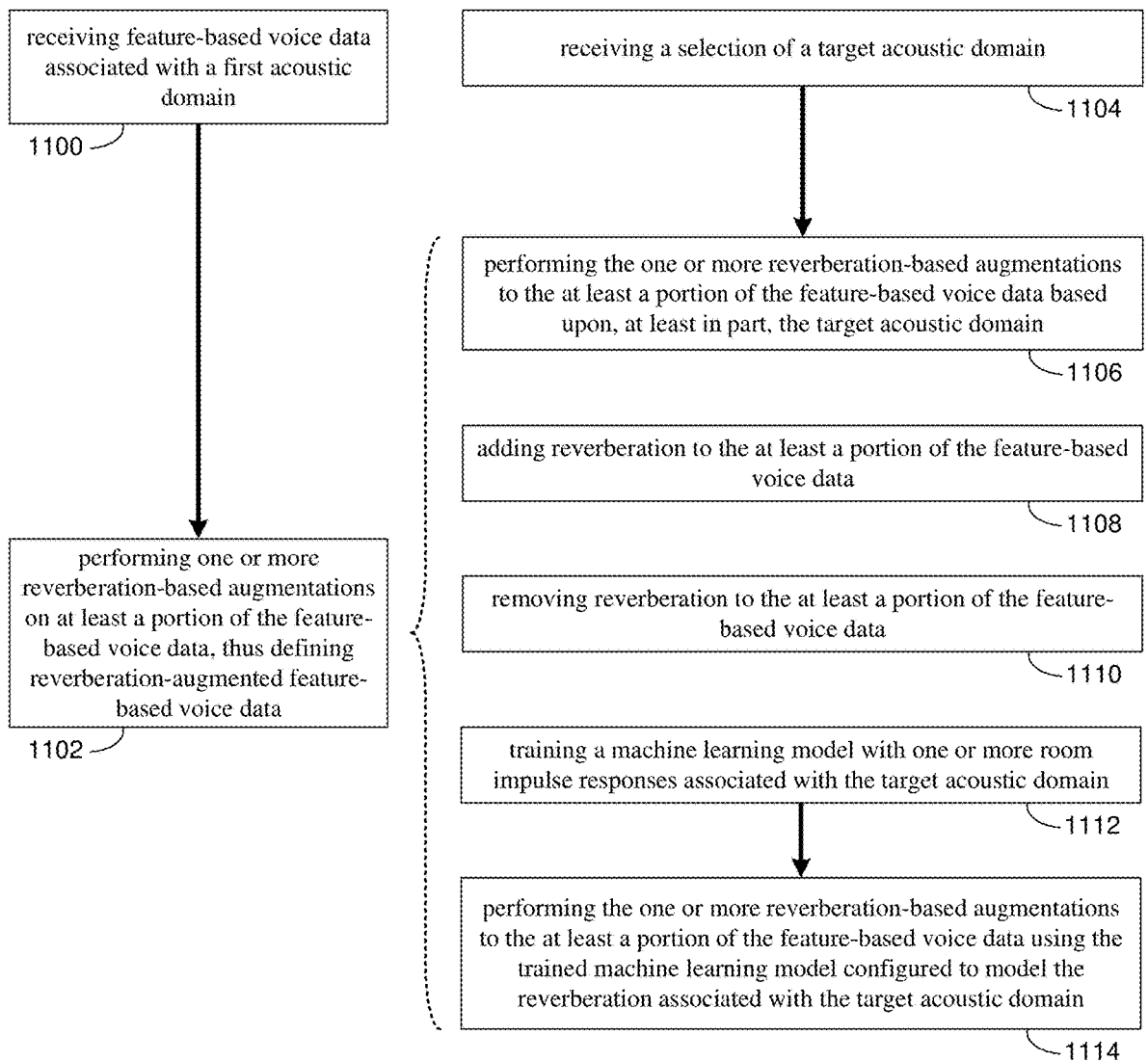
FIG. 11 is a flow chart of one implementation of the data augmentation process of FIG. 1.

Referring also to FIG. 11 and in some implementations, data augmentation process 10 may receive 1100 feature-based voice data associated with a first acoustic domain. One or more reverberation-based augmentations may be performed 1102 on at least a portion of the feature-based voice data, thus defining reverberation-augmented feature-based voice data.

As will be discussed in greater detail below, a reverberation-based augmentation may generally include any augmentation in the spectral magnitude and/or phase of the feature-based voice data representative of the effect(s) of reverberation. For example, reverberation generally describes when a sound or signal is reflected causing numerous reflections to build up and then decay as the sound is absorbed by surrounding surfaces. In some implementations, reverberation may be measured as $T_{60}$, the time it takes for the sound pressure level to reduce by 60 decibels (dB), and/or $C_{50}$, the measure of "early sound energy" (e.g., energy received between 0 milliseconds and 50 milliseconds) and "late sound energy" (e.g., energy received after 50 milliseconds). It will be appreciated that other metrics for measuring the effects of reverberation may be used within the scope of the present disclosure.

As will be discussed in greater detail below, performing one or more reverberation-based augmentations on the at least a portion of the feature-based voice data may include adding reverberation, removing reverberation (i.e., de-reverberation), adding echo, and/or removing echo (e.g., echo cancellation). Accordingly, it will be appreciated that reverberation-based augmentations may generally include any change in the spectral magnitude and/or phase of the feature-based voice data.

In some implementations, data augmentation process 10 may receive 1100 feature-based voice data associated with a first acoustic domain. As discussed above and in some implementations, feature-based voice data may be generated by converting a signal or at least a portion of a signal to the feature domain. Referring again to the example of FIG. 3 and in some implementations, data augmentation process 10 may receive 200 an audio signal (e.g., audio signal 300) and may convert 202 the audio signal from the time domain to the feature domain to generate feature-based voice data (e.g., feature-based voice data 332) associated with the audio signal (e.g., audio signal 300). While an example has been provided of converting a signal from the time domain to the feature domain, it will be appreciated that a signal may be converted to the feature domain from any domain, within the scope of the present disclosure.

Figure 12:
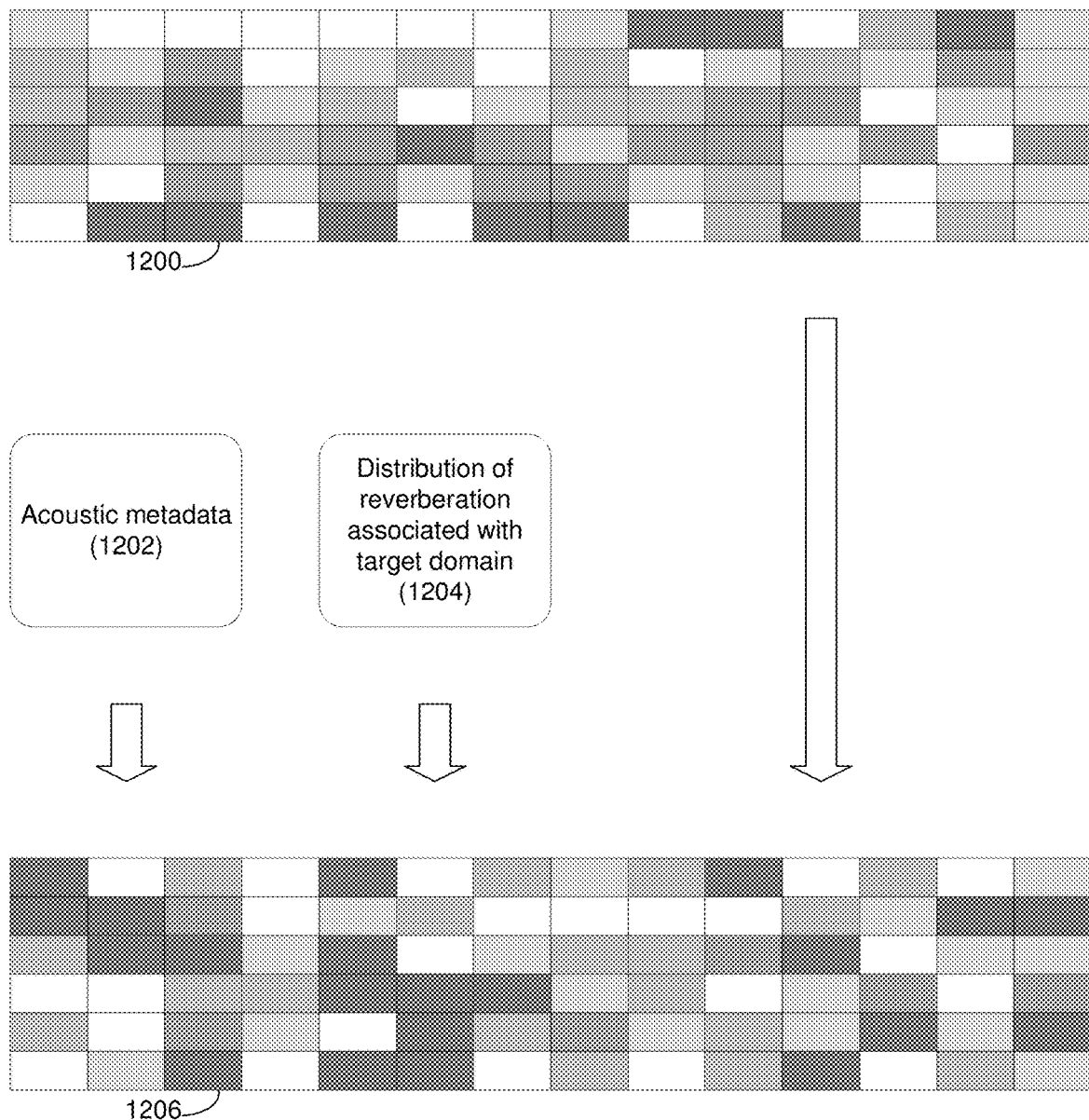
FIG. 12 is a diagrammatic view of one or more reverberation-based augmentations performed on feature-based voice data according to one implementation of the data augmentation process of FIG. 1.
Figure 13:
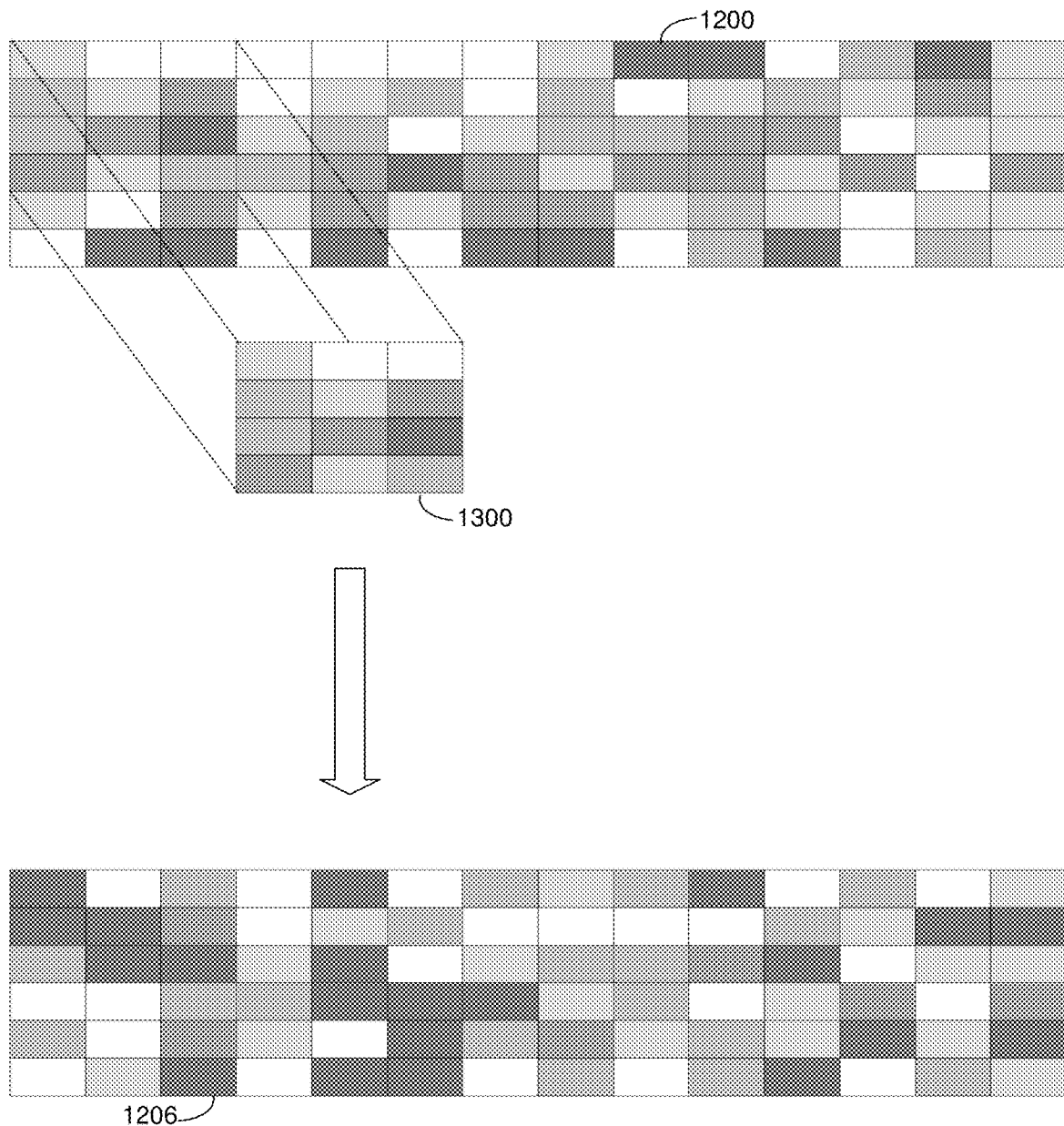
FIG. 13 is a diagrammatic view of the training of a filter for performing one or more reverberation-based augmentations performed on feature-based voice data according to one implementation of the data augmentation process of FIG. 1.
Figure 14:
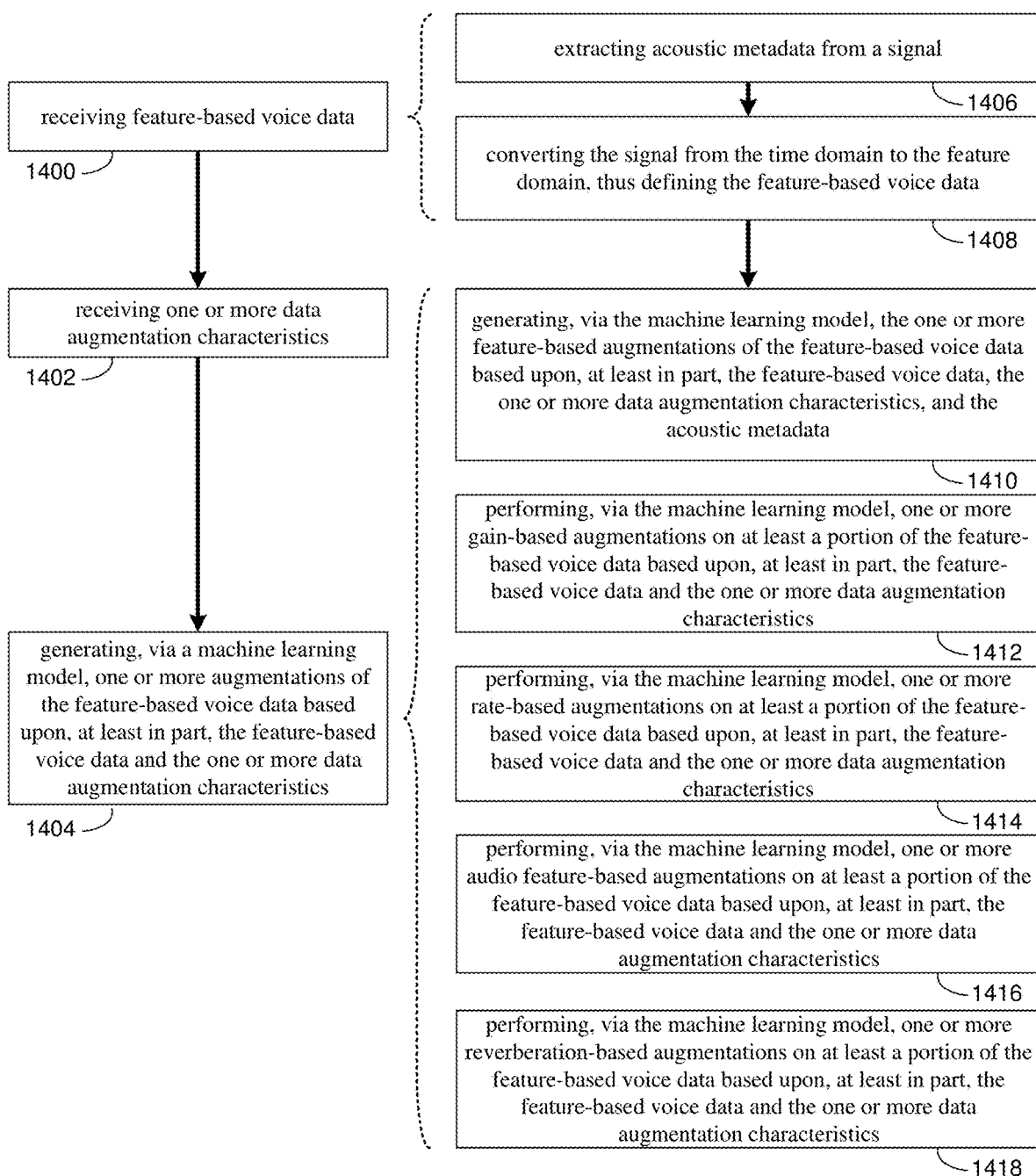
FIG. 14 is a flow chart of one implementation of the data augmentation process of FIG. 1.

In some implementations, data augmentation process 10 may perform 1102 one or more reverberation-based augmentations on at least a portion of the feature-based voice data. Referring also to the example of FIG. 12 and in some implementations, data augmentation process 10 may receive 1100 feature-based voice data (e.g., feature-based voice data 1200) associated with a first acoustic domain. In the example of FIG. 12, feature-based voice data 1200 may include a plurality of feature coefficients (e.g., Mel Filter bank coefficients, Mel-frequency cepstral coefficients, etc.) represented as a spectrogram of a signal as a function of frequency (on the vertical axis) and time (on the horizontal axis) where the shade of each quadrant represents the amplitude of each feature coefficient. While one example of feature-based voice data has been described, it will be appreciated that the feature-based voice data may be represented in various ways within the scope of the present disclosure.

In some implementation, data augmentation process 10 may perform 1102 one or more reverberation-based augmentations on at least a portion of the feature-based voice data associated with the first acoustic domain. As will be discussed in greater detail below, it may be desirable to augment at least a portion of feature-based voice data associated with a particular acoustic domain for various reasons.

For example and in some implementations, data augmentation process 10 may perform 1102 one or more reverberation-based augmentations on at least a portion of the feature-based voice data to utilize the feature-based voice data for training a speech processing system in a target acoustic domain. In this example, data augmentation process 10 may train a speech processing system with feature-based voice data from a different acoustic domain which may allow for speech processing systems to be effectively utilized in various acoustic domains using an augmented set of training feature-based voice data.

In another example, data augmentation process 10 may perform 1102 one or more reverberation-based augmentations on at least a portion of the feature-based voice data to generate additional training data for speech processing systems with various audio features. In this manner, data augmentation process 10 may train speech processing systems to be more robust against variations in reverberation by augmenting a set of training feature-based voice data with various reverberation characteristics. While two examples have been provided for utilizing reverberation-based augmented feature-based voice data, it will be appreciated that data augmentation process 10 may perform 1102 reverberation-based augmentations on feature-based voice data for other purposes within the scope of the present disclosure. For example and in some implementations, reverberation-based augmentations may be used to adapt a speech processing system with new adaptation data (e.g., reverberation-based augmentations).

As discussed above, after a signal is converted to the feature domain, it may be impossible to determine certain acoustic properties of the signal without converting the signal back to the time domain. In some implementations, when receiving 1100 the feature-based voice data, data augmentation process 10 may also receive information associated with the feature-based voice data. In some implementations, the information associated with the feature-based voice data may include only general information about the feature-based voice data. For example, the information may identify the feature-based voice data as being recorded in a general acoustic domain (e.g., a particular reverberation measurement (e.g., expressed as a $C_{50}$ value)). In some implementations, the information may or may not be specific to the feature-based voice data. For example, the information may provide general characteristics associated with the feature-based voice data.

In some implementations, processing 204 the feature-based voice data associated with the signal based upon, at least in part, the acoustic metadata may include performing 216 one or more reverberation-based augmentations on at least a portion of the feature-based voice data associated with the signal based upon, at least in part, the acoustic metadata. As discussed above, data augmentation process 10 may extract 200 acoustic metadata from the signal before the signal is converted 202 to the feature domain. As discussed above, the extracted acoustic metadata may include global acoustic metadata associated with a signal generally and/or acoustic metadata associated with or specific to particular portions of the signal. In this manner, the extracted acoustic metadata may provide more specific information about the acoustic domain of the feature-based voice data than available from other more generalized information about the feature-based voice data. As will be discussed in greater detail below and in some implementations, the acoustic metadata associated (e.g., acoustic metadata 1202) with a signal may allow data augmentation process 10 to determine various characteristics of the feature-based voice data and perform 216 one or more reverberation-based augmentations on at least a portion of the feature-based voice data associated with the signal based upon, at least in part, the acoustic domain of the feature-based voice data.

In some implementations, data augmentation process 10 may receive 1104 a selection of a target acoustic domain. As discussed above, a target acoustic domain may generally include a target set of factors and characteristics that define the quality of a signal. In some implementations, data augmentation process 10 may receive 1104 a selection of a target acoustic domain by providing particular reverberation-based characteristics associated with the target acoustic domain (e.g., reverberation measured in $T_{60}$, $C_{50}$, etc.). In some implementations, data augmentation process 10 may utilize a graphical user interface for receiving 1104 a selection of a target acoustic domain from a library of predefined acoustic domains. In one example, data augmentations process 10 may receive selections (e.g., via a graphical user interface) of various characteristics of the acoustic domain (e.g., a selection of the reverberation, signal-to-noise ratio (SNR), a type of microphone array, a particular noise track, etc.) to define a target acoustic domain. As will be discussed in greater detail below and in some implementations, data augmentation process 10 may receive a range or distribution of characteristics for the target acoustic domain.

In one example, suppose a speech processing system is trained for processing speech in a particular acoustic domain (e.g., a telephone conference where a speaker is talking very close to the microphone). In this example, because the speaker is speaking very close to the microphone, there will be minimal reverberation.

However, other acoustic domains may receive and process speech with different reverberation characteristics. For example, suppose a microphone is deployed in a conference room where the microphones are positioned on a table a few meters away from the speakers. In this example, the reverberation of the feature-based voice data may be more pronounced than the reverberation from that of a speaker speaking very close to the microphone. In this example, data augmentation process 10 may receive 1104 a selection of a target acoustic domain (e.g., a target acoustic domain associated with a conference room where the microphones are positioned on a table a few meters away from the speakers). While an example of a particular target acoustic domain has been provided, it will be appreciated that various target acoustic domains may be selected within the scope of the present disclosure.

In some implementations, performing 1102 the one or more reverberation-based augmentations to the at least a portion of the feature-based voice data may include performing 1106 the one or more reverberation-based augmentations to the at least a portion of the feature-based voice data based upon, at least in part, the target acoustic domain. Returning to the above example, suppose data augmentation process 10 receives 1104 a selection of the acoustic domain associated with a conference room where the microphones are positioned on a table a few meters away from the speakers. In this example, data augmentation process 10 may perform 1106 one or more reverberation-based augmentations on at least a portion of the feature-based voice data of the first acoustic domain (e.g., the acoustic domain associated with a telephone conference where a speaker is talking very close to the microphone).

In some implementations, data augmentation process 10 may perform 1106 one or more reverberation-based augmentations on at least a portion of feature-based voice data 1200 to account for the variations in reverberation. Accordingly, data augmentation process 10 may perform 1106 reverberation-based augmentations to map feature-based voice data 1200 from the first acoustic domain (e.g., the acoustic domain associated with a telephone conference where a speaker is talking very close to the microphone) to a target acoustic domain (e.g., the acoustic domain associated with a conference room where the microphones are positioned on a table a few meters away from the speakers). In this manner, a speech processing system may be trained using feature-based voice data from one acoustic domain for processing speech in another acoustic domain.

In some implementations, data augmentation process 10 may determine a distribution of reverberation levels associated with the target acoustic domain. For example and in some implementations, when performing 1106 the one or more reverberation-based augmentations on feature-based voice data associated with a first acoustic domain for use in a target acoustic domain, the target acoustic domain may not have a constant reverberation level present in recordings captured within the target acoustic domain. In this example, data augmentation process 10 may determine a distribution of reverberations associated with the target acoustic domain. For example, data augmentation process 10 may process training data (e.g., time domain data and/or feature-based voice data) from the target acoustic domain to determine a distribution of reverberation levels. In some implementations, determining the distribution of reverberation from training data associated with the target acoustic domain may include determining how the reverberation within the training data varies over time for particular frequencies or frequency bands. In this manner, data augmentation process 10 may determine a distribution of reverberation levels to add or remove when performing reverberation-based augmentations on the feature-based voice data associated with the first acoustic domain.

In some implementations, performing 1112 the one or more reverberation-based augmentations to the at least a portion of the feature-based voice data may include performing the one or more reverberation-based augmentations to the at least a portion of the feature-based voice data based upon, at least in part, the distribution of reverberation levels associated with the target acoustic domain. As discussed above, with a distribution of reverberation levels associated with the target domain, data augmentation process 10 may perform one or more reverberation-based augmentations on at least a portion of the feature-based voice data to include a similar distribution of reverberation levels as the target acoustic domain.

In some implementations, suppose data augmentation process 10 determines a distribution of reverberation levels (e.g., distribution of reverberation levels 1204) associated with the target acoustic domain (e.g., the acoustic domain associated with a conference room where the microphones are positioned on a table a few meters away from the speakers). In this example, data augmentation process 10 may perform one or more reverberation-based augmentations on the feature-based voice data (e.g., feature-based voice data 1200) associated with the first acoustic domain (e.g., the acoustic domain associated with a telephone conference where a speaker is talking very close to the microphone) to include a similar or the same distribution of reverberation levels as in the target acoustic domain.

As will be discussed in greater detail below, data augmentation process 10 may perform these reverberation-based augmentations on feature-based voice data 1200 by adding reverberation to and/or removing reverberation from feature-based voice data 1200 based upon, at least in part, the distribution of reverberation levels associated with the target domain. In this manner, data augmentation process 10 may allow feature-based voice data 1200 associated with one acoustic domain (e.g., the acoustic domain associated with a telephone conference where a speaker is talking very close to the microphone) to be used to train speech processing systems in a target acoustic domain (e.g., the acoustic domain associated with a conference room where the microphones are positioned on a table a few meters away from the speakers), thus defining reverberation-augmented feature-based voice data (e.g., reverberation-augmented feature-based voice data 1206).

While an example of performing one or more reverberation-based augmentations on at least a portion of feature-based voice data has been described for augmenting feature-based voice data to include a similar distribution of reverberation levels as that of a target acoustic domain, it will be appreciated that data augmentation process 10 may perform one or more reverberation-based augmentations on at least a portion of feature-based voice data for other purposes within the scope of the present disclosure. As discussed above, data augmentation may allow an existing set of training data to be used in other acoustic domains or to provide more diverse training data within the same acoustic domain.

For example, suppose that a speech processing system is trained with training data having particular a reverberation level (e.g., measured in $T_{60}$, $C_{50}$, etc.). If a speech processing system is exposed to speech signals with reverberation levels that vary from the training data, the speech processing system may be less effective in processing the speech signal. In this manner, data augmentation process 10 may perform 1102 one or more reverberation-based augmentations on at least a portion of the feature-based voice data to generate more diverse training data for a speech processing system (e.g., training data with varying reverberation).

In some implementations, performing 1102 the one or more reverberation-based augmentations to the at least a portion of the feature-based voice data may include adding 1108 reverberation to the at least a portion of the feature-based voice data. For example, suppose that data augmentation process 10 receives 1100 feature-based voice data 1200 associated with a first acoustic domain (e.g., an acoustic domain associated with a telephone conference where a speaker is talking very close to the microphone) and receives 1104 a selection of a target acoustic domain (e.g., an acoustic domain associated with a conference room where the microphones are positioned on a table a few meters away from the speakers).

Data augmentation process 10 may determine that the target acoustic domain has a particular reverberation level or distribution of reverberation levels (e.g., measured in $T_{60}$, $C_{50}$, etc.) and that feature-based voice data 1200 has a different reverberation level or distribution. In this example, as feature-based voice data is recorded by a microphone positioned close to the speaker and the target acoustic domain is conference room where the microphones are positioned on a table a few meters away from the speakers, the reverberation level of the target acoustic domain is likely to be higher than the reverberation level recorded in feature-based voice data 1200. Accordingly, data augmentation process 10 may perform 1102 one or more reverberation-based augmentations by adding 1108 reverberation to at least a portion of feature-based voice data 1200 based upon, at least in part, the target acoustic domain.

In some implementations, performing 1102 the one or more reverberation-based augmentations to the at least a portion of the feature-based voice data may include removing 1110 reverberation to the at least a portion of the feature-based voice data. For example, suppose that data augmentation process 10 receives 1100 feature-based voice data 1200 associated with a first acoustic domain (e.g., an acoustic domain associated with a conference room where the microphones are positioned on a table a few meters away from the speakers) and receives 1104 a selection of a target acoustic domain (e.g., an acoustic domain associated with a telephone conference where a speaker is talking very close to the microphone).

Data augmentation process 10 may determine that the target acoustic domain has a particular reverberation level or distribution of reverberation levels (e.g., measured in $T_{60}$, $C_{50}$, etc.) and that feature-based voice data 1200 has a different reverberation level or distribution. In this example, as feature-based voice data is recorded in a conference room where the microphones are positioned on a table a few meters away from the speakers and the target acoustic domain is a telephone conference where a speaker is talking very close to the microphone, the reverberation level of the target acoustic domain is likely to be lower than the reverberation level recorded in feature-based voice data 1200. Accordingly, data augmentation process 10 may perform 1102 one or more reverberation-based augmentations by removing 1110 reverberation to at least a portion of feature-based voice data 1200 based upon, at least in part, the target acoustic domain.

In some implementations, data augmentation process 10 may perform 1102 the one or more reverberation-based augmentations by applying a gain factor to augment the effect of reverberation. For example, data augmentation process 10 may apply a channel-dependent gain factor to one or more channels of feature-based voice data 1200 (e.g., one or more Mel channels). In one example, data augmentation process 10 may apply a channel-dependent gain factor to each channel of feature-based voice data 1200. In this manner, data augmentation process 10 may add 1108 and/or remove 1110 reverberation to at least a portion of feature-based voice data 1200 by applying one or more channel-dependent gain factors.

In some implementations, data augmentation process 10 may perform 1102 the one or more reverberation-based augmentations by applying a decaying function (e.g., a decaying exponential function) to augment the effect of reverberation. For example, data augmentation process 10 may apply a decaying function to one or more channels of feature-based voice data 1200. In one example, data augmentation process 10 may apply different decaying functions to each channel of feature-based voice data 1200. Accordingly, the decaying function(s) may directly influence the reverberation level in each channel of feature-based voice data 1200 (e.g., as reverberation-augmented feature-based voice data 1206).

As discussed above, reverberation may be a function of the environment of the signal (e.g., how the signal reflects off of objects in the room adjacent to the signal source). Accordingly, in order to model the effects of reverberation, a room impulse response may be generated. However, applying a room impulse response in the feature domain using conventional data augmentation techniques is not feasible. For example, conventional data augmentation techniques require a signal to be converted back to the time domain. A room impulse response is typically 300 to 600 milliseconds long. As such, to model reverberation, a large frame size in the frequency domain is required. However, frames for speech processing systems are typically between 20 to 35 milliseconds long. Accordingly, a simple multiplication of feature-based voice data 1200 with a feature domain representation of a room impulse response may not augment feature-based voice data 1200 to include reverberation based upon, at least in part, the room impulse response.

In some implementations, data augmentation process 10 may train 1112 a machine learning model with one or more room impulse responses associated with the target acoustic domain. Referring also to the example of FIG. 13 and in some implementations, data augmentation process 10 may train a machine learning model (e.g., a neural network) to mimic the effect of reverberation by "learning" a filter in the feature domain. In one example, the machine learning model (e.g., machine learning model 72) may include a convolutional neural network (CNN) trained with training data (e.g., clean speech) and one or more room impulse responses associated with a target acoustic domain. While an example of a convolutional neural network has been described for machine learning model 72, it will be appreciated that any neural network, deep learning system, artificial intelligence system, or other machine learning model may be used within the scope of the present disclosure.

In some implementations, the room impulse response may be measured in an actual room and/or may be simulated using various algorithms known in the art. In some implementations, machine learning model 72 may train with e.g., one filter and linear activations based upon feature-based voice data (e.g., number of channels in the feature domain, nMel) and a number of frames based upon the reverberation level (e.g., the measured $T_{60}$). In one example, the number of frames may be 12. However, it will be appreciated that any number of frames may be utilized within the scope of the present disclosure. In some implementations, the trained machine learning model may output a trained filter template (e.g., filter 1300) configured to augment feature-based voice data with a particular reverberation level or distribution of reverberation levels in the feature domain.

In some implementations, performing 1102 the one or more reverberation-based augmentations to the at least a portion of the feature-based voice data may include performing 1114 the one or more reverberation-based augmentations to the at least a portion of the feature-based voice data using the trained machine learning model configured to model the reverberation associated with the target acoustic domain. For example, once the filter template(s) are trained, data augmentation process 10 may perform 1114 the one or more reverberation-based augmentations to the at least a portion of the feature-based voice data using the trained machine learning model (e.g., machine learning model 72) by applying the trained filter template (e.g., filter 1300) to feature-based voice data 1200. In one example, machine learning model 72 may apply filter 1300 in a manner similar to convolution in image processing (e.g., where the "image" in this example is a section of feature-based voice data 1200 (e.g., the Mel spectrum) and filter 1300 captures the time/frequency dependent smearing effect of a room impulse response). Accordingly, data augmentation process 10 may train filter 1300 once on a small dataset and then can be applied to any feature-based voice data directly in the feature domain (e.g., the Mel domain).

Machine Learning Model Feature-Based Voice Data Augmentation

In some implementations, data augmentation process 10 may receive 1400 feature-based voice data. One or more data augmentation characteristics may be received 1402. One or more augmentations of the feature-based voice data may be generated 1404, via a machine learning model, based upon, at least in part, the feature-based voice data and the one or more data augmentation characteristics.

As will be discussed in greater detail below, data augmentation process 10 may allow a machine learning model to generate 1404 one or more augmentations of feature-based voice data in the feature domain without accessing the original signal (e.g., in the time domain) by training the machine learning model with several examples of original signals (e.g., in the time domain) and augmented feature-based voice data (e.g., in the feature domain). In this manner, data augmentation process 10 may generate 1404 augmented feature-based voice data with input feature-based voice data and particular data augmentation characteristics without accessing the time domain version of the input feature-based voice data.

As will be discussed in greater detail below, process 10 may allow a machine learning model to generate 1404 augmented training data without requiring the machine learning model to be trained with equivalent time domain data from various acoustic domains. For example, conventional data augmentation techniques may allow a mapping of one image domain to another image domain by training systems with the same recorded data from each image domain. However, the ability to capture training data in each set of domains may be impractical for these techniques and may not allow speech processing systems to be fully trained for an acoustic domain until time domain signals are recorded in each domain. In some implementations, data augmentation process 10 may train a machine learning model to perform complex combinations of augmentations, as opposed augmentations from a single domain to another domain. For example, by training the machine learning model with training data requiring various augmentations, data augmentation process 10 may generate 1404 augmented feature-based voice data directly in the feature domain by utilizing the training of individual augmentation parameters. In this manner, the trained machine learning model may be able to generalize augmentations outside of the bounds of specific training data.

In some implementations, data augmentation process 10 may train a machine learning model to perform one or more augmentations on at least a portion of feature-based voice data. Referring also to the example of FIG. 15 and in some implementations, a machine learning model (e.g., machine learning model 1500) may be configured to receive one or more signals in the time domain (e.g., signal 1502), one or more augmentations of the one or more signals in the time domain (e.g., augmented time domain signal 1504), feature-based voice data associated with the one or more signals (e.g., feature-based voice data 1506), and augmentations of the feature-based voice data corresponding to the one or more augmentations of the one or more signals in the time domain (e.g., augmented feature-based voice data 1508). In some implementations, data augmentation process 10 may perform one or more augmentations (e.g., defined by conditioning vector 1510) on signal 1502 to generate augmented time domain signal 1504 and may convert augmented time domain signal 1504 to the feature domain to generate augmented feature-based voice data 1508. As will be discussed in greater detail below, data augmentation process 10 may utilize augmented feature-based voice data 1508 to train machine learning model 1500.

In some implementations and as will be discussed in greater detail below, training machine learning model 1500 may include tuning various augmentation parameters associated with augmenting feature-based voice data. Referring again to the example of FIG. 15 and in some implementations, data augmentation process 10 may receive feature-based voice data 1506 converted from signal 1502. However, in some embodiments, data augmentation process 10 may receive signal 1502 and convert signal 1502 to the feature domain to generate feature-based voice data 1506.

In some implementations, data augmentation process 10 may receive conditioning vector 1510 describing the augmentations to perform on signal 1502 and/or feature-based voice data 1506. For example, conditioning vector 1510 may define various desired characteristics for the augmented signal or augmented feature-based voice data. Examples of the augmentation characteristics defined by conditioning vector 1510 may generally include a noise type, a target SNR, a $T_{60}$ value, a $C_{50}$ value, etc. As will be described in greater detail below, conditioning vector 1510 may be an example of one or more data augmentation characteristics received by data augmentation process 10 and used to generate one or more augmentations of feature-based voice data.

In some implementations, data augmentation process 10 may process feature-based voice data 1506 and conditioning vector 1510 to perform one or more augmentations on feature-based voice data 1506. In some implementations, machine learning model 1500 may be configured with various parameters associated with different types of augmentations that may be performed on at least a portion of feature-based voice data 1506. For example, machine learning model 1500 may be configured to perform various types of augmentations represented by different tunable augmentation parameters or combination of tunable parameters (e.g., tunable augmentation parameters 1512, 1514, 1516, 1518, 1520). Examples of these types of augmentations may include one or more gain-based augmentations (e.g., represented by tunable augmentation parameter 1512); one or more rate-based augmentations (e.g., represented by tunable augmentation parameter 1514); one or more audio feature-based augmentations (e.g., represented by tunable augmentation parameter 1516); and one or more reverberation-based augmentations (e.g., represented by tunable augmentation parameter 1518). However, it will be appreciated that any type of augmentation or number of augmentations may be performed by machine learning model 1500 within the scope of the present disclosure.

Figure 15:
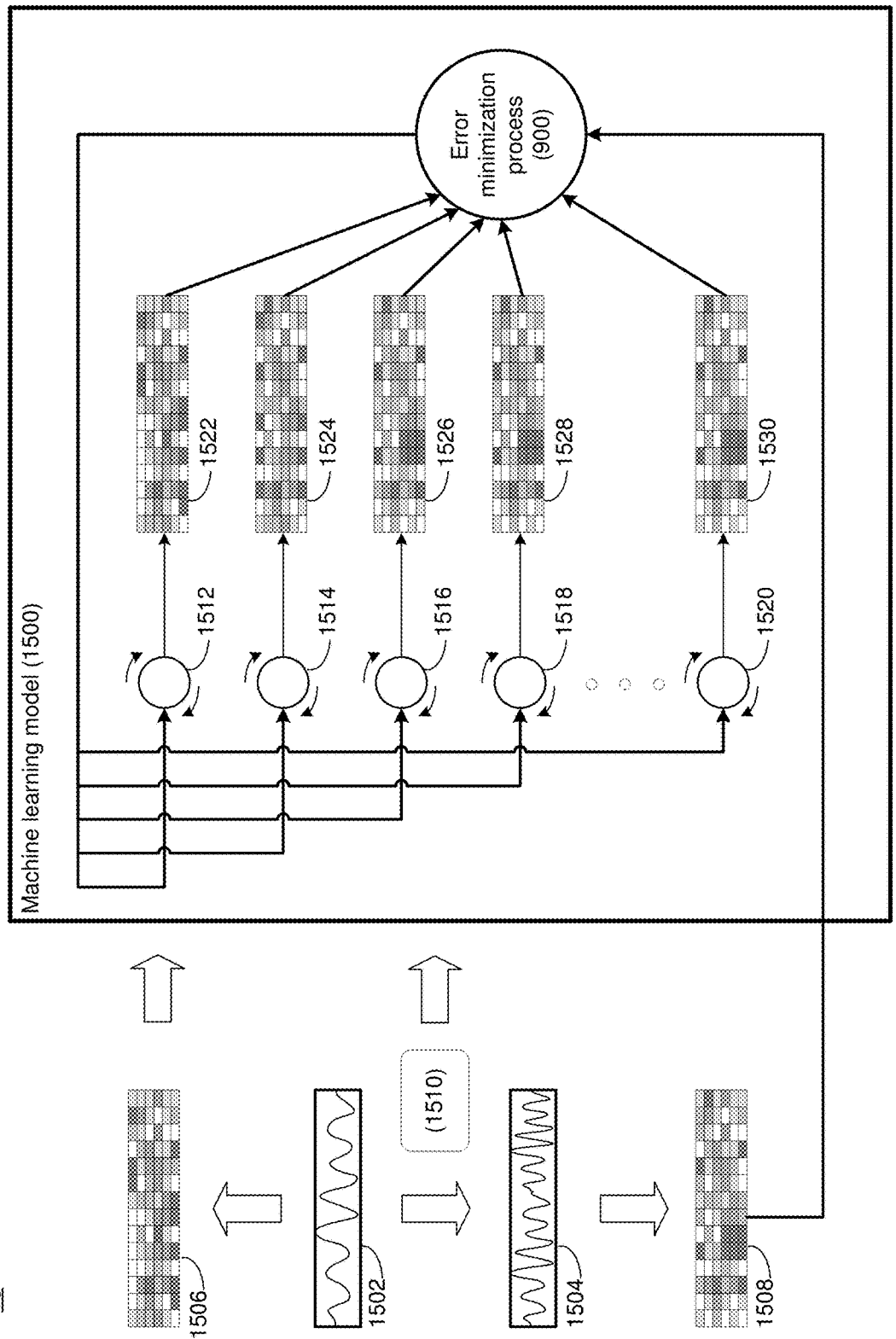
FIGS. 15-16 are diagrammatic views of machine learning models according to one implementation of the data augmentation process of FIG. 1.

As shown in the example of FIG. 15 and in some implementations, data augmentation process 10 may (e.g., via machine learning model 1500) process conditioning vector 1510 to determine which augmentations to perform on feature-based voice data 1506. For example, suppose that conditioning vector 1510 describes a particular gain for a particular frequency band; a particular speaking rate; a type of noise; and a reverberation level (e.g., defined as a $T_{60}$ value). In this example, data augmentation process 10 may (e.g., via machine learning model 1500) perform one or more gain-based augmentations based upon the particular gain for the specified frequency band to generate gain-augmented feature-based voice data 1522; one or more rate-based augmentations based upon the specified speaking rate to generate rate-based augmented feature-based voice data 1524; one or more audio feature-based augmentations to add the specified type of noise to generate audio feature-augmented feature-based voice data 1526; one or more reverberation-based augmentations to achieve the desired $T_{60}$ value to generate reverberation-augmented feature-based voice data 1528; and other augmented feature-based voice data 1530.

In some implementations, data augmentation process 10 may train machine learning model 1500 based upon, at least in part, the time domain augmentations and the augmented feature-based voice data corresponding to the one or more time domain augmentations by minimizing an error between the augmented feature-based voice data and the corresponding time domain augmentations. Referring again to the example of FIG. 15 and in some implementations, data augmentation process 10 may (e.g., via machine learning model 1500) compare the augmented feature-data generated by machine learning model (e.g., augmented feature-based voice data 1522, 1524, 1526, 1528, 1530) based upon, at least in part, conditional vector 510 with the augmentations of the feature-based voice data corresponding to the one or more augmentations of the one or more signals in the time domain (e.g., augmented feature-based voice data 1508).

In some implementations, data augmentation process 10 may minimize an error (e.g., via error minimization process 1532) associated with a comparison of the augmented feature-data generated by machine learning model 1500 (e.g., augmented feature-based voice data 1522, 1524, 1526, 1528, 1530) and the one or more augmentations of the one or more signals in the time domain (e.g., augmented feature-based voice data 1508). In some implementations, minimizing the error (e.g., via error minimization process 1532) may include adjusting the tunable augmentation parameters (e.g., tunable augmentation parameters 1512, 1514, 1516, 1518, 1520). In this manner, machine learning model 1500 may be configured to "learn" how to augment feature-based voice data across various tunable augmentation parameters.

In some implementations, data augmentation process 10 may receive 1400 feature-based voice data. Accordingly, data augmentation process 10 may extract 1406 acoustic metadata from the audio signal before converting 1408 the audio signal from the time domain to the feature domain. As discussed above, acoustic metadata may generally refer to information regarding the characteristics or properties of the signal. In some implementations, the acoustic metadata may only refer to properties of the signal without exposing or describing any speech content of the signal.

In some implementations, data augmentation process 10 may receive 1402 one or more data augmentation characteristics. Referring also to the example of FIG. 16 and in some implementations, data augmentation process 10 may receive 1402 one or more data augmentation characteristics (e.g., data augmentation characteristics 1600). In some implementations, data augmentation characteristics 1600 may be received via a user interface from one or more menus for selecting particular data augmentations to perform on feature-based voice data (e.g., feature-based voice data 1602). However, it will be appreciated that data augmentation characteristics 1600 may be received in various ways within the scope of the present disclosure.

As discussed above and in some implementations, data augmentation characteristics 1600 may define various desired characteristics for the augmented feature-based voice data (e.g., augmented feature-based voice data 1604). Examples of data augmentation characteristics that may be defined may generally include a noise type, a target SNR, a $T_{60}$ value, a $C_{50}$ value, etc. In some implementations, data augmentation process 10 may receive one or more data augmentation characteristics (e.g., data augmentation characteristics 1600) as one or more conditioning vectors (e.g., a vector-based representation of desired characteristics for the augmented feature-based voice data). However, it will be appreciated that the one or more data augmentation characteristics may be received in various formats within the scope of the present disclosure.

In some implementations, data augmentation process 10 may generate 1404, via a machine learning model, one or more augmentations of the feature-based voice data based upon, at least in part, the feature-based voice data and the one or more data augmentation characteristics. Referring again to the example of FIG. 16 and in some implementations, suppose data augmentation process 10 receives 1400 feature-based voice data 1602. As discussed above, feature-based voice data 1602 may include a feature domain representation of signal with various feature coefficients. For example, feature-based voice data 1602 may include a plurality of dimensions or feature coefficients (e.g., Mel frequency cepstral coefficients, Mel Filter Bank coefficients, etc.). Further suppose that data augmentation process 10 receives 1402 one or more data augmentation characteristics (e.g., data augmentation characteristics 1600) describing one or more desired characteristics for the augmented feature-based voice data (e.g., augmented feature-based voice data 1604).

In some implementations, generating 1404, via the machine learning model, the one or more augmentations of the feature-based voice data may include generating 1410, via the machine learning model, the one or more feature-based augmentations of the feature-based voice data based upon, at least in part, the feature-based voice data, the one or more data augmentation characteristics, and the acoustic metadata. Referring again to the example of FIG. 16 and as discussed above, data augmentation process 10 may extract 1406 acoustic metadata (e.g., acoustic metadata 1606) associated with feature-based voice data 1602 before converting the signal to the feature domain. In some implementations, acoustic metadata 1606 may describe the acoustic characteristics of feature-based voice data 1602 and/or portion of feature-based voice data 1602. Examples of acoustic characteristics may generally include a gain level, presence of a speech component, presence and type of a noise component, a speaking rate, a reverberation level, etc. In some implementations, acoustic metadata 1606 may provide machine learning model 1500 with a signal-specific "starting point" for augmenting feature-based voice data 1602.

For example and as discussed above, when a signal is converted to the feature domain, it may be impossible to determine acoustic characteristics of the signal without converting the signal back to the time domain and potentially exposing speech content. To avoid this challenge, acoustic metadata 1606 may describe these acoustic characteristics of a signal such that any augmentations of feature domain representation of the signal may be specific to feature-based voice data 1602. In some implementations without extracting acoustic metadata 1606, machine learning model 1500 may receive some general information associated with the acoustic characteristics of feature-based voice data (e.g., a categorization of feature-based voice data as speech recorded in a vehicle). With only this general information, the augmentations performed may be less tailored and accurate when applied to feature-based voice data 1602 than when augmentations are performed based upon, at least in part, acoustic metadata 1606. Accordingly, data augmentation process 10 may utilize acoustic metadata 1606 to determine which augmentations to perform on feature-based voice data 1602 to generate augmented feature-based voice data 1604 based upon, at least in part, data augmentation characteristics 1600.

In some implementations, generating 1404, via the machine learning model, the one or more augmentations of the feature-based voice data may include performing 1412, via the machine learning model, one or more gain-based augmentations on at least a portion of the feature-based voice data based upon, at least in part, the feature-based voice data and the one or more data augmentation characteristics. Referring again to the example of FIG. 16, suppose that feature-based voice data 1602 is associated with a first acoustic domain (e.g., an acoustic domain associated with a speaker speaking directly into a microphone within a laboratory). In some implementations, specific gain level information may be determined from acoustic metadata 1606 extracted from the time domain signal of feature-based voice data 1602.

Figure 16:
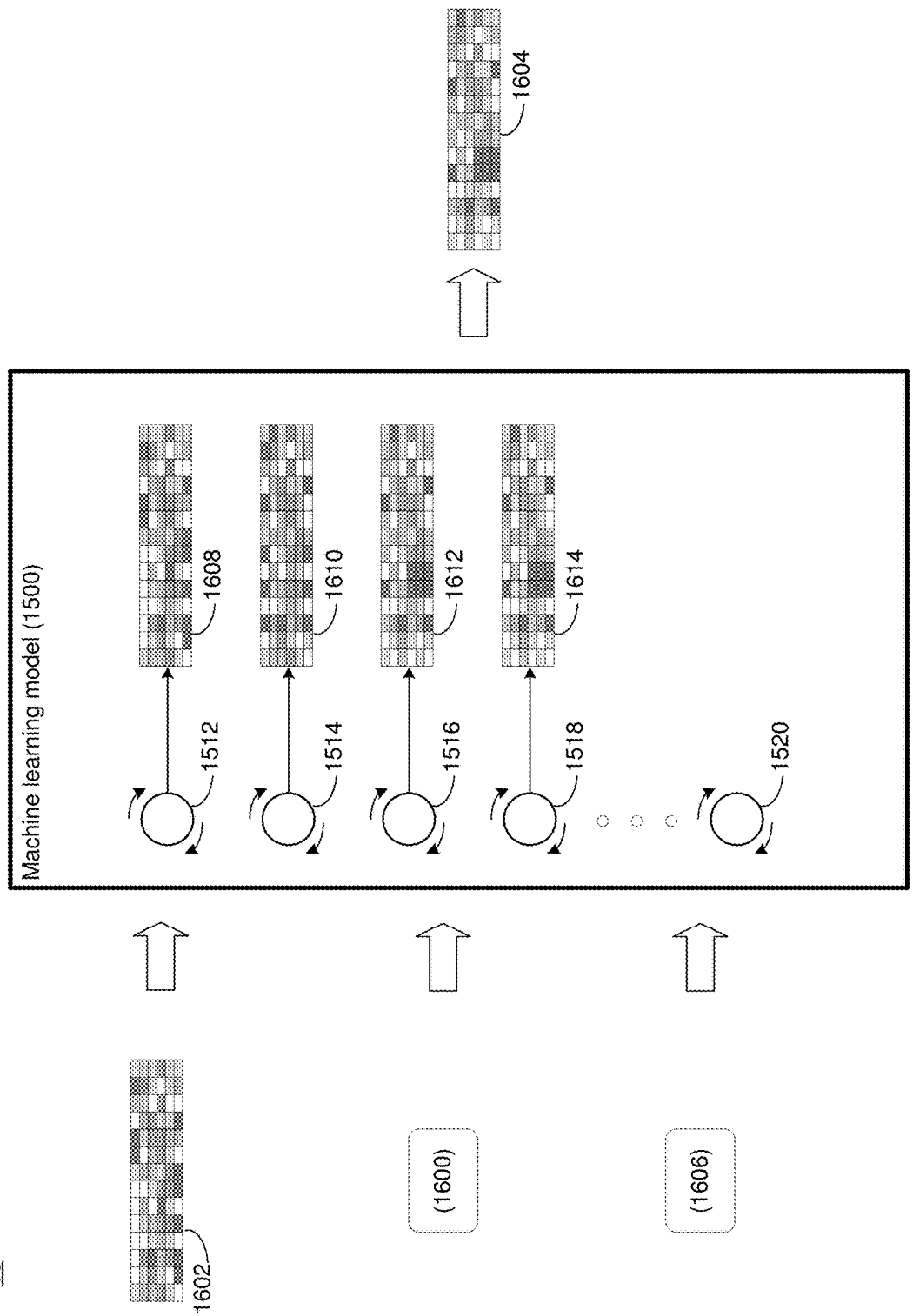

Continuing with the above example, suppose that data augmentation characteristics 1600 describe a distribution of gain levels for various frequencies. In this example, data augmentation process 10 may (e.g., via machine learning model 1500) utilize the trained parameters associated with gain-based augmentations (e.g., represented as parameter 1512) to generate 1404 augmented feature-based voice data 1608. In this example and as discussed above, machine learning model 1500 may perform 1412 one or more gain-based augmentations on at least a portion of feature-based voice data 1602 such that gain-augmented feature-based voice data 1608 includes the distribution of gain levels for the frequencies specified by data augmentation characteristics 1600. While the example of FIG. 16 shows gain-augmented feature-based voice data separately from other augmented feature-based voice data, it will be appreciated that machine learning model 1500 may perform 1412 the one or more gain-based augmentations to feature-based voice data 1602 in parallel and/or simultaneously with other augmentations within the scope of the present disclosure.

In some implementations, generating 1404, via the machine learning model, the one or more augmentations of the feature-based voice data may include performing 1414, via the machine learning model, one or more rate-based augmentations on at least a portion of the feature-based voice data based upon, at least in part, the feature-based voice data and the one or more data augmentation characteristics. Referring again to the example of FIG. 16 and as discussed above, suppose that feature-based voice data 1602 is associated with a first acoustic domain (e.g., an acoustic domain where a speaker speaks into a microphone dictation system configured to recognize and transcribe speech). In some implementations, a particular speaking rate or distribution of speaking rates may be determined from acoustic metadata 1606 extracted from the time domain signal of feature-based voice data 1602.

Continuing with the above example, suppose that data augmentation characteristics 1600 describe a distribution of speaking rates. In this example, data augmentation process 10 may (e.g., via machine learning model 1500) utilize the trained parameters associated with rate-based augmentations (e.g., represented as parameter 1514) to generate 1404 augmented feature-based voice data 1610. In this example and as discussed above, machine learning model 1500 may perform 1414 one or more rate-based augmentations on at least a portion of feature-based voice data 1602 such that rate-based augmented feature-based voice data 1610 includes the distribution of speaking rates specified by data augmentation characteristics 1600.

In some implementations, generating 1404, via the machine learning model, the one or more augmentations of the feature-based voice data may include performing 1416, via the machine learning model, one or more audio feature-based augmentations on at least a portion of the feature-based voice data based upon, at least in part, the feature-based voice data and the one or more data augmentation characteristics. Referring again to the example of FIG. 16 and as discussed above, suppose that feature-based voice data 1602 is associated with a first acoustic domain (e.g., an acoustic domain associated with a medical professional's office including a microphone array configured to process conversations between medical professionals and patients). In some implementations, specific audio feature(s) may be determined from acoustic metadata 1606 extracted from the time domain signal of feature-based voice data 1602.

Continuing with the above example, suppose that data augmentation characteristics 1600 describe a distribution of noise features across various frequencies (e.g., noise features associated with noise captured while capturing speech within a particular type of vehicle). In this example, data augmentation process 10 may (e.g., via machine learning model 1500) utilize the trained parameters associated with audio feature-based augmentations (e.g., represented as parameter 1516) to generate 1404 augmented feature-based voice data 1612. In this example and as discussed above, machine learning model 1500 may perform 1416 one or more audio feature-based augmentations on at least a portion of feature-based voice data 1602 such that audio feature-augmented feature-based voice data 1612 includes the distribution of noise features for the frequencies specified by data augmentation characteristics 1600.

In some implementations, generating 1404, via the machine learning model, the one or more augmentations of the feature-based voice data may include performing 1418, via the machine learning model, one or more reverberation-based augmentations on at least a portion of the feature-based voice data based upon, at least in part, the feature-based voice data and the one or more data augmentation characteristics. Referring again to the example of FIG. 16 and as discussed above, suppose that feature-based voice data 1602 is associated with a first acoustic domain (e.g., an acoustic domain associated with a speaker speaking into a microphone array deployed in an enclosed office space). In some implementations, a specific reverberation level (e.g., defined as a $T_{60}$ value) may be determined from acoustic metadata 1606 extracted from the time domain signal of feature-based voice data 1602.

Suppose that data augmentation characteristics 1600 describe a distribution of reverberation (e.g., $T_{60}$ values associated with a conference room and microphones placed on a table a few meters away from the speakers). In this example, data augmentation process 10 may (e.g., via machine learning model 1500) utilize the trained parameters associated with reverberation-based augmentations (e.g., represented as parameter 1518) to generate 1404 augmented feature-based voice data 1614. In this example and as discussed above, machine learning model 1500 may perform 1418 one or more reverberation-based augmentations on at least a portion of feature-based voice data 1602 such that reverberation-augmented feature-based voice data 1614 includes the reverberation specified by data augmentation characteristics 1600.

While the above examples describe generating 1404 the one or more augmentations separately, it will be appreciated that the one or more augmentations may be performed in parallel and/or simultaneously within the scope of the present disclosure. It will also be appreciated that the above example types of augmentations are for example purposes only and do not preclude other types of augmentations that may be performed within the scope of the present disclosure.

In some implementations, data augmentation process 10 may train a speech processing system using the augmented feature-based voice data. As discussed above and in some implementations, data augmentation process 10 may generate augmented feature-based voice data that, when used in the training of a speech processing system, allows the speech processing system to be more robust against such acoustic variations. In some implementations, training a speech processing system may generally include training one or more speech processing models (e.g., machine learning or neural network models) configured to process a speech signal for various purposes. For example, speech processing system may generally include an automated speech recognition (ASR) system, a voice biometric system, emotion detection system, medical symptom detection symptom, hearing enhancement system, etc. In one example, training a speech processing system may include training an ASR system configured to process a speech signal to generate recognized speech. In this manner, an automated speech recognition system may be improved to recognize speech signals with acoustic variations resulting from a moving speaker and/or adaptive beamforming. While an example of ASR system has been provided, it will be appreciated that any speech processing system may be trained within the scope of the present disclosure.

In some implementations, automated speech recognition may be performed via the trained speech processing system executed on the same computing device that trained the speech processing system and/or on another computing device. Accordingly, it will be appreciated that generating augmented data (e.g., augmented feature-based voice data), training a speech processing system with the augmented data, and performing speech processing via the trained speech processing system may be performed on the same computing device and/or discrete computing devices within the scope of the present disclosure.

In some implementations, data augmentation process 10 may perform speech processing via the trained speech processing system, where the trained speech processing system is executed on at least one computing device. For example, embodiments of data augmentation process 10 may be used in ambient speech applications, such as Dragon® Speech Recognition Software available from Nuance Communications, Inc. of Burlington, Mass., with multiple, distant microphones or for a health care application where the doctor and patient speech is acquired through a microphone array (e.g., using Dragon® Ambient eXperience™ (DAX)); Dragon is a registered trademark of Nuance Communications, Inc. in the United States, other countries or both. In some implementations, embodiments of data augmentation process 10 may be utilized to enhance ASR performance in various settings (e.g., voice-based vehicular control systems, voice-based dialogue systems, etc.). In some implementations, speech processing may be performed via the trained speech processing system executed on the same computing device that trained the speech processing system and/or on another computing device. Accordingly, it will be appreciated that generating augmented data (e.g., augmented feature-based voice data), training a speech processing system with the augmented data, and performing speech processing via the trained speech processing system may be performed on the same computing device and/or discrete computing devices within the scope of the present disclosure.

Figure 17:
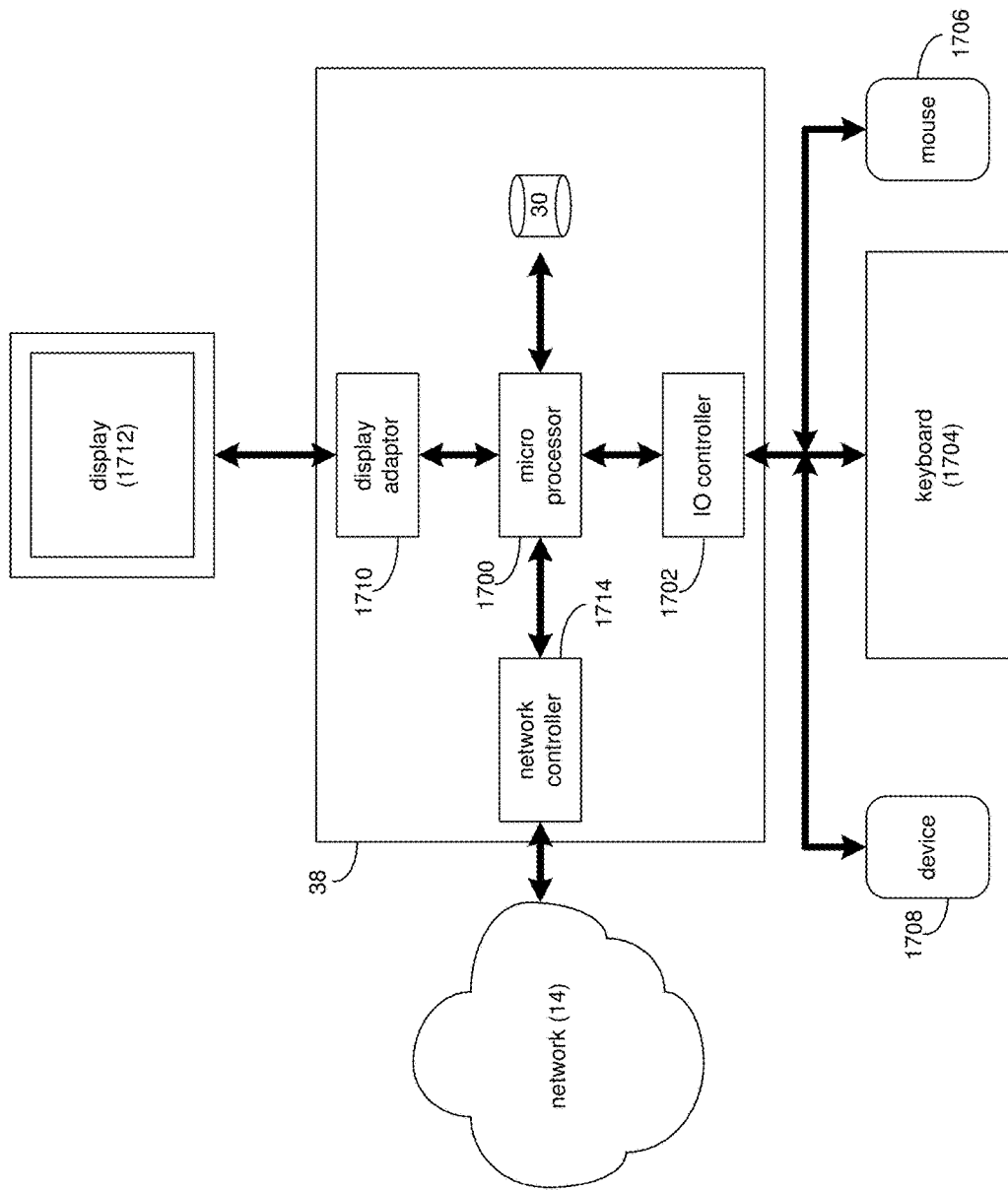
FIG. 17 is an example diagrammatic view of a client electronic device of FIG. 1 according to one or more example implementations of the disclosure.

Referring also to FIG. 17, there is shown a diagrammatic view of client electronic device 38. While client electronic device 38 is shown in this figure, this is for illustrative purposes only and is not intended to be a limitation of this disclosure, as other configurations are possible. For example, any computing device capable of executing, in whole or in part, data augmentation process 10 may be substituted for client electronic device 38 within FIG. 17, examples of which may include but are not limited to computing device 12 and/or client electronic devices 40, 42, 44.

Client electronic device 38 may include a processor and/or microprocessor (e.g., microprocessor 1700) configured to, e.g., process data and execute the above-noted code/instruction sets and subroutines. Microprocessor 1700 may be coupled via a storage adaptor (not shown) to the above-noted storage device(s) (e.g., storage device 30). An I/O controller (e.g., I/O controller 1702) may be configured to couple microprocessor 1700 with various devices, such as keyboard 1704, pointing/selecting device (e.g., mouse 1706), custom device, such a microphone (e.g., device

1708), USB ports (not shown), and printer ports (not shown). A display adaptor (e.g., display adaptor 1710) may be configured to couple display 1712 (e.g., CRT or LCD monitor(s)) with microprocessor 1700, while network controller/adaptor 1714 (e.g., an Ethernet adaptor) may be configured to couple microprocessor 1700 to the above-noted network 14 (e.g., the Internet or a local area network).

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
   receiving feature-based voice data associated with a first acoustic domain, wherein the feature-based voice data is converted from a signal in the first acoustic domain to a feature domain;
   performing one or more gain-based augmentations on at least a portion of the feature-based voice data converted from the signal in the first acoustic domain to the feature domain, thus defining gain-augmented feature-based voice data;
   receiving a selection of a target acoustic domain;
   determining a distribution of gain levels from training data associated with the target acoustic domain varies over time for one or more of particular frequencies and particular frequency bands;
   mapping the gain-augmented feature-based voice data from the first acoustic domain to the target acoustic domain, and
   training a speech processing system for the target acoustic domain based on the gain-augmented feature-based voiced data mapped from the first acoustic domain to the target acoustic domain.

2. The computer-implemented method of claim 1, further comprising:
   receiving the selection of the target acoustic domain via at least one of a user interface and a database.

3. The computer-implemented method of claim 2, wherein performing the one or more gain-based augmentations to the at least a portion of the feature-based voice data includes performing the one or more gain-based augmentations to the at least a portion of the feature-based voice data based upon, at least in part, the target acoustic domain.

4. The computer-implemented method of claim 2, further comprising:
   determining a distribution of gain levels associated with the target acoustic domain.

5. The computer-implemented method of claim 4, wherein performing the one or more gain-based augmentations to the at least a portion of the feature-based voice data includes performing the one or more gain-based augmentations to the at least a portion of the feature-based voice data based upon, at least in part, the distribution of gain levels associated with the target acoustic domain.

6. The computer-implemented method of claim 1, wherein performing the one or more gain-based augmentations to the at least a portion of the feature-based voice data includes amplifying the at least a portion of the feature-based voice data.

7. The computer-implemented method of claim 1, wherein performing the one or more gain-based augmentations to the at least a portion of the feature-based voice data includes attenuating the at least a portion of the feature-based voice data.

8. A computer program product residing on a non-transitory computer readable medium having a plurality of instructions stored thereon which, when executed by a processor, cause the processor to perform operations comprising:
   receiving feature-based voice data associated with a first acoustic domain, wherein the feature-based voice data is converted from a signal in the first acoustic domain to a feature domain;
   performing one or more gain-based augmentations on at least a portion of the feature-based voice data converted from the signal in the first acoustic domain to the feature domain, thus defining gain-augmented feature-based voice data;
   receiving a selection of a target acoustic domain;
   determining a distribution of gain levels from training data associated with the target acoustic domain varies over time for one or more of particular frequencies and particular frequency bands;
   mapping the gain-augmented feature-based voice data from the first acoustic domain to the target acoustic domain, and
   training a speech processing system for the target acoustic domain based on the gain-augmented feature-based voiced data mapped from the first acoustic domain to the target acoustic domain.

9. The computer program product of claim 8, wherein the operations further comprise:
   receiving the selection of the target acoustic domain via at least one of a user interface and a database.

10. The computer program product of claim 9, wherein performing the one or more gain-based augmentations to the at least a portion of the feature-based voice data includes performing the one or more gain-based augmentations to the at least a portion of the feature-based voice data based upon, at least in part, the target acoustic domain.

11. The computer program product of claim 9, wherein the operations further comprise:
    determining a distribution of gain levels associated with the target acoustic domain.

12. The computer program product of claim 11, wherein performing the one or more gain-based augmentations to the at least a portion of the feature-based voice data includes performing the one or more gain-based augmentations to the at least a portion of the feature-based voice data based upon, at least in part, the distribution of gain levels associated with the target acoustic domain.

13. The computer program product of claim 8, wherein performing the one or more gain-based augmentations to the at least a portion of the feature-based voice data includes amplifying the at least a portion of the feature-based voice data.

14. The computer program product of claim 8, wherein performing the one or more gain-based augmentations to the at least a portion of the feature-based voice data includes attenuating the at least a portion of the feature-based voice data.

15. A computing system comprising:
a memory; and
a processor configured to receive feature-based voice data associated with a first acoustic domain, wherein the feature-based voice data is converted from a signal in the first acoustic domain to a feature domain, wherein the processor is further configured to perform one or more gain-based augmentations on at least a portion of the feature-based voice data converted from the signal in the first acoustic domain to the feature domain, thus defining gain-augmented feature-based voice data, wherein the processor is further configured to receive a selection of a target acoustic domain, wherein the processor is further configured to determine a distribution of gain levels from training data associated with the target acoustic domain varies over time for one or more of particular frequencies and particular frequency bands; wherein the processor is further configured to map the gain-augmented feature-based voice data from the first acoustic domain to the target acoustic domain; and wherein the processor is further configured to train a speech processing system for the target acoustic domain based on the gain-augmented feature-based voiced data mapped from the first acoustic domain to the target acoustic domain.

16. The computing system of claim 15, wherein the processor is further configured to:
receive the selection of the target acoustic domain via at least one of a user interface and a database.

17. The computing system of claim 16, wherein performing the one or more gain-based augmentations to the at least a portion of the feature-based voice data includes performing the one or more gain-based augmentations to the at least a portion of the feature-based voice data based upon, at least in part, the target acoustic domain.

18. The computing system of claim 16, wherein the processor is further configured to:
determine a distribution of gain levels associated with the target acoustic domain.

19. The computing system of claim 18, wherein performing the one or more gain-based augmentations to the at least a portion of the feature-based voice data includes performing the one or more gain-based augmentations to the at least a portion of the feature-based voice data based upon, at least in part, the distribution of gain levels associated with the target acoustic domain.

20. The computing system of claim 15, wherein performing the one or more gain-based augmentations to the at least a portion of the feature-based voice data includes one or more of:
amplifying the at least a portion of the feature-based voice data; and
attenuating the at least a portion of the feature-based voice data.

* * * * *